United States Patent [19]
Or et al.

[11] Patent Number: 5,604,234
[45] Date of Patent: Feb. 18, 1997

[54] SUBSTITUTED THIOL MACROLACTAM IMMUNOMODULATORS

[75] Inventors: Yat S. Or; Jay R. Luly, both of Libertyville, Ill.

[73] Assignee: Abbott Laboratories, Abbott Park, Ill.

[21] Appl. No.: 529,862

[22] Filed: Sep. 18, 1995

Related U.S. Application Data

[63] Continuation-in-part of Ser. No. 149,416, Nov. 9, 1993, Pat. No. 5,457,111, which is a continuation-in-part of Ser. No. 32,958, Mar. 17, 1993, abandoned, which is a continuation-in-part of PCT/US92/07600, Sep. 8, 1992, which is a continuation-in-part of Ser. No. 755,208, Sep. 5, 1991, abandoned.

[51] Int. Cl.$^6$ ...................... A61K 31/395; A61K 31/695; C07D 191/16
[52] U.S. Cl. ........................ 514/291; 514/411; 540/456
[58] Field of Search ............................ 540/456; 514/411, 514/291

[56] References Cited

FOREIGN PATENT DOCUMENTS

WO93/04680  3/1993  WIPO ........................... A61K 31/395
WO94/21644  9/1994  WIPO ........................... A61K 31/395

*Primary Examiner*—Robert T. Bond
*Attorney, Agent, or Firm*—Steven R. Crowley; Gregory W. Steele

[57] ABSTRACT

Immunomodulatory macrocyclic compounds having the formula:

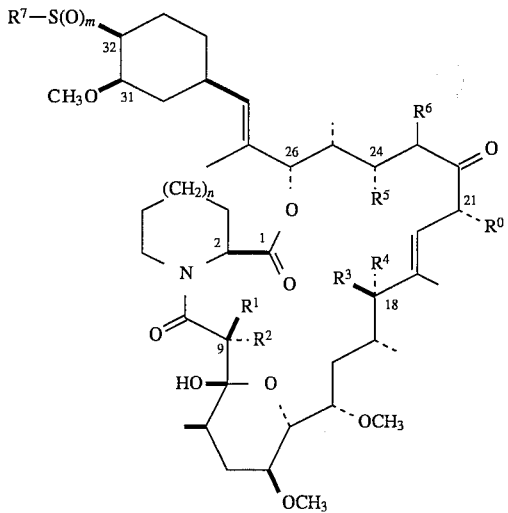

and pharmaceutically acceptable salts, esters, amides and prodrugs thereof, as well as pharmaceutical compositions containing such compounds and therapeutic methods of their use.

26 Claims, No Drawings

SUBSTITUTED THIOL MACROLACTAM IMMUNOMODULATORS

This application is a continuation-in-part of U.S. patent application Ser. No. 08/149,416, filed Nov. 9, 1993, now U.S. Pat. No. 5,457,111 which is a continuation-in-part of U.S. patent application Ser. No. 08/032,958, filed Mar. 17, 1993, now abandoned, which is a continuation-in-part of co-pending International Patent Application No. PCT/US92/07600, filed Sep. 8, 1992, which is a continuation-in-part of U.S. patent application Ser. No. 07/755,208, filed Sep. 5, 1991 and now abandoned.

TECHNICAL FIELD

The present invention relates to novel chemical compounds having immunomodulatory activity, and in particular to macrolide immunosuppressants. More particularly, the invention relates to semisynthetic analogs of ascomycin and FK-506, to means for their preparation, to pharmaceutical compositions containing such compounds and to methods of treatment employing the same.

BACKGROUND OF THE INVENTION

The compound cyclosporine (cyclosporin A) has found wide use since its introduction in the fields of organ transplantation and immunomodulation, and has brought about a significant increase in the success rate for transplantation procedures. Undesired side-effects associated with cyclosporine, however, such as nephrotoxicity, have led to a continued search for immunosuppressant compounds having improved efficacy and safety.

Recently, several classes of macrocyclic compounds having potent immunomodulatory activity have been discovered. Okuhara et at., in European Patent Application No. 184162, published Jun. 11, 1986, disclose a number of macrocyclic compounds isolated from the genus Streptomyces. Immunosuppressant FK-506, isolated from a strain of *S. tsukubaensis*, is a 23-membered macrocyclic lactone represented by formula 1 a, below. Other related natural products, such as FR-900520 (1b) and FR-900523 (1c), which differ from FK-506 in their alkyl substituent at C-21, have been isolated from *S. hygroscopicus yakushimnaensis*. Yet another analog, FR-900525, produced by *S. tsukubaensis*, differs from FK-506 in the replacement of a pipecolic acid moiety with a proline group.

FR-900520, also known as ascomycin, has been previously disclosed by Arai et al. in U.S. Pat. No. 3,244,592, issued Apr. 5, 1966, where the compound is described as an antifungal agent. Monaghan, R. L., et al., on the other hand, describe the use of ascomycin as an immunosuppressant in European Patent Application No. 323865, published Jul. 12, 1989.

Although the immunosuppressive activity of FK-506 has been clinically confirmed, its toxicity in mammals has limited its utility. The activity of FK-506 has, however, prompted efforts to discover novel analogs of FK-type compounds which possess superior properties. These efforts include the isolation of new fermentation products, the microbial transformation of existing chemical entities, the chemical modification of these macrocycles, and the synthesis of hybrid species derived from smaller synthetic fragments.

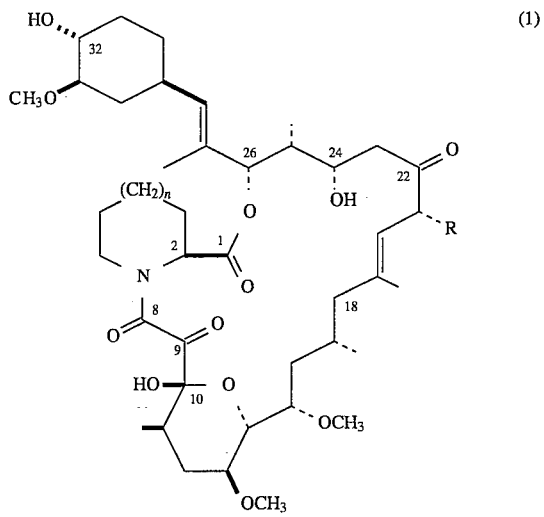

1(a): FK-506    R = CH$_2$CH=CH$_2$; n = 1
1(b): FR-900520   R = CH$_2$CH$_3$; n = 1
1(c): FR-900523   R = CH$_3$; n = 1
1(d): FR-900525   R = CH$_2$CH=CH$_2$; n = 0

Fermentation products of FK-type compounds include C-21-epi derivatives of FK-506; a 31-demethylated derivative of FK-506; 31-oxo-FK-506; and compounds derived from FK-506, FR-900523 and FR-900525 which are characterized by the introduction of hydroxy-protecting groups, formation of a double bond by elimination of water between carbons 23 and 24, oxidation of the hydroxy group at carbon 24 to the ketone, and reduction of the allyl side-chain at carbon 21 via hydrogenation. Other published derivatives include those derived from FK-506 and FR-900520 where the lactone ring is contracted to give a macrocyclic ring containing two fewer carbons.

Several microbial transformations of FK-type compounds at carbon 13 have been published, such as the microbial demethylation of FR-900520 to form the bis-demethylated 13,31-dihydroxy ring-rearranged derivative of FR-900520; the microbial monodemethylation of FK-506 and FR-900520, respectively; and the microbial demethylation of FR-900520 at C-31, as well as a number of other macrocyclic microbial transformation products.

Numerous chemical modifications of the FK-type compounds have been attempted. These include the preparation of small synthetic fragments of FK-type derivatives; a thermal rearrangement of a variety of derivatives of FK-506 which expands the macrocyclic ring by two carbons; and modifications which include methyl ether and aryl ether formation at C-32 and/or C-24, oxidation of C-32 alcohol to the ketone, and epoxide formation at C-9.

Although some of these modified compounds exhibit immunosuppressive activity, the need remains for macrocyclic immunosuppressants which do not have the serious side effects frequently associated with immunosuppressant therapy. Accordingly, one object of the invention is to provide novel semisynthetic macrolides which possess the desired immunomodulatory activity but which minimize undesired side effects.

Another object of the present invention is to provide synthetic processes for the preparation of such compounds from starting materials obtained by fermentation, as well as chemical intermediates useful in such synthetic processes.

A further object of the invention is to provide pharmaceutical compositions containing, as an active ingredient, one of the above compounds. Yet another object of the invention is to provide a method of treating a variety of disease states, including post-transplant tissue rejection and autoimmune disfunction.

DISCLOSURE OF THE INVENTION

In accordance with the present invention there are compounds of the formula (I):

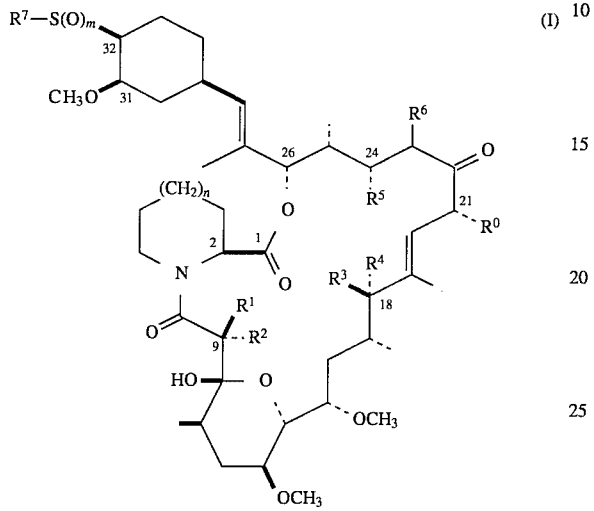

wherein n is zero or one;

m is zero, one or two;

$R^0$ is hydrogen, methyl, ethyl, allyl, propyl, 2-hydroxyethyl, cyclopropylmethyl, 2-oxopropyl or 2-ethanal;

$R^1$ and $R^2$ are independently hydrogen or hydroxy, subject to the proviso that when one of $R^1$ or $R^2$ is hydroxy, the other of $R^1$ and $R^2$ is hydrogen; or, alternatively, R 1 and $R^2$ taken together are oxo;

$R^3$ and $R^4$ are independently hydrogen, halogen, or hydroxy, subject to the proviso that when one of $R^3$ or $R^4$ is halogen or hydroxy, the other of $R^3$ and $R^4$ is hydrogen; or, alternatively, $R^3$ and $R^4$ taken together are oxo;

$R^5$ is hydrogen, hydroxy, or protected hydroxy, and $R^6$ is hydrogen; or alternatively, $R^5$ and $R^6$ taken together form a C-23/C-24 bond; and $R^7$ is selected from the group consisting of (a) —$L_1$—OH wherein $L_1$ is alkylene;

(b) —$L_3$—C(O)$R^8$ wherein $L_3$ is alkylene and $R^8$ is
 (i) —O—$R^9$ wherein $R^9$ is hydrogen, loweralkyl, haloalkyl, alkoxyalkyl, aminoalkyl, alkylaminoalkyl, dialkylaminoalkyl, hydroxyalkyl, arylalkyl, aryl, arylalkoxyalkyl, cycloalkyl, cycloalkylalkyl or sufonic acid-substituted alkyl;
 (ii) —N(OH)$R^{10}$ wherein $R^{10}$ is hydrogen or loweralkyl; or
 (iii) —NR$^{11}$R$^{12}$ wherein $R^{11}$ and $R^{12}$ are independently selected from hydrogen, loweralkyl, and cycloalkyl or $R^{11}$ and $R^{12}$ taken together with the nitrogen to which they are bonded from a heterocyclic ring selected from aziridinyl, azetidinyl, pyrrolidinyl, piperidinyl, piperazinyl, morpholinyl and thiomorpholinyl;

(c) —C(O)$R^{13}$ wherein $R^{13}$ is
 (i) heterocyclic,
 (ii) hydroxyalkyl,
 (iii) alkoxycarbonyl,
 (iv) —$L_4$—NR$^{14}$R$^{15}$ wherein $L_4$ is alkylene or hydroxy-substituted alkylene, $R^{14}$ is hydrogen or lower alkyl and $R^{15}$ is —C(O)—$R^{16}$ wherein $R^{16}$ is loweralkyl or —NH$_2$ or $R^{14}$ and $R^{15}$ taken together with the nitrogen atom to which they are bonded form a heterocyclic ring selected from aziridinyl, azetidinyl, pyrrolidinyl, piperidinyl, piperazinyl, morpholinyl and thiomorpholinyl;
 (v) —NR$^{17}$R$^{18}$ wherein $R^{17}$ is hydrogen or loweralkyl and $R^{18}$ is loweralkyl, aryl, arylalkyl, dialkoxyalkyl or —$L_5$—C(O)$R^{19}$ wherein $L_5$ is alkylene and $R^{19}$ is hydrogen, loweralkyl, cycloalkyl, aryl, arylalkyl, aziridinyl, azetidinyl, pyrrolidinyl, piperidinyl, piperazinyl, morpholinyl, thiomorpholinyl,—OH or (R$^{20}$)$_3$—Si—(CH$_2$)$_2$—wherein $R^{20}$ is loweralkyl;
 (vi) —OR$^{21}$ wherein $R^{21}$ is loweralkyl, aryl or arylalkyl; or
 (vii) —N(OR$^{17}$)R$^{18}$ wherein $R^{17}$ and $R^{18}$ are as defined above;
 with the proviso that when $R^7$ is —C(O)—$R^{13}$, m is 0;

(d) —C(=NH)NH$_2$ wherein m is 0;

(e) loweralkyl wherein m is 1 or 2;

(f) cycloalkyl;

(g) loweralkenyl;

(h) alkoxyalkyl;

(i) thioalkoxyalkyl;

(j) aryl wherein m is 1 or 2;

(k) arylalkyl wherein m is 1 or 2;

(l) —$L_6$—C(R$^{22}$)—R$^{23}$ wherein $L_6$ is alkylene, $R^{22}$ is =O or =N—R$^{24}$ wherein $R^{24}$ is —OH, alkoxy, or —NHC(O)NH$_2$, and $R^{23}$ is loweralkyl; and (m) hydroxy with the proviso that when $R^7$ is hydroxy, m is 2;

or a pharmaceutically acceptable salt, ester, amide or prodrug thereof.

Representative of some of the preferred compounds of the invention are those having the formula:

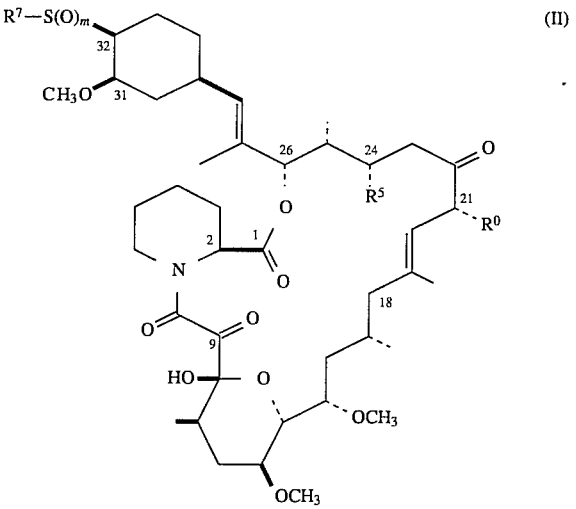

where m, $R^0$, $R^5$, and $R^7$ are as previously defined. Of these, particularly preferred compounds are those in which $R^0$ is ethyl, allyl or propyl; $R^5$ is selected from the group consisting of hydrogen and hydroxy. Those compounds in which $R^5$ is hydroxy and $R^0$ is ethyl are more preferred.

Preferred among the compounds of the present invention are compounds of formula II wherein $R^0$ is ethyl, allyl or propyl; $R^5$ is hydrogen or hydroxy; m is 0, 1 or 2; and $R^7$ is (a) —$L_1$—OH wherein $L_1$ is alkylene; (b) —$L_3$—C(O)$R^8$ wherein $L_3$ is alkylene and $R^8$ is (i) —O—$R^9$ wherein $R^9$ is hydrogen, loweralkyl, haloalkyl, alkoxyalkyl, aminoalkyl, alkylaminoalkyl, dialkylaminoalkyl, hydroxyalkyl, arylaalkyl, or aryl; (ii) —N(OH)$R^{10}$ wherein $R^{10}$ is hydrogen or loweralkyl; or (iii) —$NR^{11}R^{12}$ wherein $R^{11}$ and $R^{12}$ are independently selected from hydrogen and loweralkyl or $R^{11}$ and $R^{12}$ taken together with the nitrogen to which they are bonded form a heterocyclic ring selected from aziridinyl, azetidinyl, pyrrolidinyl, piperidinyl, piperazinyl, and morpholinyl; (c) —C(O)$R^{13}$ wherein $R^{13}$ is (i) heterocyclic, (ii) hydroxyalkyl, (iii) —$L_4$—$NR^{14}R^{15}$ wherein $L_4$ is alkylene or hydroxy-substituted alkylene, $R^{14}$ iS hydrogen or lower alkyl and $R^{15}$ is —C(O)—$R^{16}$ wherein $R^{16}$ is loweralkyl or —$NH_2$, or (iv) —$NR^{17}R^{18}$ wherein $R^{17}$ is hydrogen or loweralkyl and $R^{18}$ is loweralkyl, aryl, arylalkyl, dialkoxyalkyl or —$L_5$—C(O)$R^{19}$ wherein $L_5$ is alkylene and $R^{19}$ is hydrogen, loweralkyl, aziridinyl, azetidinyl, pyrrolidinyl, piperidinyl, piperazinyl, or morpholinyl; (d) loweralkyl wherein m is 1 or 2; (e) thioalkoxyalkyl; (f) aryl wherein m is 1 or 2; or (g) —$L_6$—C($R^{22}$)—$R^{23}$ wherein $L_6$ is alkylene, $R^{22}$ is =O or =N—$R^{24}$ wherein $R^{24}$ is —OH, alkoxy, or —$NHC(O)NH_2$, and $R^{23}$ is loweralkyl.

Particularly preferred among the compounds of the present invention are compounds of formula II wherein $R^0$ is ethyl, allyl or propyl; $R^5$ is hydrogen or hydroxy; m is 0, 1 or 2; and $R^7$ is (a) —$L_1$—OH wherein $L_1$ is alkylene; (b) —$L_3$—C(O)$R^8$ wherein $L_3$ is alkylene and $R^8$ is (i) -0 —$R^9$ wherein $R^9$ is loweralkyl, or haloalkyl; (ii) —N(OH)$R^{10}$ wherein $R^{10}$ is hydrogen or loweralkyl; or (iii) —$NR^{11}R^{12}$ wherein $R^{11}$ and $R^{12}$ are independently selected from hydrogen and loweralkyl or $R^{11}$ and $R^{12}$ taken together with the nitrogen to which they are bonded form a heterocyclic ring selected from aziridinyl, azetidinyl, pyrrolidinyl, piperidinyl, piperazinyl, and morpholinyl; (c) —C(O)$R^{13}$ wherein $R^{13}$ is (i) heterocyclic, (ii) hydroxyalkyl, (iii) —$L_4$—$NR^{14}R^{15}$ wherein $L_4$ is alkylene or hydroxy-substituted alkylene, $R^{14}$ is hydrogen or lower alkyl and $R^{15}$ is —C(O)—$R^{16}$ wherein $R^{16}$ is loweralkyl or (iv) —$NR^{17}R^{18}$ wherein $R^{17}$ is hydrogen or loweralkyl and $R^{18}$ is loweralkyl, aryl or —$L_5$—C(O)$R^{19}$ wherein $L_5$ is alkylene and $R^{19}$ is aziridinyl, azetidinyl, pyrrolidinyl, piperidinyl, piperazinyl, or morpholinyl; (d) loweralkyl wherein m is 1 or 2; (e) thioalkoxyalkyl; or (f) —$L_6$—C($R^{22}$)—$R^{23}$ wherein $L_6$ is alkylene, $R^{22}$ is =N—$R^{24}$ wherein $R^{24}$ is —$NHC(O)NH_2$, and $R^{23}$ is loweralkyl.

Especially preferred among the compounds of the present invention are compounds of formula II wherein $R^0$ is ethyl, allyl or propyl; $R^5$ is hydrogen or hydroxy; m is 0, 1 or 2; and $R^7$ is (a) —$L_1$—OH wherein $L_1$ is alkylene; (b) —$L_3$—C(O)$R^8$ wherein $L_3$ is alkylene and $R^8$ is (i) —N(OH)$R^{10}$ wherein $R^{10}$ is hydrogen or loweralkyl or (ii) —$NR^{11}R^{12}$ wherein $R^{11}$ and $R^{12}$ are independently selected from hydrogen and loweralkyl or $R^{11}$ and $R^{12}$ taken together with the nitrogen to which they are bonded form a morpholinyl ring; (c) —C(O)$R^{13}$ wherein $R^{13}$ is (i) heterocyclic, (ii) hydroxyalkyl, or (iii) —$L_4$—$NR^{14}R^{15}$ wherein $L_4$ is alkylene or hydroxy-substituted alkylene, $R^{14}$ is hydrogen or lower alkyl and $R^{15}$ is —C(O)—$R^{16}$ wherein $R^{16}$ is loweralkyl; (d) loweralkyl wherein m is 1 or 2; or (e) thioalkoxyalkyl.

Most preferred among the compounds of the present invention are compounds of formula II wherein $R^0$ is ethyl; $R^5$ is hydroxy; m is 0, 1 or 2; and $R^7$ is (a) —$L_1$—OH wherein $L_1$ is alkylene; (b) —$L_3$—C(O)$R^8$ wherein $L_3$ is alkylene and $R^8$ is (i) —N(OH)$R^{10}$ wherein $R^{10}$ is hydrogen or loweralkyl or (ii) —$NR^{11}R^{12}$ wherein $R^{11}$ and $R^{12}$ are independently selected from hydrogen and loweralkyl or $R^{11}$ and $R^{12}$ taken together with the nitrogen to which they are bonded form a morpholinyl ring; (c) —C(O)$R^{13}$ wherein $R^{13}$ is (i) heterocyclic, (ii) hydroxyalkyl, or (iii) —$L_4$—$NR^{14}R^{15}$ wherein $L_4$ is alkylene or hydroxy-substituted alkylene, $R^{14}$ is hydrogen or lower alkyl and $R^{15}$ is —C(O)—$R^{16}$ wherein $R^{16}$ is loweralkyl; (d) loweralkyl wherein m is 1 or 2; or (e) thioalkoxyalkyl.

The present invention also relates to processes for preparing the compounds of formula (I) and (II) and to the synthetic intermediates, including the compounds of formula (III) and (IV), employed in these processes.

The present invention also relates to a method of immunosuppression in a mammal in need of such treatment, comprising administering to the mammal a therapeutically effective amount of a compound of formula (I) or (II).

The invention further relates to immunosuppressing compositions comprising a pharmaceutical carrier and a therapeutically effective amount of a compound of formula (I) or (II).

The compounds of the invention comprise two or more asymmetrically substituted carbon atoms. As a result, all stereoisomers (for example, racemic mixtures, mixtures of diastereomers, as well as single diastereomers) of the compounds of the invention are included in the present invention. The terms "S" and "R" configuration are as defined by the IUPAC 1974 Recommendations for Section E, Fundamental Stereochemistry, Pure Appl. Chem. (1976) 45, 13–30.

As used throughout this Specification and Claims, the following terms have the meanings specified:

The terms "loweralkyl" or "alkyl" as used herein refer to straight or branched chain alkyl radicals containing from 1 to 10 carbon atoms including, but not limited to, methyl, ethyl, n-propyl, iso-propyl, n-butyl, iso-butyl, sec-butyl, t-butyl, n-pentyl, 1-methylbutyl, 2,2-dimethylbutyl, 2-methylpentyl, 2,2-dimethylpropyl, n-hexyl and the like.

The term "loweralkenyl" as used herein refers to a monovalent straight or branched chain radical of 2 to 10 carbon atoms containing at least one carbon-carbon double bond including, but not limited to ethenyl, 1-propenyl, 2-propenyl, 2-methyl-1-propenyl, 1-butenyl and 2-butenyl.

The term "alkynyl" as used herein refers to a monovalent straight or branched chain radical of 2 to 10 carbon atoms containing at least one carbon-carbon triple bond including, but not limited to ethynyl, butynyl and pentynyl.

The term "alkoxy" as used herein refers to $R_{41}O$— wherein $R_{41}$ is a loweralkyl group, as defined above. Examples of alkoxy include, but are not limited to, ethoxy, tert-butoxy, and the like.

The term "alkylene" denotes a divalent group derived from a straight or branched chain saturated hydrocarbon having from 1 to 10 carbon atoms by the removal of two hydrogen atoms, for example methylene, 1,2-ethylene, 1,1-ethylene, 1,3-propylene, 2,2-dimethylpropylene, and the like.

The term "alkoxyalkoxy" as used herein refers to $R_{91}$—O—$R_{92}$-O- wherein $R_{91}$ is loweralkyl and $R_{92}$ is alkylene. Examples of alkoxyalkoxy include methoxymethox, methoxyethoxy and the like.

The term "alkoxyalkyl" as used herein refers to $R_{80}O$—$R_{81}$—wherein $R_{80}$ is loweralkyl as defined above and $R_{81}$ is alkylene. Representative examples of alkoxyalkyl groups include methoxymethyl, ethoxymethyl, t-butoxymethyl and the like.

The term "dialkoxyalkyl" as used herein refers to a lower alkyl radical, as defined above, bearing two alkoxy groups. Examples of dialkoxyalkyl include 1,2-dimethoxyethyl, 1,3-dimethoxypropyl and the like.

The term "alkoxycarbonyl" as used herein refers to $R_{90}$—C(O)—wherein $R_{90}$ is an alkoxy group. Examples of alkoxycarbonyl include methoxycarbonyl, ethoxycarbonyl and the like.

The term "alkylamino" as used herein refers to $R_{51}N$—wherein $R_{51}$ is loweralkyl, for example ethylamino, methylamino, and the like.

The term "alkylaminoalkyl" as used herein refers to $R_{56}NH$—$R_{57}$—wherein $R_{56}$ is a loweralkyl group and $R_{57}$ is an alkylene group. Examples of alkylaminoalkyl include ethylaminomethyl, butylaminomethyl, and the like.

The term "dialkylaminoalkyl" as used herein refers to $R_{71}R_{72}N$—$R_{73}$—wherein $R_{71}$ and $R_{72}$ are independently selected from loweralkyl and $R_{73}$ is an alkylene group. Examples of dialkylaminoalkyl include dimethylaminomethyl, dimethylaminoethyl, N-ethyl—N-methylaminomethyl, and the like.

The term "alkylene" denotes a divalent group derived from a straight or branched chain saturated hydrocarbon having from 1 to 10 carbon atoms by the removal of two hydrogen atoms, for example methylene, 1,2-ethylene, 1,1-ethylene, 1,3-propylene, 2,2-dimethylpropylene, and the like.

The term "aminoalkyl" as used herein refers to a loweralkyl radical to which is appended an amino (—NH$_2$) group. Examples of aminoalkyl include aminomethyl, 2-aminoethyl and the like.

The term "aryl" as used herein refers to a mono- or bicyclic carbocyclic ring system having one or more aromatic rings including, but not limited to, phenyl, naphthyl, tetrahydronaphthyl, indanyl, indenyl and the like. The term "bicyclic aryl" as used herein includes naphthyl, tetrahydronaphthyl, 1,2-dihydronaphthyl, indanyl, indenyl and the like. Aryl groups (including bicyclic aryl groups) can be unsubstituted or substituted with one, two or three substituents independently selected from loweralkyl, haloalkyl, alkoxy, thioalkoxy, amino, alkylamino, dialkylamino, hydroxy, halo, mercapto, nitro, carboxaldehyde, carboxy, alkoxycarbonyl, cyano, alkyl—C(O)—O—, alkyl—C(O)—NH—, and carboxamide. In addition, substituted aryl groups include tetrafluorophenyl and pentafluorophenyl.

The term "arylalkoxyalkyl" as used herein refers to $R_{42}O$—$R_{43}$—wherein $R_{42}$ is an arylalkyl group and $R_{43}$ is an alkylene group. Examples of arylalkoxyalkyl include benzyloxymethyl, and the like.

The term "arylalkyl" as used herein refers to an aryl group as previously defined, appended to a loweralkyl radical, for example, benzyl and the like.

The term "cycloalkyl" as used herein refers to an aliphatic ring system having 3 to 10 carbon atoms and 1 to 3 rings including, but not limited to, cyclopropyl, cyclopentyl, cyclohexyl, norbornyl, adamantyl, and the like. Cycloalkyl groups can be unsubstituted or substituted with one, two or three substituents independently selected from loweralkyl, haloalkyl, alkoxy, thioalkoxy, amino, alkylamino, dialkylamino, hydroxy, halo, mercapto, nitro, carboxaldehyde, carboxy, alkoxycarbonyl and carboxamide.

The term "cycloalkylalkyl" as used herein refers to a cycloalkyl group appended to a loweralkyl radical, including but not limited to cyclohexylmethyl.

The term "halogen" or "halo" as used herein refers to I, Br, Cl or F.

The term "haloalkyl" as used herein refers to a lower alkyl radical, as defined above, bearing at least one halogen substituent, for example, chloromethyl, fluoroethyl or trifluoromethyl and the like.

The terms "heterocyclic ring" or "heterocyclic" or "heterocycle" as used herein refers to any 3- or 4-membered ring containing a heteroatom selected from oxygen, nitrogen and sulfur; or a 5-, 6- or 7-membered ring containing one, two or three nitrogen atoms; one oxygen atom; one sulfur atom; one nitrogen and one sulfur atom; one nitrogen and one oxygen atom; two oxygen atoms in non-adjacent positions; one oxygen and one sulfur atom in non-adjacent positions; or two sulfur atoms in non-adjacent positions. As used herein "heterocyclic" also includes 1,3,4-oxadiazole, 1,3,4-thiadiazole, 1,3,5-oxadiazole, 1,3,5-thiadiazole and tetrazole. The 5-membered ring has 0-2 double bonds and the 6- and 7-membered ring have 0-3 double bonds. The nitrogen heteroatoms can be optionally quaternized. The term "heterocyclic" also includes bicyclic groups in which any of the above heterocyclic rings is fused to a benzene ring or a cyclohexane ring or another heterocyclic ring (for example, indolyl, quinolyl, isoquinolyl, tetrahydroquinolyl, decahydroquinolyl, benzofuryl or benzothienyl, imidazopyridyl, pyrrolopyridyl and the like). The term "heterocyclic" also includes tricyclic groups in which any of the above heterocyclic rings is fused to two benzene rings or two cyclohexane rings or two other heterocyclic rings (for example, carbazolyl, iminodibenzyl and the like). Heterocyclics include: azetidinyl, aziridinyl, benzimidazolyl, 1,4-benzodioxanyl, 1,3-benzodioxolyl, benzoxazolyl, benzothiazolyl, benzothienyl, carbazolyl, dihydropyranyl, dihydrofuranyl, dioxanyl, dioxolanyl, furyl, homopiperidinyl, imidazolyl, imidazolinyl, imidazolidinyl, imidazopyridyl, iminodibenzyl, indolinyl, indolyl, isoquinolinyl, isothiazolidinyl, isothiazolyl, isoxazolidinyl, isoxazolyl, morpholinyl, naphthyridinyl, oxazolidinyl, oxazolyl, oxetanyl, piperazinyl, piperidinyl, pyranyl, pyrazinyl, pyrazolidinyl, pyrazolinyl, pyrazolyl, pyridazinyl, pyridyl, pyrimidinyl, pyrrolidinyl, pyrrolindinylpyridyl, pyrrolinyl, pyrrolopyridyl, pyrrolyl, quinolinyl, tetrahydrofuranyl, tetrahydropyranyl, thiazolidinyl, thiazolyl, and thienyl.

Heterocyclics can be unsubstituted or monosubstituted or disubstituted with substituents independently selected from hydroxy, halo, oxo (=O), alkylimino (RN= wherein R is a loweralkyl group), amino, alkylamino, dialkylamino, alkoxy, alkoxyalkoxy, haloalkyl, cycloalkyl, aryl, arylalkyl, —COOH, —SO$_3$H and loweralkyl. In addition, nitrogen containing heterocycles can be N-protected.

The term "hydroxyalkyl" as used herein refers to a lower alkyl radical, as defined above, bearing at least one —OH substituent, for example, hydroxymethyl, 2-hydroxyethyl and the like.

The term "oxo" as used herein refers to =O.

The term "sulfonic acid-substituted alkyl" as used herein refers to a lower alkyl radical to which is appended a sulfonic acid group (—S(O)$_3$H).

The term "thioalkoxy" as used herein refers to $R_{70}S$—wherein $R_{70}$ is loweralkyl. Examples of thioalkoxy include, but are not limited to, methylthio, ethylthio and the like.

The term "thioalkoxyalkyl" as used herein refers to $R_{70}S$—$R_{71}$—wherein $R_{70}$ is loweralkyl and $R_{71}$ is alkylene. Examples of thioalkoxyalkyl include, but are not limited to, methylthiomethyl, ethylthiomethyl and the like.

The term "hydroxy-protecting group" as used herein refers to those radicals which are known in the art of organic synthesis (T. W. Greene and P. G. M. Wuts, Protective Groups in Organic Synthesis, 2nd ed., John Wiley & Son, Inc., 1991 which is incorporated herein by reference) to protect a hydroxyl group against undesirable reaction during synthetic procedures and to be selectively removable. Examples include, but are not limited to, methylthiomethyl, dimethylthexylsilyl, trisubstituted silyl such as tris(loweralkyl)silyl (e.g., trimethylsilyl, triethylsilyl, tributylsilyl, triisopropylsilyl, tert-butyldimethylsilyl, tri-tert-butylsilyl, triphenylsilyl, triphenylmethyldimethylsilyl, and the like); loweralkyldiarylsilyl (e.g., methyldiphenylsilyl, ethyldiphenylsilyl, propyldiphenylsilyl, tertbutyldiphenylsilyl, and the like); triarylsilyl (e.g., triphenylsilyl, trixylylsilyl, and the like); triarylalkylsilyl (e.g., tribenzylsilyl, and the like); alkyl—C(O)—(e.g., acetyl and the like); aryloyl (e.g., benzoyl and the like); alkoxycarbonyl (e.g., ethoxycarbonyl and the like); —S(O)$_2$-(loweralkyl); and —S(O)$_2$-(aryl).

The term "protected hydroxy" as used herein refers to a hydroxy group to which has been attached a hydroxy-protecting group, as defined above.

The term "N-protecting group" or "N-protected" as used herein refers to those groups intended to protect the N-terminus of an amino acid or peptide or to protect an amino group against undersirable reactions during synthetic procedures. Commonly used N-protecting groups are disclosed in Greene, "Protective Groups In Organic Synthesis," (John Wiley & Sons, New York (1981)), which is hereby incorporated by reference. N-protecting groups comprise acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)- 1-methylethoxycarbonyl, α,α-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl and the like; alkyl groups such as benzyl, triphenylmethyl, benzyloxymethyl and the like; and silyl groups such as trimethylsilyl and the like. Preferred N-protecting groups are formyl, acetyl, benzoyl, pivaloyl, t-butylacetyl, phenylsulfonyl, benzyl, t-butyloxycarbonyl (Boc) and benzyloxycarbonyl (Cbz).

The term "carboxy protecting group" as used herein refers to a carboxylic acid protecting ester group employed to block or protect the carboxylic acid functionality while the reactions involving other functional sites of the compound are carried out. Carboxy protecting groups are disclosed in Greene, "Protective Groups in Organic Synthesis" pp. 152–186 (1981), which is hereby incorporated herein by reference. In addition, a carboxy protecting group can be used as a prodrug whereby the carboxy protecting group can be readily cleaved in vivo, for example by enzymatic hydrolysis, to release the biologically active parent. T. Higuchi and V. Stella provide a thorough discussion of the prodrug concept in "Pro-drugs as Novel Delivery Systems", Vol 14 of the A.C.S. Symposium Series, American Chemical Society (1975), which is hereby incorporated herein by reference. Such carboxy protecting groups are well known to those skilled in the art, having been extensively used in the protection of carboxyl groups in the penicillin and cephalosporin fields, as described in U.S. Pat. Nos. 3,840,556 and 3,719,667, the disclosures of which are hereby incorporated herein by reference. Examples of esters useful as prodrugs for compounds containing carboxyl groups can be found on pages 14–21 of "Bioreversible Carriers in Drug Design: Theory and Application", edited by E. B. Roche, Pergamon Press, New York (1987), which is hereby incorporated herein by reference. Representative carboxy protecting groups are $C_1$ to $C_8$ loweralkyl (e.g., methyl, ethyl or tertiary butyl and the like); arylalkyl, for example, phenethyl or benzyl and substituted derivatives thereof such as alkoxybenzyl or nitrobenzyl groups and the like; arylalkenyl, for example, phenylethenyl and the like; aryl and substituted derivatives thereof, for example, 5-indanyl and the like; dialkylaminoalkyl (e.g., dimethylaminoethyl and the like); alkanoyloxyalkyl groups such as acetoxymethyl, butyryloxymethyl, valeryloxymethyl, isobutyryloxymethyl, isovaleryloxymethyl, 1-(propionyloxy)-1-ethyl, 1-(pivaloyloxy)-1-ethyl, 1-methyl-1-(propionyloxy)-1-ethyl, pivaloyloxymethyl, propionyloxymethyl and the like; cycloalkanoyloxyalkyl groups such as cyclopropylcarbonyloxymethyl, cyclobutylcarbonyloxymethyl, cyclopentylcarbonyloxymethyl, cyclohexylcarbonyloxymethyl and the like; aroyloxyalkyl, such as benzoyloxymethyl, benzoyloxyethyl and the like; arylalkylcarboonyloxyalkyl, such as benzylcarbonyloxymethyl, 2-benzylcarbonyloxyethyl and the like; alkoxycarbonylalkyl, such as methoxycarbonylmethyl, cyclohexyloxycarbonylmethyl, 1-methoxycarbonyl-1-ethyl, and the like; alkoxycarbonyloxyalkyl, such as methoxycarbonyloxymethyl, t-butyloxycarbonyloxymethyl, 1-ethoxycarbonyloxy-1-ethyl, 1-cyclohexyloxycarbonyloxy-1-ethyl and the like; alkoxycarbonylaminoalkyl, such as t-butyloxycarbonylaminomethyl and the like; alkylaminocarbonylaminoalkyl, such as methylaminocarbonylaminomethyl and the like; alkanoylaminoalkyl, such as acetylaminomethyl and the like; heterocycliccarbonyloxyalkyl, such as 4-methylpiperazinylcarbonyloxymethyl and the like; dialkylaminocarbonylalkyl, such as dimethylaminocarbonylmethyl, diethylaminocarbonylmethyl and the like; (5-(loweralkyl)-2-oxo-1,3-dioxolen-4-yl)alkyl, such as (5-t-butyl-2-oxo-1,3-dioxolen-4-yl)methyl and the like; and (5-phenyl-2-oxo-1,3-dioxolen-4-yl)alkyl, such as (5-phenyl-2-oxo-1,3-dioxolen-4-yl)methyl and the like.

"Pharmaceutically acceptable salts, esters, amides and prodrugs" refers to those salts, esters, amides and prodrugs of the compounds of the present invention which are, within the scope of sound medical judgement, suitable for use in contact with the tissues of humans and lower animals without undue toxicity, irritation, allergic response, or the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention, which may be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate and laurylsulphonate salts and the like. These may include cations based on the alkali and alkaline earth metals, such as sodium, lithium, potassium, calcium, magnesium and the like, as well as nontoxic ammonium, quaternary ammonium and amine cations including, but not limited to, ammonium, tetramethylammonium, tetraethylammonium, methylamine, dimethylamine, trimethylamine, triethylamine, ethylamine, and the like (see, for example S. M. Berge, et al., "Pharmaceutical Salts," *J. Pharm. Sci.*, 66:1–19 (1977) which is incorporated herein by reference).

Examples of pharmaceutically-acceptable, non-toxic esters of the compounds of this invention include $C_1$-to-$C_6$-alkyl esters wherein the alkyl group is a straight or branched chain. Acceptable esters also include $C_5$-to-$C_7$-cycloalkyl esters as well as arylalkyl esters such as, but not limited to benzyl. $C_1$-to-$C_4$ alkyl esters are preferred. Esters of the compounds of the present invention may be prepared according to conventional methods. Conversely, non-toxic esters of alcoholic moieties on the compounds of the invention may be constructed by condensing these alcohols with $C_1$-to-$C_6$-alkyl carboxylic acids, $C_1$-to-$C_6$-alkyl dicarboxylic acids or aryl-carboxylic acids. Examples of such esters include, but are not limited to acetyl, benzoyl or hemisuccinyl.

Examples of pharmaceutically-acceptable, non-toxic amides of the compounds of this invention include amides derived from ammonia, primary $C_1$-to-$C_6$-alkyl amines and secondary di—Cl-to-$C_6$-alkyl amines. In the case of secondary amines the amine may also be in the form of a 5-or-6 membered heterocycle containing one nitrogen atom. Amides derived from ammonia, $C_1$-to-$C_3$-alkyl primary amides and di—C1-to-C2-alkyl secondary amides are preferred. Amides of the compounds of the invention may be prepared according to conventional methods.

"Prodrug" refers to compounds that are rapidly transformed in vivo to yield the parent compound of the above formula, for example, by hydrolysis in blood. A thorough discussion is provided in T. Higuchi and V. Stella, "Prodrugs as Novel Delivery Systems", Vol 14 of the A.C.S. Symposium Series, and in *Bioreversible Carriers in Drug Design*, ed. Edward B. Roche, American Pharmaceutical Association and Pergamon Press, 1987 both of which are incorporated herein by reference.

Prodrugs of compounds of the present invention may be prepared by suitable methods. For those compounds in which the prodrug moiety is an amino acid or peptide functionality, the condensation of the drug's amino group with amino acids and peptides may be effected in accordance with conventional condensation methods such as the azide method, the mixed acid anhydride method, the DCC (dicyclohexylcarbodiimide) method, the active ester method (p-nitrophenyl ester method, N-hydroxysuccinic acid imide ester method, cyanomethyl ester method and the like), the Woodward reagent K method, the DCC-HOBT (1-hydroxybenzotriazole) method and the like. Classical methods for amino acid condensation reactions are described in "Peptide Synthesis" Second Edition, M. Bodansky, Y. S. Klausner and M. A. Ondetti (1976).

As in conventional peptide synthesis, branched chain amino and carboxyl groups at alpha and omega positions in amino acids may be protected and deprotected if necessary. The protecting groups for amino groups which can be used involve, for example, benzyloxycarbonyl (Z or Cbz), o-chlorobenzyloxycarbonyl ((2—Cl)Z)), p-nitrobenzyloxycarbonyl (Z($NO_2$)), p-methoxybenzyloxycarbonyl (Z(OMe)), t-amyloxycarbonyl (Aoc), isobornealoxycarbonyl, adamantyloxycarbonyl (Adoc), 2-(4-biphenyl)-2-propyloxy carbonyl (Bpoc), 9-fluorenyl-methoxycarbonyl (Fmoc), methylsulfonylethoxy carbonyl (Msc), trifluoroacetyl, phthalyl, formyl, 2-nitrophenylsulfonyl (Nps), diphenylphosphinothioyl (Ppt), dimethylphosphinothioyl (Mpt), and the like.

The examples for protecting groups for carboxyl groups involve, for example, benzyl ester (OBzl), cyclohexyl ester, 4-nitrobenzyl ester (OBzl$NO_2$), t-butyl ester (OtBu), 4-pyridylmethyl ester (OPic), and the like.

In the course of the synthesis of certain of the compounds of the present invention, specific amino acids having functional groups other than amino and carboxyl groups in the branched chain such as arginine, cysteine, serine and the like may be protected, if necessary, with suitable protecting groups. It is preferable that, for example, the guanidino group (NG) in arginine may be protected with nitro, p-toluenesulfonyl (Tos), benzyloxycarbonyl (Z), adamantyloxycarbonyl (Adoc), p-methoxybenzenesulfonyl, 4-methoxy-2, 6-dimethyl-benzenesulfonyl (Mts) and the like; the thiol group in cysteine may be protected with benzyl, p-methoxybenzyl, triphenylmethyl, acetamidomethyl, ethylcarbamyl, 4-methylbenzyl (4-MeBzl), 2,4,6-trimethylbenzyl (Tmb) and the like; and the hydroxy group in serine may be protected with benzyl (Bzl), t-butyl, acetyl, tetrahydropyranyl (THP), and the like.

Representative compounds of the invention include:

Formula II: $R^0$=ethyl; $R^5$=—OH; m=0; $R^7$=—$CH_2$—$CH_2$—$CO_2$-Phenyl;

Formula II: $R^0$=ethyl; $R_5$=—OH; m=0; $R^7$=—$CH_2$—$CH_2$—$CO_2CH_3$;

Formula II: $R^0$=ethyl; $R_5$=—OH; m=0; $R^7$=—$CH_2$—$CH_2$—$CO_2CH_2CH_3$;

Formula II: $R^0$=ethyl; $R^5$=—OH; m=0; $R^7$=—$CH_2$—$CH_2$—$CO_2CH_2CH_2OCH_3$;

Formula II: $R^0$=ethyl; $R^5$=—OH; m=0; $R^7$=—$CH_2$—$CH_2$—$CO_2CH_2CF_3$;

Formula II: $R^0$=ethyl; $R^5$=—OH; m=0; $R^7$=—$CH_2$—$CH_2$—$CO\ _2CH_2CH_2OH$;

Formula II: $R^0$=ethyl; $R^5$=—OH; m=0; $R^7$=—$CH_2$—$CH_2$—$CO_2$Cyclohexyl;

Formula II: $R^0$=ethyl; $R^5$=—OH; m=0; $R^7$=—$CH_2$—$CH_2$—$CO_2$ tert-Butyl;

Formula II: $R^0$=ethyl; $R^5$=—OH; m=0; $R^7$=—$CH_2$—$CH_2$—$CO_2CH_2CH_2N(CH_3)_2$;

Formula II: $R^0$=ethyl; $R^5$=—OH; m=0; $R_7$=—$CH_2$—$CH_2$—$CO_2CH_2CH_2CH_2SO_3K$;

Formula II: $R^0$=ethyl; $R^5$=—OH; m=0; $R_7$=—$CH_2$—$CH_2$—$CO_2$Benzyl;

Formula II: $R^0$=ethyl; $R^5$=—OH; m=0; $R_7$=—$CH_2$—$CH_2$—$CO_2H$;

Formula II: $R_0$=ethyl; $R^5$=—OH; m=0; $R^7$=—$CH_2$—$CH_2$—$CO_2CH(CH_3)_2$;

Formula II: $R_0$=ethyl; $R^5$=—OH; m=0; $R^7$=—$CH_2$—$CH_2$—$CO_2CH(C_2H_5)_2$;

Formula II: $R^0$=ethyl; $R^5$=—OH; m=0;$R^7$=—$CH_2$—$CH_2$—$CONH_2$;

Formula II: $R^0$=ethyl; $R^5$=—OH; m =0;$R^7$=—$CH_2$—$CH_2$—CO-(4-morpholinyl);

Formula II: $R^0$=ethyl; $R^5$=—OH; m =0;$R^7$=—$CH_2$—$CH_2$—CONHOH;

Formula II: $R^0$=ethyl; $R^5$=—OH; m =0;$R^7$=—$CH_2$—$CH_2$—CON($CH_3$)OH;

Formula II: $R^0$=ethyl; $R^5$=—OH; m=0; $R^7$=—$CH_2$—$CH_2$—CO—N(OH)CH($CH_3$)$_2$;

Formula II: $R^0$=ethyl; $R^5$=—OH; m=0; $R^7$=—$CH_2$—$CH_2$—$CO_2$-Benzyl;

Formula II: $R^0$=ethyl; $R^5$=—OH; m=0;$R^7$=—$CH_2$—$CO_2$—$CH_3$;

Formula II: $R^0$=ethyl; $R^5$=—OH; m=0;$R^7$=—$CH_2$—$CO_2$—C($CH_3$)$_3$;

Formula II: $R^0$=ethyl; $R^5$=—OH; m=0;$R^7$=—$CH_2$—$CO_2H$;

Formula II: $R^0$=ethyl; $R^5$=—OH; m=0;$R^7$=—$CH_2$—$CO_2$—$CH_2CH_3$;

Formula II: $R^0$=ethyl; $R^5$=—OH; m=0;$R^7$=—$CH_2$—$CO_2CH(CH_3)_2$;

Formula II: $R^0$=ethyl; $R^5$=—OH; m=0;$R^7$=—$CH_2$—$CO_2CH_2CF_3$;

Formula II: $R^0$=ethyl; $R^5$=—OH; m=0;$R^7$=—$CH_2$—$CO_2CH_2CH_2OH$;

Formula II: $R^0$=ethyl; $R^5$=—OH; m=0;$R^7$=—$CH_2$—$CO_2CH_2CH_2OCH_3$;

Formula II: $R^0$=ethyl; $R^5$=—OH; m=0;$R^7$=—$CH_2CO_2CH_2CH_2N(CH_3)_2$;

Formula II: $R^0$=ethyl; $R^5$=—OH; m=0;$R^7$=—$CH_2$—$CO_2CH_2CH_2O$Benzyl; Formula II: $R^0$=ethyl; $R^5$=—OH; m=0;—$CH_2$—CONHOH;

Formula II: $R^0$=ethyl; $R^5$=—OH; m=0;$R^7$=—$CH_2$—$CONCH_3OH$;

Formula II: $R^0$=ethyl; $R^5$=—OH; m=0;$R^7$=—$CH_2$—$CH(CH_3)$—$CO_2CH_3$;

Formula II: $R^0$=ethyl; $R^5$=—OH; m=0;$R^7$=—$CH_2$—$CH(CH_3)$—$CO_2CH_2CH_3$;

Formula II: $R^0$=ethyl; $R^5$=—OH; m=0;$R^7$=—$CH_2$—$CH(CH_3)$—$CO_2$Benzyl;

Formula II: $R^0$=ethyl; $R^5$=—OH; m=0;$R^7$=—$CH_2$—$CH(CH_3)$—$CO_2H$;

Formula II: $R^0$=ethyl; $R^5$=—OH; m=0;$R^7$=—$CH_2CH_2OH$;

Formula II: $R^0$=ethyl; $R^5$=—OH; m=0;$R^7$=—$CH_2$—$CH_2$—OH;

Formula II: $R^0$=ethyl; $R^5$=—OH; m=0;$R^7$=—$CH_2$—$CH_2$—(4-Hydroxyphenyl);

Formula II: $R^0$=ethyl; $R^5$=—OH; m=1;$R^7$=—(4Hydroxyphenyl);

Formula II: $R^0$=ethyl; $R^5$=—OH; m=2;$R^7$=-(4-Hydroxyphenyl);

Formula II: $R^0$=ethyl; $R^5$=—OH; m=1;$R^7$=—$CH_2CH_2OH$;

Formula II: $R^0$=ethyl; $R^5$=—OH; m=1;$R^7$=—$CH_2CH_2OH$;

Formula II: $R^0$=ethyl; $R^5$=—OH; m=2;$R^7$=—$CH_2CH_2CH_2OH$;

Formula II: $R^0$=ethyl; $R^5$=—OH; m=1;$R^7$=—$CH_2CH_2CH_2OH$;

Formula II: $R^0$=ethyl; $R^5$=—OH; m=2;$R^7$=—$CH_2CH_2CH_2OH$;

Formula II: $R^0$=ethyl; $R^5$=—OH; m=1;$R^7$=—$CH_2CO_2$Benzyl;

Formula II: $R^0$=ethyl; $R^5$=—OH; m=1;$R^7$=—$CH_2CO_2$Benzyl;

Formula II: $R^0$=ethyl; $R^5$=—OH; m=2;$R^7$=—$CH_2CO_2$Benzyl;

Formula II: $R^0$=ethyl; $R^5$=—OH; m=2;$R^7$=—$CH_2CO_2CH_3$;

Formula II: $R^0$=ethyl; $R^5$=—OH; m=2;$R^7$=—$CH_2CO_2C(CH_3)_3$;

Formula II: $R^0$=ethyl; $R^5$=—OH; m=2;$R^7$=—$CH_2CO_2CH_2CH_3$;

Formula II: $R^0$=ethyl; $R^5$=—OH; m=1;$R^7$=—$CH_2CO_2CH_2CH_3$;

Formula II: $R^0$=ethyl; $R^5$=—OH; m=2;$R^7$=—$CH_2CO_2CH_2CH_3$;

Formula II: $R^0$=ethyl; $R^5$=—OH; m=1;$R^7$=—$CH_2CH_2CO_2$Benzyl;

Formula II: $R^0$=ethyl; $R^5$=—OH; m=1;$R^7$=—$CH_2CH_2CO_2$Benzyl;

Formula II: $R^0$=ethyl; $R^5$=—OH; m=2;$R^7$=—$CH_2CH_2CO_2$Benzyl;

Formula II: $R^0$=ethyl; $R^5$=—OH; m=1;$R^7$=—$CH_2CH_2CO_2CH(CH_3)_2$;

Formula II: $R^0$=ethyl; $R^5$=—OH; m=1;$R^7$=—$CH_2CH_2CO_2CH(CH_3)_2$;

Formula II: $R^0$=ethyl; $R^5$=—OH; m=1;$R^7$=—$CH_2CH_2CO_2CH(CH_2CH_3)_2$;

Formula II: $R^0$=ethyl; $R^5$=—OH; m=1;$R^7$=—$CH_2CH_2CO_2CH(CH_2CH_3)_2$;

Formula II: $R^0$=ethyl; $R^5$=—OH; m=1;$R^7$=—$CH_2CH_2CON(OH)CH_3$;

Formula II: $R^0$=ethyl; $R^5$=—OH; m=1;$R^7$=—$CH_2CH_2CON(OH)CH_3$;

Formula II: $R^0$=ethyl; $R^5$=—OH; m=1;$R^7$=—$CH_2CH_2CON(OH)CH(CH_3)_2$;

Formula II: $R^0$=ethyl; $R^5$=—OH; m=1;$R^7$=—$CH_2CH_2CON(OH)CH(CH_3)_2$;

Formula II: $R^0$=ethyl; $R^5$=—OH; m=1;$R^7$=—$CH_2CO_2H$;

Formula II: $R^0$=ethyl; $R^5$=—OH; m=1;$R^7$=—$CH_2CO_2H$;

Formula II: $R^0$=ethyl; $R^5$=—OH; m=2;$R^7$=—$CH_2CO_2H$;

Formula II: $R^0$=ethyl; $R^5$=—OH; m=1;$R^7$=—$CH_2CH_2CO_2H$;

Formula II: $R^0$=ethyl; $R^5$=—OH; m=1;$R^7$=—$CH_2CH_2CO_2H$;

Formula II: $R^0$=ethyl; $R^5$=—OH; m=2;$R^7$=—$CH_2CH_2CO_2H$;

Formula II: $R^0$=ethyl; $R^5$=—OH; m=0;$R^7$=-Allyl;

Formula II: $R^0$=ethyl; $R^5$=—OH; m=0;$R^7$=—$CH_2$—C(O)—$CH_3$;

Formula II: $R^0$=ethyl; $R^5$=—OH; m=0; $R^7$=—$CH_2$—$(CH_3)C$=N—NH—C(O)—$NH_2$;

Formula II: $R^0$=ethyl; $R^5$=—OH; m=0;$R^7$=—$CH_2$—$(CH_3)C$=N—O—$CH_3$;

Formula II: $R^0$=ethyl; $R^5$=—OH; m=0;$R^7$=—$CH_2$—$(CH_3)C$=N—OH;

Formula II: $R^0$=ethyl; $R^5$=—OH; m=2;$R^7$=—OH;

Formula II: $R^0$=ethyl; $R^5$=—OH; m=0;$R^7$=—C(O)—NH—$CH_2CH_3$;

Formula II: $R^0$=ethyl; $R^5$=—OH; m=0;$R^7$=—C(O)—NH—$CH_2CH_2CH_3$;

Formula II: $R^0$=ethyl; $R^5$=—OH; m=0;$R^7$=—C(O)—NH—$CH(CH_3)_2$;

Formula II: $R^0$=ethyl; $R^5$=—OH; m=0;$R^7$=—C(O)—NH—Phenyl;

Formula II: $R^0$=ethyl; $R^5$=—OH; m=0;$R^7$=—C(O)—NH—$CH_2$—$CO_2CH_2CH_3$;

Formula II: $R^0$=ethyl; $R^5$=—OH; m=0;$R^7$=—C(O)—$N(CH_3)_2$;

Formula II: $R^0$=ethyl; $R^5$=—OH; m=0;$R^7$=—C(O)—$N(CH_2CH_3)_2$;

Formula II: $R^0$=ethyl; $R^5$=—OH; m=0;$R^7$=—C(O)-(4-Morpholinyl);

Formula II: $R^0$=ethyl; $R^5$=—OH; m=0; $R^7$=—C(O)—$NHCH_2CO_2CH_2$(4-Methoxyphenyl);

Formula II: $R^0$=ethyl; $R^5$=—OH; m=0; $R^7$=—C(O)—$NHCH_2CO_2CH_2CH_2Si(CH_3)_3$;

Formula II: $R^0$=ethyl; $R^5$=—OH; m=0; $R^7$=—C(O)—NHCH$_2$C(O)-(4-Morpholinyl);
Formula II: $R^0$=ethyl; $R^5$=—OH; m=0; $R^7$=—C(O)—NHCH$_2$C(O)-(1-Piperidinyl);
Formula II: $R^0$=ethyl; $R^5$=—OH; m=0; $R^7$=—C(O)—NHCH$_2$C(O)-(1-Pyrrolidinyl);
Formula II: $R^0$=ethyl; $R^5$=—OH; m=0; $R^7$=—C(O)—NHCH$_2$C(O)—CH$_2$CH(OCH$_2$CH$_3$)$_2$;
Formula II: $R^0$=ethyl; $R^5$=—OH; m=0; $R^7$=—C(O)—NHCH$_2$C(O)—CH$_2$CHO;
Formula II: $R^0$=ethyl; $R^5$=—OH; m=0; $R^7$=—CO$_2$—CH$_2$CH$_3$;
Formula II: $R^0$=ethyl; $R^5$=—OH; m=0; $R^7$=—CO$_2$—CH$_2$CH(CH$_3$)$_2$;
Formula II: $R^0$=ethyl; $R^5$=—OH; m=0; $R^7$=—CO$_2$—CH$_2$-(Phenyl);
Formula II: $R^0$=ethyl; $R^5$=—OH; m=0; $R^7$=—CO$_2$—CH$_2$CH$_2$CH$_3$;
Formula II: $R^0$=ethyl; $R^5$=—OH; m=0; $R^7$=—CO$_2$-(CH$_2$)$_3$CH$_3$;
Formula II: $R^0$=ethyl; $R^5$=—OH; m=0; $R^7$=—C(O)—CO$_2$CH$_3$;
Formula II: $R^0$=ethyl; $R^5$=—OH; m=0; $R^7$=—C(O)-(2-Acetoxyphenyl);
Formula II: $R^0$=ethyl; $R^5$=—OH; m=0; $R^7$=—C(O)-(3-Pyridyl);
Formula II: $R^0$=ethyl; $R^5$=—OH; m=0; $R^7$=—C(O)-(4-Pyridyl);
Formula II: $R^0$=ethyl; $R^5$=—OH; m=0; $R^7$=—C(O)—CH$_2$NH—C(O)CH$_3$;
Formula II: $R^0$=ethyl; $R^5$=—OH; m=0; $R^7$=—C(O)-(CH$_2$)$_2$NH—C(O)CH$_3$;
Formula II: $R^0$=ethyl; $R^5$=—OH; m=0; $R^7$=(D or L) —C(O)—CH(CH$_3$)NH—C(O)CH$_3$;
Formula II: $R^0$=ethyl; $R^5$=—OH; m=0; $R^7$=—C(O)-(2-Acetamidophenyl);
Formula II: $R^0$=ethyl; $R^5$=—OH; m=0; $R^7$=—C(O)-(2-Cyanophenyl);
Formula II: $R^0$=ethyl; $R^5$=—OH; m=0; $R^7$=—C(O)-(2-Pyridyl);
Formula II: $R^0$=ethyl; $R^5$=—OH; m=0; $R^7$=—C(O)—CH$_2$—NH—C(O)—NH$_2$;
Formula II: $R^0$=ethyl; $R^5$=—OH; m=0; $R^7$=(L)—C(O)—CH(CH(OH)—CH$_3$)—NH—C(O)CH$_3$;
Formula II: $R^0$=ethyl; $R^5$=—OH; m=0; $R^7$=(L)—C(O)—CH(OH)—CH$_3$;
Formula II: $R^0$=ethyl; $R^5$=—OH; m=0; $R^7$=(D)—C(O)—CH(OH)—CH$_3$;
Formula II: $R^0$=ethyl; $R^5$=—OH; m=0; $R^7$=(D)—C(O)—CH$_2$(OH);
Formula II: $R^0$=ethyl; $R^5$=—OH; m=1; $R^7$=—CH$_3$;
Formula II: $R^0$=ethyl; $R^5$=—OH; m=1; $R^7$=—CH$_3$;
Formula II: $R^0$=ethyl; $R^5$=—OH; m=2; $R^7$=—CH$_3$;
Formula II: $R^0$=ethyl; $R^5$=—OH; m=0; $R^7$=—CH$_2$SCH$_3$;
Formula II: $R^0$=ethyl; $R^5$=—OH; m=0; $R^7$=—CH$_2$OCH$_3$; and
Formula II: $R^0$=ethyl; $R^5$=—OH; m=1; $R^7$=-Phenyl.

Preferred compounds are Selected from the group consisting of:

Formula II: $R^0$=ethyl; $R^5$=—OH; m=0; $R^7$=—CH$_2$—CH$_2$—CO$_2$-Phenyl;
Formula II: $R^0$=ethyl; $R^5$=—OH; m=0; $R^7$=—CH$_2$—CH$_2$—CO$_2$CH$_2$CH$_3$;
Formula II: $R^0$=ethyl; $R^5$=—OH; m=0; $R^7$=—CH$_2$—CH$_2$—CO$_2$CH$_2$CH$_2$OCH$_3$;
Formula II: $R^0$=ethyl; $R^5$=—OH; m=0; $R^7$=—CH$_2$—CH$_2$—CO$_2$CH$_2$CF$_3$;
Formula II: $R^0$=ethyl; $R^5$=—OH; m=0; $R^7$=—CH$_2$—CH$_2$—CO$_2$CH$_2$CH$_2$OH;
Formula II: $R^0$=ethyl; $R^5$=—OH; m=0; $R^7$=—CH$_2$—CH$_2$—CO$_2$ tert-Butyl;
Formula II: $R^0$=ethyl; $R^5$=—OH; m=0; $R^7$=—CH$_2$—CH$_2$—CO$_2$CH$_2$CH$_2$N(CH$_3$)$_2$;
Formula II: $R^0$=ethyl; $R^5$=—OH; m=0; $R^7$=—CH$_2$—CH$_2$—CO$_2$H;
Formula II: $R^0$=ethyl; $R^5$=—OH; m=0; $R^7$=—CH$_2$—CH$_2$—CONH$_2$;
Formula II: $R^0$=ethyl; $R^5$=—OH; m=0; $R^7$=—CH$_2$—CH$_2$—CO-(4-morpholinyl);
Formula II: $R^0$=ethyl; $R^5$=—OH; m=0; $R^7$=—CH$_2$—CH$_2$—CONHOH;
Formula II: $R^0$=ethyl; $R^5$=—OH; m=0; $R^7$=—CH$_2$—CH$_2$—CON(CH$_3$)OH;
Formula II: $R^0$=ethyl; $R^5$=—OH; m=0; $R^7$=—CH$_2$—CO$_2$—CH$_3$;
Formula II: $R^0$=ethyl; $R^5$=—OH; m=0; $R^7$=—CH$_2$—CO$_2$—C(CH$_3$)$_3$;
Formula II: $R^0$=ethyl; $R^5$=—OH; m=1; $R^7$=-(4-Hydroxyphenyl);
Formula II: $R^0$=ethyl; $R^5$=—OH; m=2; $R^7$=-(4-Hydroxyphenyl);
Formula II: $R^0$=ethyl; $R^5$=—OH; m=1; $R^7$=—CH$_2$CH$_2$OH;
Formula II: $R^0$=ethyl; $R^5$=—OH; m=2; $R^7$=—CH$_2$CH$_2$OH;
Formula II: $R^0$=ethyl; $R^5$=—OH; m=1; $R^7$=—CH$_2$CH$_2$CH$_2$OH;
Formula II: $R^0$=ethyl; $R^5$=—OH; m=2; $R^7$=—CH$_2$CH$_2$CH$_2$OH;
Formula II: $R^0$=ethyl; $R^5$=—OH; m=2; $R^7$=—CH$_2$CO$_2$CH$_3$;
Formula II: $R^0$=ethyl; $R^5$=—OH; m=2; $R^7$=—CH$_2$CO$_2$C(CH$_3$)$_3$;
Formula II: $R^0$=ethyl; $R^5$=—OH; m=2; $R^7$=—CH$_2$CO$_2$CH$_2$CH$_3$;
Formula II: $R^0$=ethyl; $R^5$=—OH; m=0; $R^7$=—CH$_2$—(CH$_3$)C=N—NH—C(O)—NH$_2$;
Formula II: $R^0$=ethyl; $R^5$=—OH; m=0; $R^7$=—C(O)—NH—CH$_2$CH$_3$;
Formula II: $R^0$=ethyl; $R^5$=—OH; m=0; $R^7$=—C(O)—NH—CH$_2$CH$_2$CH$_3$;
Formula II: $R^0$=ethyl; $R^5$=—OH; m=0; $R^7$=—C(O)—NH—CH(CH$_3$)$_2$;
Formula II: $R^0$=ethyl; $R^5$=—OH; m=0; $R^7$=—C(O)—NH-Phenyl;
Formula II: $R^0$=ethyl; $R^5$=—OH; m=0; $R^7$=—C(O)—N(CH$_3$)$_2$;
Formula II: $R^0$=ethyl; $R^5$=—OH; m=0; $R^7$=—C(O)—N(CH$_2$CH$_3$)$_2$;
Formula II: $R^0$=ethyl; $R^5$=—OH; m=0; $R^7$=—C(O)-(4-Morpholinyl);
Formula II: $R^0$=ethyl; $R^5$=—OH; m=0; $R^7$=—C(O)—NHCH$_2$C(O)-(4-Morpholinyl);

Formula II: $R^0$=ethyl; $R^5$=—OH; m=0; $R^7$=—C(O)—NH CH$_2$C(O)-(1-Piperidinyl);

Formula II: $R^0$=ethyl; $R^5$=—OH; m=0; $R^7$=—C(O)—NHCH$_2$C(O)—CH$_2$CH(OCH$_2$CH$_3$)$_2$;

Formula II: $R^0$=ethyl; $R^5$=—OH; m=0;$R^7$=—C(O)-(2-Acetoxyphenyl);

Formula II: $R^0$=ethyl; $R^5$=—OH; m=0;$R^7$=—C(O)-(3-Pyridyl);

Formula II: $R^0$=ethyl; $R^5$=—OH; m=0;$R^7$=—C(O)-(4-Pyridyl);

Formula II: $R^0$=ethyl; $R^5$=—OH; m=0;$R^7$=—C(O)—CH$_2$NH—C(O)CH$_3$;

Formula II: $R^0$=ethyl; $R^5$=—OH; m=0;$R^7$=—C(O)-(CH$_2$)$_2$NH—C(O)CH$_3$;

Formula II: $R^0$=ethyl; $R^5$=—OH; m=0; $R^7$=(D or L)—C(O)—CH(CH$_3$)NH—C(O)CH$_3$;

Formula II: $R^0$=ethyl; $R^5$=—OH; m=0;$R^7$=—C(O)-(2-Acetamidophenyl);

Formula II: $R^0$=ethyl; $R^5$=—OH; m=0;$R^7$=—C(O)-(2-Cyanophenyl);

Formula II: $R^0$=ethyl; $R^5$=—OH; m=0;$R^7$=—C(O)-(2-Pyridyl);

Formula II: $R^0$=ethyl; $R^5$=—OH; m=0;$R^7$=—C(O)—CH$_2$—NH—C(O)—NH$_2$;

Formula II: $R^0$=ethyl; $R^5$=—OH; m=0; $R^7$=(L)—C(O)—CH(CH(OH)—CH$_3$)—NH—C(O)CH$_3$;

Formula II: $R^0$=ethyl; $R^5$=—OH; m=0;$R^7$=(L)—C(O)—CH(OH)—CH$_3$;

Formula II: $R^0$=ethyl; $R^5$=—OH; m=0;$R^7$=(D)—C(O)—CH(OH)—CH$_3$;

Formula II: $R^0$=ethyl; $R^5$=—OH; m=2;$R^7$=—CH$_3$; and

Formula II: $R^0$=ethyl; $R^5$=—OH; m=0;$R^7$=—CH$_2$SCH$_3$.

Particularly preferred compounds are selected from the group consisting of:

Formula II: $R^0$=ethyl; $R^5$=—OH; m=0;$R^7$=—CH$_2$—CH$_2$—CO$_2$-Phenyl;

Formula II: $R^0$=ethyl; $R^5$=—OH; m=0;$R^7$=—CH$_2$—CH$_2$CO$_2$CH$_2$CF$_3$;

Formula II: $R^0$=ethyl; $R^5$=—OH; m=0;$R^7$=—CH$_2$—CH$_2$—CO$_2$ tert-Butyl;

Formula II: $R^0$=ethyl; $R^5$=—OH; m=0;$R^7$=—CH$_2$—CH$_2$—CONH$_2$;

Formula II: $R^0$=ethyl; $R^5$=—OH; m=0;$R^7$=—CH$_2$—CH$_2$—CO-(4-Morpholinyl);

Formula II: $R^0$=ethyl; $R^5$=—OH; m=0;$R^7$=—CH$_2$—CH$_2$—CONHOH;

Formula II: $R^0$=ethyl; $R^5$=—OH; m=0;$R^7$=—CH$_2$—CH$_2$—CON(CH$_3$)OH;

Formula II: $R^0$=ethyl; $R^5$=—OH; m=0;$R^7$=—CH$_2$—CO$_2$—CH$_3$;

Formula II: $R^0$=ethyl; $R^5$=—OH; m=0;$R^7$=—CH$_2$—CO$_2$—C(CH$_3$)$_3$;

Formula II: $R^0$=ethyl; $R^5$=—OH; m=1;$R^7$=-(4-Hydroxyphenyl);

Formula II: $R^0$=ethyl; $R^5$=—OH; m=2;$R^7$=-(4-Hydroxyphenyl);

Formula II: $R^0$=ethyl; $R^5$=—OH; m=1;$R^7$=—CH$_2$CH$_2$OH;

Formula II: $R^0$=ethyl; $R^5$=—OH; m=2;$R^7$=—CH$_2$CH$_2$OH;

Formula II: $R^0$=ethyl; $R^5$=—OH; m=1;$R^7$=—CH$_2$CH$_2$CH$_2$OH;

Formula II: $R^0$=ethyl; $R^5$=—OH; m=2;$R^7$=—CH$_2$CH$_2$CH$_2$OH;

Formula II: $R^0$=ethyl; $R^5$=—OH; m=2;$R^7$=—CH$_2$CO$_2$CH$_3$;

Formula II: $R^0$=ethyl; $R^5$=—OH; m=0; $R^7$=—CH$_2$-(CH$_3$)C=N—NH—C(O)—NH$_2$;

Formula II: $R^0$=ethyl; $R^5$=—OH; m=0;$R^7$=—C(O)—NH—CH$_2$CH$_3$;

Formula II: $R^0$=ethyl; $R^5$=—OH; m=0;$R^7$=—C(O)—NH—CH$_2$CH$_2$CH$_3$;

Formula II: $R^0$=ethyl; $R^5$=—OH; m=0;$R^7$=—C(O)—NH—CH(CH$_3$)$_2$;

Formula II: $R^0$=ethyl; $R^5$=—OH; m=0;$R^7$=—C(O)—NH-Phenyl;

Formula II: $R^0$=ethyl; $R^5$=—OH; m=0;$R^7$=—C(O)—N(CH$_3$)$_2$;

Formula II: $R^0$=ethyl; $R^5$=—OH; m=0;$R^7$=—C(O)—N(CH$_2$CH$_3$)$_2$;

Formula II: $R^0$=ethyl; $R^5$=—OH; m=0;$R^7$=—C(O)-(4-Morpholinyl);

Formula II: $R^0$=ethyl; $R^5$=—OH; m=0; $R^7$=—C(O)—NHCH$_2$C(O)-(4-Morpholinyl);

Formula II: $R^0$=ethyl; $R^5$=—OH; m=0; $R^7$=—C(O)—NHCH$_2$C(O)-(1-Piperidinyl);

Formula II: $R^0$=ethyl; $R^5$=—OH; m=0;$R^7$=—C(O)-(2-Acetoxyphenyl);

Formula II: $R^0$=ethyl; $R^5$=—OH; m=0;$R^7$=—C(O)-(3-Pyridyl);

Formula II: $R^0$=ethyl; $R^5$=—OH; m=0;$R^7$=—C(O)-(4-Pyridyl);

Formula II: $R^0$=ethyl; $R^5$=—OH; m=0;$R^7$=—C(O)—CH$_2$NH—C(O)CH$_3$;

Formula II: $R^0$=ethyl; $R^5$=—OH; m=0;$R^7$=—C(O)-(CH$_2$)$_2$NH—C(O)CH$_3$;

Formula II: $R^0$=ethyl; $R^5$=—OH; m=0;$R^7$=—C(O)-(2-Pyridyl);

Formula II: $R^0$=ethyl; $R^5$=—OH; m=0; $R^7$=(L)—C(O)—CH(CH(OH)—CH$_3$)—NH—C(O)CH$_3$;

Formula II: $R^0$=ethyl; $R^5$=—OH; m=0;$R^7$=(D)—C(O)—CH(OH)—CH$_3$;

Formula II: $R^0$=ethyl; $R^5$=—OH; m=2;$R^7$=—CH$_3$; and

Formula II: $R^0$=ethyl; $R^5$=—OH; m=0;$R^7$=—CH$_2$SCH$_3$.

Especially preferred compounds are selected from the group consisting of:

Formula II: $R^0$=ethyl; $R^5$=—OH; m=0;$R^7$=—CH$_2$—CH$_2$—CONH$_2$;

Formula II: $R^0$=ethyl; $R^5$=—OH; m=0;$R^7$=—CH$_2$—CH$_2$—CO-(4-Morpholinyl);

Formula II: $R^0$=ethyl; $R^5$=—OH; m=0;$R^7$=—CH$_2$—CH$_2$—CONHOH;

Formula II: $R^0$=ethyl; $R^5$=—OH; m=0;$R^7$=—CH$_2$—CH$_2$—CON(CH$_3$)OH;

Formula II: $R^0$=ethyl; $R^5$=—OH; m=1;$R^7$=-(4-Hydroxyphenyl);

Formula II: $R^0$=ethyl; $R^5$=—OH; m=2;$R^7$=-(4-Hydroxyphenyl);

Formula II: $R^0$=ethyl; $R^5$=—OH; m=1;$R^7$=—CH$_2$CH$_2$OH;

Formula II: $R^0$=ethyl; $R^5$=—OH; m=2;$R^7$=—CH$_2$CH$_2$OH;

Formula II: $R^0$=ethyl; $R^5$=—OH; m=0;$R^7$=—C(O)—NH—CH$_2$CH$_3$;

Formula II: $R^0$=ethyl; $R^5$=—OH; m=0;$R^7$=—C(O)—NH—CH$_2$CH$_2$CH$_3$;

Formula II: $R^0$=ethyl; $R^5$=—OH; m=0;$R^7$=—C(O)—NH—CH(CH$_3$)$_2$;

Formula II: $R^0$=ethyl; $R^5$=—OH; m=0;$R^7$=—C(O)—N(CH$_3$)$_2$;

Formula II: $R^0$=ethyl; $R^5$=—OH; m=0;$R^7$=—C(O)—N(CH$_2$CH$_3$)$_2$;

Formula II: $R^0$=ethyl; $R^5$=—OH; m=0;$R^7$=—C(O)-(4-Morpholinyl);

Formula II: $R^0$=ethyl; $R^5$=—OH; m=0;$R^7$=—C(O)-(2-Acetoxyphenyl);

Formula II: $R^0$=ethyl; $R^5$=—OH; m=0;$R^7$=—C(O)-(3-Pyridyl);

Formula II: $R^0$=ethyl; $R^5$=—OH; m=0;$R^7$=—C(O)-(4-Pyridyl);

Formula II: $R^0$=ethyl; $R^5$=—OH; m=0;$R^7$=—C(O)—CH$_2$NH—C(O)CH$_3$;

Formula II: $R^0$=ethyl; $R^5$=—OH; m=0;$R^7$=—C(O)-(CH$_2$)$_2$NH—C(O)CH$_3$;

Formula II: $R^0$=ethyl; $R^5$=—OH; m=0;$R^7$=(D)—C(O)—CH(OH)—CH$_3$) and

Formula II: $R^0$=ethyl; $R^5$=—OH; m=0;$R^7$=—CH$_2$SCH$_3$.

Most preferred compounds are selected from the group consisting of:

Formula II: $R^0$=ethyl; $R^5$=—OH; m=0;$R^7$=—CH$_2$—CH$_2$—CO-(4-Morpholinyl);

Formula II: $R^0$=ethyl; $R^5$=—OH; m=1;$R^7$=-(4-Hydroxyphenyl);

Formula II: $R^0$=ethyl; $R^5$=—OH; m=2;$R^7$=-(4-Hydroxyphenyl);

Formula II: $R^0$=ethyl; $R^5$=—OH; m=0;$R^7$=—C(O)—CH$_2$NH—C(O)CH$_3$;

Formula II: $R^0$=ethyl; $R^5$=—OH; m=0;$R^7$=—C(O)-(CH$_2$)$_2$NH—C(O)CH$_3$; and Formula II: $R^0$=ethyl; $R^5$=—OH; m=0;$R^7$=(D)—C(O)—CH(OH)—CH$_3$.

Intermediates useful in the preparation of the compounds of the invention include the following:

(III)

wherein n is zero or one, $R^0$ is hydrogen, methyl, ethyl, allyl; propyl, 2-hydroxyethyl, cyclopropylmethyl, 2-oxopropyl or 2-ethanal, $R^1$ and $R^2$ are independently hydrogen or hydroxy, subject to the proviso that when one of $R^1$ or $R^2$ is hydroxy, the other of $R^1$ and $R^2$ is hydrogen; or, alternatively, $R^1$ and $R^2$ taken together are oxo, $R^3$ and $R^4$ are independently hydrogen, halogen, or hydroxy, subject to the proviso that when one of $R^3$ or $R^4$ is halogen or hydroxy, the other of $R^3$ and $R^4$ is hydrogen; or, alternatively, $R^3$ and $R^4$ taken together are oxo, $R^5$ is hydrogen, hydroxy, or protected hydroxy, and $R^6$ is hydrogen; or alternatively, $R^5$ and $R^6$ taken together form a C-23/C-24 bond; and one of $R^{25}$ and $R^{26}$ is —OH or a leaving group such as —O—S(O)$_2$F or —O—S(O)$_2$CF$_3$ and the other is hydrogen, and (IV)

wherein $R^0$ is hydrogen, methyl, ethyl, allyl, propyl, 2-hydroxyethyl, cyclopropylmethyl, 2-oxopropyl or 2-ethanal, $R^5$ is hydrogen, hydroxy, or protected hydroxy, and one of $R^{25}$ and $R^{26}$ is —OH or a leaving group such as —O—S(O)$_2$F or —O—S(O)$_2$CF$_3$ and the other is hydrogen.

The compounds of the invention may be prepared using one or more processes. The starting materials for use in these processes are preferably one of the macrolides isolated from culture media obtained in accordance with known methods by fermentation of microorganisms of the genus Streptomyces, which are disclosed in European Patent Application No. 0184162. Samples are available from the Fermentation Research Institute, Tsukuba, Ibaraki 305, Japan under the provisions of the Budapest Treaty, under deposit No. FERM BP-927. This strain has been redeposited on Apr. 27, 1989 with the Agricultural Research Culture Collection International Depository, Peoria, Ill. 61604, USA under the provisions of the Budapest Treaty, under deposit No. NRRL 18488. The macrolide FR-900520 (European Patent Application 0184162), also known as ascomycin, may be prepared in accordance to the published methods of (i) H. Hatanaka, M. Iwami, T. Kino, T. Goto and M. Okuhara, FR-900520 and FR-900523, *Novel immunosuppressants isolated from A streptomyces. I. Taxonomy of the producing strain. J. Antibiot.*, 1988. XLI(11), 1586–1591;(ii) H. Hatanaka, T. Kino, S. Miyata, N. Inamura, A. Kuroda, T. Goto, H. Tanaka and M. Okuhara, FR-900520 and FR-900523,*Novel immunosuppressants isolated from A streptomyces. II. Fermentation, isolation and physico-chemical and biological characteristics. J. Antibiot.*, 1988. XLI(11), 1592–1601; (iii) T. Arai, Y. Koyama, T. Suenaga and H. Honda, *Ascomycin, An Antifungal Antibiotic. J. Antibiot.*, 1962. 15(231–2); and (iv) T. Arai in U.S. Pat. No. 3,244,592. One or more of the processes discussed below may then be employed to produce the desired compounds of the invention.

Methods for preparing the compounds of the invention are shown in Scheme I-VI.

Scheme I illustrates a general procedure for preparing the compounds of the invention. Compound 1, where M is the macrolide shown, is activated by treatment with sulfonyl chloride, fluorosulfonyl anhydride (prepared according to the procedure described by S. Kongpricha, W. G. Preusse and R. Schwarer, in Inorganic Synthesis, 1968, 11, p151–155) or trifluoromethanesulfonyl anhydride (Aldrich) in a solvent which does not adversely affect the reaction (e.g. diethyl ether, dichloromethane, tetrahydrofuran, chloroform or N-methylpyrrolidone or a mixture thereof. The reaction may require cooling or heating, depending on the method used. Further, the reaction is preferably conducted in the presence of an organic or inorganic base such as cesium bicarbonate, pyridine, lutidine, picoline, quinoline, diisopropylethylamine and the like. The reaction temperature is preferably from −100° C. to 30° C., and more preferably from −78° C. to 0° C. The reaction may require 20 minutes to 24 hours to complete, depending on the reagent chosen to give compound 2 where R* is a —S(O)$_2$Cl, —S(O)$_2$F or —S(O)$_2$CF$_3$ group. Treatment of 2 with thiourea or thioacetamide or thioacetate followed by morpholine or pyrrolidine or diethylamine affords the 32-epi-thiol compound 3;this reaction epimerizes the C32 center to afford the epi-isomer. This compound can then be functionalized with the various R$^7$ groups defined above to give the desired compounds 4. Typically the coupling reactions are run in an inert solvent such as methylene chloride or acetonitrile or DMF in the presence of diisopropylethylamine or tetrabutylammonium fluoride or triethylamine with or without a catalytic amount of 4-dimethylaminopyridine.

Scheme II illustrates some methods for derivatizing the C32 thiol functionality. Compounds where R$^7$ is —CH$_2$CH$_2$—CO$_2$R$^9$ can be prepared by the Michael reaction. The R$^7$ precursor (CH$_2$=CH—CO$_2$R$^9$ or alternatively CH$_2$=C(alkyl)—CO$_2$R$^9$) is reacted with thiol compound 3 in an inert solvent such as acetonitrile or methylene chloride in the presence of diisopropylethylamine to give product 5. Alternatively, one can use an intial Michael acceptor (CH$_2$=CH—CO$_2$$^{R9*}$ or alternatively CH$_2$=C(alkyl)—CO$_2$R$^{9*}$) where R$^{9*}$ is tertbutyl or benzyl to give the analogous compound 6. The protecting group is removed (for example, by hydrolysis of a tert-butyl ester or catalytic hydrogenation of a benzyl ester) and then the free carboxylic acid 7 is esterified using R$^9$OH (for example, using standard peptide coupling conditions of EDCI, N-methylmorpholine and dimethylaminopyridine in methylene chloride, to give the desired product 8.

The corresponding amides where R$^7$ is —CH$_2$CH$_2$—C(O)NR$^{11}$R$^{12}$ can be prepared in an analogous manner Using (CH$_2$=CH—C(O)NR$^{11}$R$^{12}$ or alternatively CH$_2$=C(alkyl)—C(O)NR$^{11}$R$^{12}$) as the Michael acceptor and reacting with compound 3 to give compound 9 using the Michael reaction conditions described above. The corresponding hydroxamic acids where R$^7$ is —CH$_2$CH$_2$—C(O)N(OH)R$^{10}$ can be prepared in an analogous manner using (CH$_2$=CH—C(O)N(O—P)R$^{10}$ or alternatively CH$_2$=C(alkyl)—C(O)N(OP)R$^{10}$ where P is an hydroxy protecting group) as the Michael acceptor and reacting with compound 3 to give compound 10 using the Michael reaction conditions described above. The hydroxy protecting group is removed (for example, using HF in acetonitrile for a t-butyloxycarbonyl (Boc) or t-butyldiphenylsilyl (TBDPS) protecting group) to give the hydroxamic acid 11.

Scheme III illustrates other methods for derivatizing the C32 thiol functionality. The 35-epi-thiol compound 3 is reacted with R$^8$—C(O)—L$_3$—V where L$_3$ is alkylene, V is a leaving group (for example a halide such as Cl, Br or I or a sulfonate such as mesylate, tosylate, or triflate and the like) and R$^8$ is —O—R$^9$, —N(OH)R$^{10}$ or —NR$^{11}$R$^{12}$ under conditions described above for the Michael reaction to give adduct 12. The reactions described in Scheme II can also be applied to these thiol adducts. Hydroxy alkyl compounds 13 may be prepared in like manner from compound 3 and HO—L$_1$—V where L$_1$ is alkylene and V is a leaving group in for example, acetonitrile with diisopropylamine or in isopropanol with cesium carbonate. Treatment of compound 3 with R$^7$—V where V is a leaving group affords other derivatized thiol compounds 14.

Other methods for functionalizing the C32 thiol group are shown in Scheme IV. Thiol compound 3 can be reacted with an isocyanate (R$^{12}$—N=C=O) under the standard reactions conditions described above (for example, diisopropylethylamine in methylene chloride) to give compound 15. Alternatively, treatment of compound 3 with R$^{13}$—C(0)—W where W is a leaving group such as halide or 4-nitrophenoxy (for example, in THF or methylene chloride with diisopropylethylamine and 4-dimethylaminopyridine) affords thioesters 16. Compound 16 may also be obtained by treatment of compound 3 with R$^{13}$—CO$_2$H under standard peptide coupling conditions (diisopropylcarbodiimide, diisopropylethylamine, 1-hyroxybenzotriazole and 4-dimethylaminopyridine in methylene chloride or dimethylaminopropyl ethylcarbodiimide, 1-hydroxybenzotriazole and N-methylmorpholine in DMF).

Scheme V illustrates another approach to preparing the compounds of the invention. Hydroxy compound 17, a compound of formula III where R$^{25}$ is hydrogen and R$^{26}$ is hydroxy, is activated by reaction with sulfonyl chloride, fluorosulfonyl anhydride or trifluoromethanesulfonyl anhydride to give compound 18 wherein X is an activating group (for example, fluorosulfonyl or trifluoromethanesulfonyl). (In a preferred embodiment compound 17 is ascomycin, a compound of formula IV where R$^0$ is ethyl, R$^5$ is hydroxy, R$^{25}$ is hydrogen and R$^{26}$ is hydroxy.) Treatment of compound 18 with the appropriate thiol R$^7$—SH (for example, in acetonitrile with diisopropylethylamine) affords the desired sulfides 19.

Scheme VI illustrates the preparation of a compound of formula III, wherein R$^{25}$ is —S(O)$_m$R$^7$ where m is 1 or 2 and R$^{26}$ is hydrogen, by oxidation of compound 19 containing an —S—R$^7$ group. Suitable oxidizing reagents are organic or inorganic peracids, peroxides, ruthenium tetraoxide, chromates, permanganates or periodates. The oxidation may be carried out in a solvent which does not adversely affect the reaction (e.g. diethyl ether, dichloromethane, tetrahydrofuran, chloroform or a mixture thereof). The reaction may require cooling or heating, depending on the method used. Further, the reaction is preferably conducted in the presence of an inorganic base such as cesium bicarbonate, cesium carbonate, potassium carbonate and the like. The reaction temperature is preferably from −100° C. to 30° C., and more preferably from −78° C. to 0° C. The reaction may require 20 minutes to 24 hours to complete, depending on the reagent chosen. The reaction affords a mixture of isomeric sulfoxides (20 and 21) plus the sulfonyl compound 22.

Scheme I
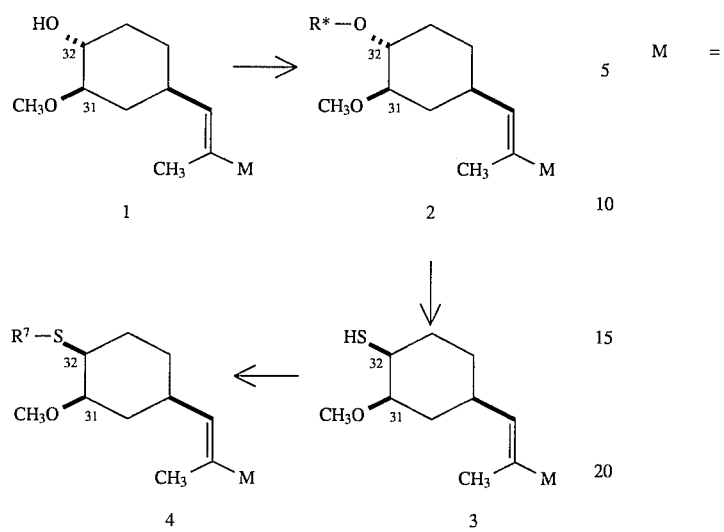
M =
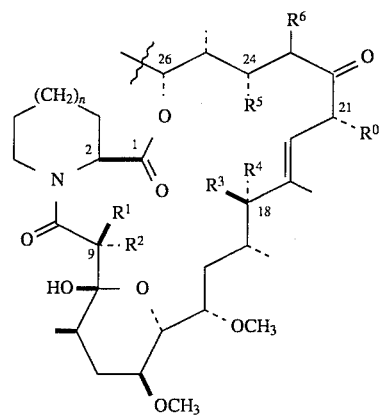
Scheme II
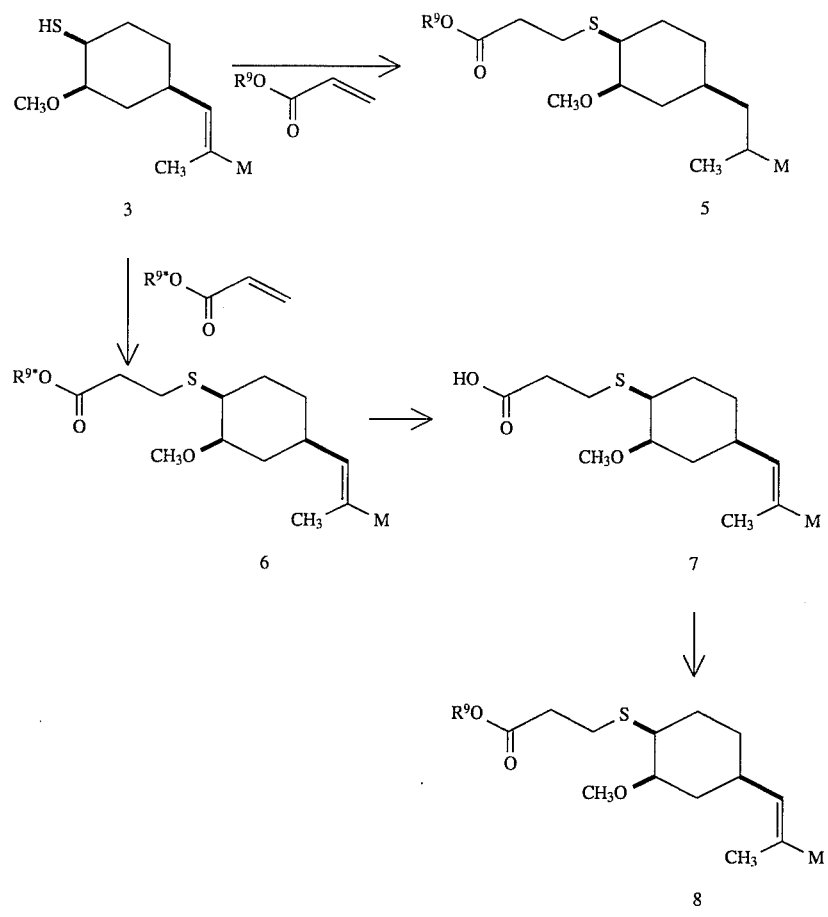

Scheme II
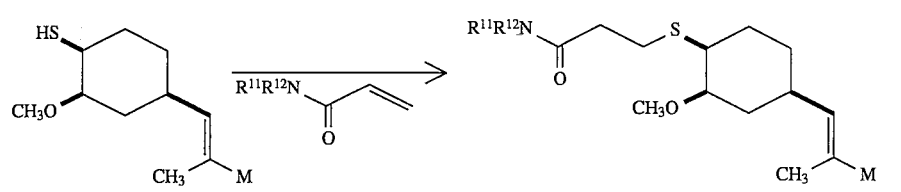
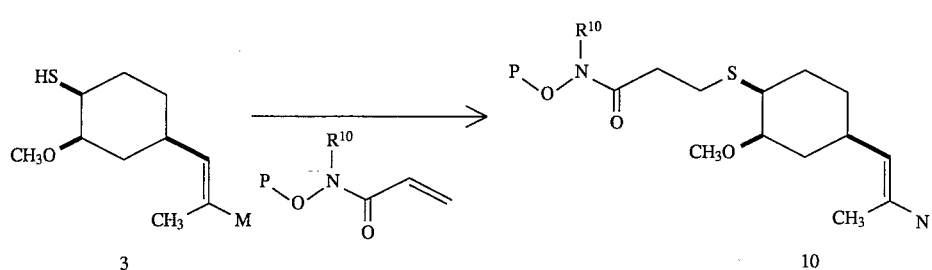
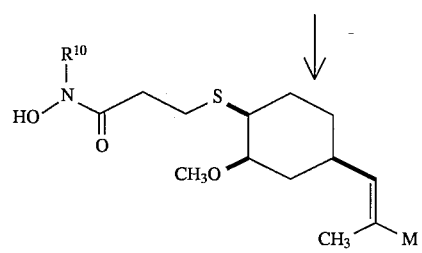
Scheme III
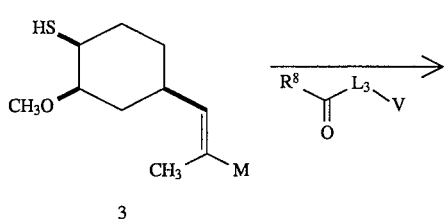
-continued
Scheme III
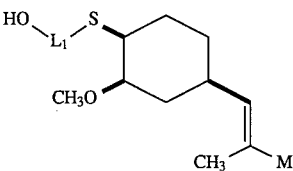
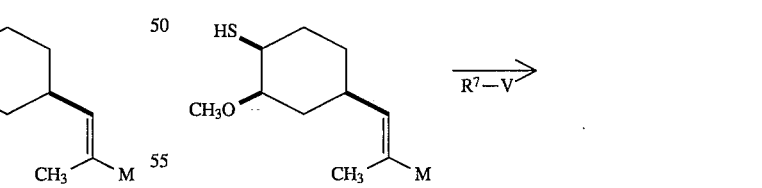
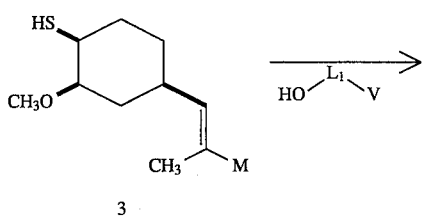
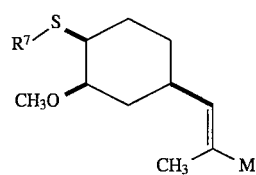

5,604,234
27                                                                              28
Scheme IV                                                Scheme V
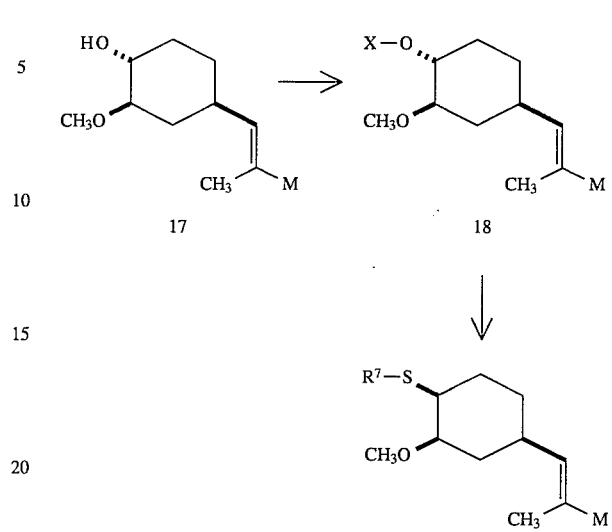
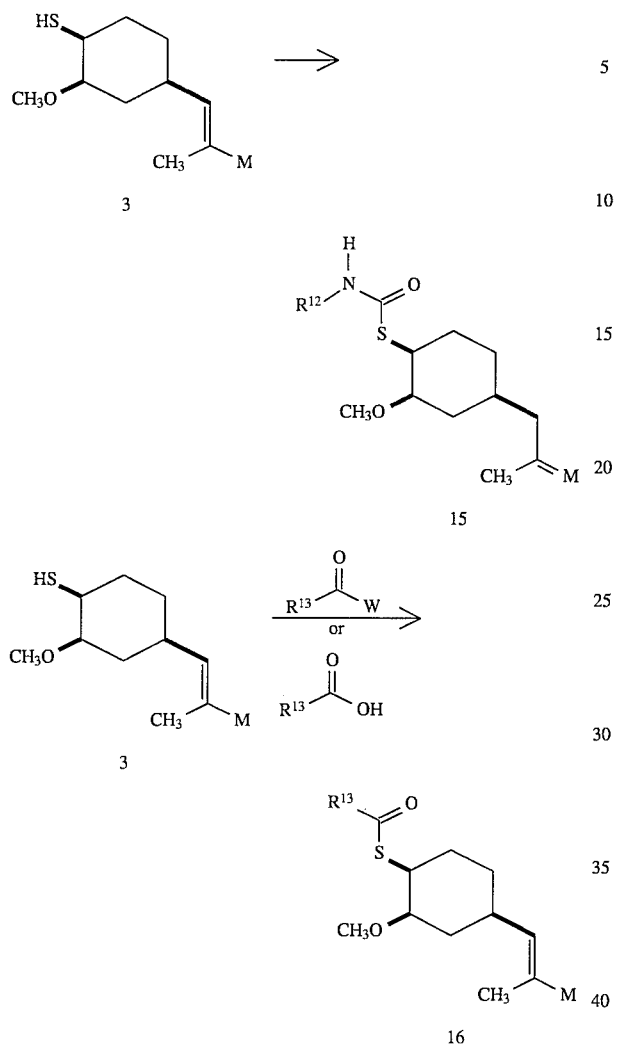
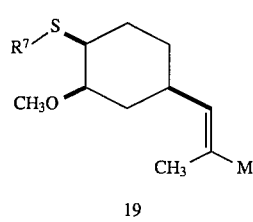

-continued
Scheme VI

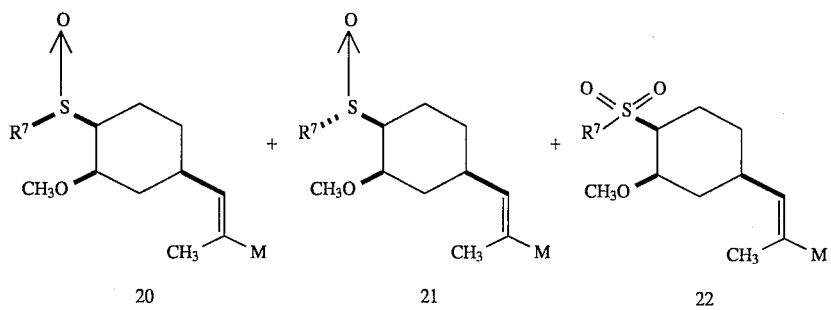

20     21     22

The present invention can be illustrated by the following non-limiting, representative examples. The following abbreviations are used: Boc for tert-butyloxycarbonyl, DMAP for 4-dimethylaminopyridine, DMF for dimethylformamide, EDCI for 1-(3-dimethylaminopropyl)-3-ethylcarbodiimide hydrochloride, $Et_3N$ for triethylamine, EtOAc for ethyl acetate, EtOH for ethanol, HOAc for acetic acid, Hüinig's base for diisopropylethylamine and THF for tetrahydrofuran.

EXAMPLE 1

Formula IV: $R^0$=ethyl, $R^5$—OH; m is 2;$R^{25}$=H; $R^{26}$=—O—S(O)$_2$CF$_3$; (R Configuration for C-32 side chain)

Ascomycin (4.748 g, 6 mmol) was dissolved in 60 mL of methylene chloride at 0° C. Pyridine (4.85 mL, 60 mmol), followed by trifluoromethanesulfonic acid anhydride (1.514 mL, 9 mmol) were carefully added to the reaction mixture. The reaction mixture was stirred at 0° C. for 10 minutes and allowed to warm to room temperature. After stirring for 2 hours, 40 mL of cold aqueous solution of 10% NaHCO$_3$ was carefully added to the cooled reaction mixture, which was then extracted with ethyl acetate (50 mL×3). The combined organic layers were washed with brine, 10% NaHCO$_3$, brine, 10% KHSO$_4$, and brine and dried over anhydrous magnesium sulfate. The solvent was removed in vacuo to afford the C32-triflate in quantitative yield.

EXAMPLE 2

Formula II: $R^0$=ethyl; $R^5$—OH; m is 0;$R^7$CH$_3$C(O)—; (S Configuration for C-32 side chain)

To the compound resulting from Example 1 (923 mg, 1 mmol) dissolved in 3 mL of N,N-dimethylformamide (DMF) was added potassium thioacetate (57 1 mg, 5 mmol). The reaction was stirred at room temperature for 5 hours, and then ethyl acetate (30 mL) was added. The organic layer was washed with brine, 10% NaHCO$_3$, brine, 10% KHSO$_4$ and brine, dried over magnesium sulfate and concentrated in vacuo to give 837 mg of crude product. This material was, purified twice by silica gel column chromatography eluting with 0.5% methanol in chloroform to afford the title compound (165 mg). MS (FAB) m/z: M+K=888. IR(KBr) 3440, 2960, 2930, 2880, 2820, 1740, 1690, 1645, 1455, 1450, 1380,1355,1325,1280,1245,1195,1170,1160,1140,1105, 1035,1020,1010 cm$^{-1}$.

EXAMPLE 3

Formula H: $R^0$=ethyl: $R^5$=—OH; m is 0;$R^7$=C$_6$H$_5$

The title compound is prepared using the method of Guindon, Y., Frenette, R., Fortin, R. and Rokach, J. J. Org. Chem. 48, 1357 (1983). Dried zinc iodide is added to a solution of ascomycin in dry dichloroethane. To the suspension is added thiophenol, and the reaction mixture is stirred for 1 hour. The reaction is quenched with water, the solvent is removed, and the residue is dissolved in ethyl acetate. The ethyl acetate layer is washed with 10% sodium hydrogen carbonate and brine and dried over magnesium sulfate. After the solvent is removed, the crude product is purified on silica gel column chromatography.

EXAMPLE 4

Alternate Preparation of
Formula II: $R^0$=ethyl; $R^5$=—OH; n=0;$R^7$=C$_6$H$_5$

EXAMPLES 4A

Formula III: $R^0$=ethyl; $R^5$=t-butyldimethylsilyloxy; $R^{25}$=t-butyldimethylsilyloxy Ascomycin (15 g) was dissolved in a solution of imidazole (3.75 g) in dry N,N-dimethylformamide (200 mL) and tert-butyldimethylchlorosilane (18.3 g) was added in portions. The reaction mixture was stirred at room temperature for 90 hours, and then the N,N-dimethylformamide and excess tert-butyldimethylchlorosilane were removed by distillation (bath 30° C. at 0.8 torr.). The solid residue was extracted with anhydrous ether (4×50 mL). The combined ether extracts were concentrated in vacuo, and the solid residue was purified by silica gel chromatography eluting with 5% acetone in hexanes to provide the title compound (17 g). MS (FAB) m/z: M+H =1022.

EXAMPLES 4B

Formula III: $R^0$=ethyl; $R^5$=t-butyldimethylsilyloxy; $R^{25}$—OH

A solution of the compound resulting from Example 4A (1.0 g) in acetonitrile (10 mL) was added into a stirred solution of HF (0.1 mL, 40% aqueous) in acetonitrile (10 mL), and the reaction mixture was stirred at room temperature for 10 minutes. Saturated sodium bicarbonate solution (0.5 mL, aqueous) was added and stirring was continued for an additional 20 minutes. The solvent was removed in vacuo. Ether (50 mL) was added to the residue, and the mixture was dried over magnesium sulfate, filtered and concentrated in vacuo. The product was purified by silica gel (20 g) chromatography eluting with 20% (v/v) acetone in hexanes to afford 0.67 g of the title compound. MS (FAB) m/z: M+K=944.

EXAMPLE 4C

Formula II: $R^0$=ethyl; $R^5$=—OH; n=0;$R^7$=C$_6$H$_5$

A solution of the compound resulting from Example 4B in methylene chloride is added to a solution of triflic anhydride in methylene chloride, according to the procedure described in Example 1. To a solution of the obtained product in methylene chloride is added sodium phenylmercaptan in DMF. The reaction mixture is gently warmed until the total disappearance of starting material is observed. The solvent is evaporated, and the crude product is purified by silica gel column chromatography to yield the protected title compound.

To the protected title compound dissolved in acetonitrile is added 48% hydrofluoric acid. The reaction mixture is stirred at room temperature for 4 hours. Ethyl acetate is added to the reaction mixture, and the organic layer is washed with brine, 10% $NaHCO_3$ and brine and then dried over anhydrous magnesium sulfate. Evaporation of the solvent gives crude product which is purified by silica gel (25 g) column chromatography eluting with 1.5% methanol in chloroform.

EXAMPLE 5

Formula II: $R^0$=ethyl; $R^5$=—OH; m=0;$R^7$=benzyl

The title compound is prepared from the compound resulting from Example 4B and sodium benzylmercaptide, according to the procedure described in Example 4C.

EXAMPLE 6

Formula II: $R^0$=ethyl; $R^5$—OH; m=0; $R^7$=—H

The compound resulting from Example 5 is carefully added to anhydrous liquid ammonia. Sodium metal is added until the reaction is complete. The solvent is removed, the residue is dissolved in degassed water, and the crude product is purified by high performance liquid chromatography to yield the title compound.

EXAMPLE 7

Formula II: $R^0$=ethyl; $R^5$=—OH; m=0;$R^7$=—S-Et

The compound resulting from Example 6 is carefully dissolved in degassed water (or a mixed solvent if necessary). Lithium thiocyanate hydrate and zinc chloride (II) are carefully added. After the total disappearance of starting material is observed, ethanethiol is added and the reaction mixture is stirred at room temperature for 5 hours. The solvent is removed, and the crude product is purified by silica gel column chromatography to yield the title compound.

EXAMPLE 8

Formula II: $R^0$=ethyl; $R^5$—OH; m=0;$R^7$=—$CH_2$—$CH_2$—$CO_2$-Phenyl

EXAMPLE 8A

Alternate Preparation of

Formula II: $R^0$=ethyl; $R^5$=—OH; m=0; $R^7$=—H (32-epi-Thiol Ascomycin)

To a stirred solution of ascomycin (30 g, 37.9 mmol) and 2,6lutidine (13.3 mL, 113.8 mmol) in $CH_2Cl_2$ (120 mL) at −70° C. was added slowly trifluoromethanesulfonic acid anhydride (7.66 mL, 45.5 mmol). After stirring at −70° C. for 30 minutes, the reaction mixture was diluted with ether and washed with 10% $KHSO_4$. The organic layer was washed with brine, dried over anhydrous $Na_2SO_4$, filtered through a silica gel plug and concentrated in vacuo to give 34.2 g of 32-trifluoromethanesulfonyl ascomycin in 97% yield.

To 32-trifluoromethanesulfonyl ascomycin in THF (120 mL) was added 2,6-lutidine (6.9 mL, 60.7 mmol) and thiourea (3.38 g, 45.5 mmol) to give a compound of formula II wherein $R^0$ is ethyl, $R^5$ is —OH, m is 0 and $R^7$ is —C(=NH)$NH_{22}$. After the reaction mixture was stirred at room temperature overnight, morpholine (6.5 mL) was added into the reaction, and stirring was continued for 5 hours. The reaction mixture was then partitioned between ethyl acetate and 1N HCl. The organic phase was washed with brine, dried over anhydrous $Na_2SO_4$ and concentrated in vacuo to afford 34.03 g of crude product which was purified on a silica gel plug to give 25.32 g of the tittle compound in 83% yield. m.p. 93°–96° C. MS (FAB) m/e 846 (M+K)$^+$. $^{13}$C NMR (CDCl$_3$) δ213.5, 213.5, 196.2, 192.4, 168.9, 168.6, 165.8, 164.7, 139.6, 138.6, 132.0, 131.5, 129.6, 129.6, 123.2, 122.9, 98.5, 96.9, 79.5, 77.5, 76.8, 76.6, 75.1, 73.6, 73.6, 72.8, 72.1, 70.1, 69.2, 57.4, 56.8, 56.6, 56.2, 56.0, 55.5, 54.9, 54.6, 52.6, 48.5, 48.3, 43.8, 43.2, 42.8, 40.0, 39.4, 39.1, 38.5, 38.5, 35.5, 35.1, 34.5, 33.4, 32.7, 32.7, 32.5, 31.8, 31.7, 30.5, 27.6, 26.3, 26.1, 25.9, 25.9, 25.8, 24.5, 24.5, 24.4, 24.1, 21.0, 20.7, 20.4, 19.4, 16.1, 15.9, 15.8, 15.6, 14.2, 14.0, 11.6, 9.7, 9.3 IR (CHCl$_3$) 3500(br), 2950(s), 2890(sh), 2830(sh), 1745(s), 1700(sh), 1650(s), 1450(s) cm$^{-1}$.

EXAMPLE 8B

Formula II: $R^0$=ethyl; $R^5$=—OH; m=0;$R^7$ =—$CH_2$—$CH_2$—$CO_2$-Phenyl

To the compound resulting from Example 8A (0.3 g, 0.37 mmol) in $CH_3CN$ (3 mL) was added diisopropylethylamine (0.31 mL, 1.78 mmol) followed by phenyl acrylate (0.13 mL, 0.89 mmol). After stirring at room temperature for 1 hour, the solvent was evaporated under reduced pressure, and the residue was partitioned between ethyl acetate and 10% $KHSO_4$. The ethyl acetate layer was washed with brine, dried over sodium sulfate and concentrated in vacuo to afford 310 mg of crude product, which was dissolved in methylene chloride and filtered through a silica gel plug. The partially purified product was eluted with 30:70 acetone-hexane and then further purified by HPLC. on a microsorb column eluting with 20:80 acetone-hexane to give 225 mg (71%) of the title compound. MS (FAB) m/e 994 (M+K)$^+$.

EXAMPLE 9

Formula II: $R^0$=ethyl; $R^5$=—OH; m=0;$R^7$=—$CH_2$—$CH_2$—$CO_2CH_3$

The title compound was prepared in 50% yield by the procedure described in Example 8 substituting methyl acrylate for phenyl acrylate and running the reaction for 48 hours. MS (FAB) m/e 932 (M+K)$^+$.

EXAMPLE 10

Formula II: $R^0$=ethyl; $R^5$=—OH; m=0;$R^7$=—$CH_2$—$CH_2$—$CO_2CH_2CH_3$

The title compound was prepared in 45% yield by the procedure described in Example 8 substituting ethyl acrylate for phenyl acrylate and running the reaction for 48 hours. MS (FAB) m/e 946 (M+K)$^+$.

EXAMPLE 11

Formula II: $R^0$=ethyl; $R^5$ =—OH; m=0;$R^7$=—$CH_2$—$CH_2CO_2CH_2CH_2OCH_3$

The title compound was prepared in 56% yield by the procedure described in Example 8 substituting methoxyethyl acrylate for phenyl acrylate and running the reaction for 48 hours. MS (FAB) m/e 976 (M+K)$^+$.

EXAMPLE 12

Formula II: $R^0$=ethyl; $R^5$=—OH; m=0; $R^7$=—$CH_2$—$CH_2$—$CO_2CH_2CF_3$

The title compound was prepared in 81% yield by the procedure described in Example 8 substituting 2,2,2-trifluoroethyl acrylate for phenyl acrylate and running the reaction for 48 hours. MS (FAB) m/e 1000 (M+K)$^+$.

EXAMPLE 13

Formula II: $R^0$=ethyl; $R^5$=—OH; m=0; $R^7$=—$CH_2$—$CH_2$—$CO_2CH_2CH_2OH$

The title compound was prepared in 76% yield by the procedure described in Example 8 substituting 2-hydroxyethyl acrylate for phenyl acrylate and running the reaction for 48 hours. MS (FAB) m/e 962 (M+K)$^+$.

EXAMPLE 14

Formula II: $R^0$=ethyl; $R^5$=—OH; m=0; $R^7$=—$CH_2$—$CH_2$—$CO_2$Cyclohexyl

The title compound was prepared in 26% yield by the procedure described in Example 8 substituting cyclohexyl acrylate for phenyl acrylate and running the reaction for 48 hours. MS (FAB) m/e 1000 (M+K)$^+$.

EXAMPLE 15

Formula II: $R^0$=ethyl; $R^5$=—OH; m=0; $R^7$=—$CH_2$—$CH_2$—$CO_2$ tert-Butyl

The title compound was prepared in 20 yield by the procedure described in Example 8 substituting tert-butyl acrylate for phenyl acrylate and running the reaction for 48 hours. MS (FAB) m/e 974 (M+K)$^+$.

EXAMPLE 16

Formula II: $R^0$=ethyl; $R^5$=—OH; m=0; $R^7$=—$CH_2$—$CH_2$—$CO_2CH_2CH_2N(CH_3)_2$ The title compound was prepared by the procedure described in Example 8 substituting 2-(N,N-dimethylamino)ethyl acrylate for phenyl acrylate and running the reaction for 48 hours. The pure compound was collected from RP-HPLC in 58% yield. MS (FAB) m/e 989 (M+K)$^+$.

EXAMPLE 17

Formula II: $R^0$=ethyl; $R^5$=—OH; m=0; $R^7$=—$CH_2$—$CH_2$—$CO_2CH_2CH_2CH_2SO_3K$ The title compound was prepared by the procedure described in Example 8 substituting $CH_2$=CH—$CO_2CH_2CH_2CH_2SO_3K$ for phenyl acrylate and running the reaction for 4 days. The pure compound was collected from RP-HPLC in 14% yield. MS (FAB) m/e 1078 (M+K)$^+$. Diagnostic chemical shifts: $^1$H NMR ($C_5D_5N$, 300 MHz) δC31-OMe (3.34), $SCH_2CH_2CH_2SO_3K$ (2.44, 2.68, 4.36).

EXAMPLE 18

Formula II: $R^0$=ethyl; $R^5$=—OH; m=0; $R^7$=—$CH_2$—$CH_2$—$CO_2$Benzyl

The title compound was prepared in 70% yield by the procedure described in Example 8 substituting benzyl acrylate for phenyl acrylate and running the reaction for 24 hours. MS (FAB) m/e 1008 (M+K)$^+$.

EXAMPLE 19

Formula II: $R^0$=ethyl; $R^5$=—OH; m=0; $R^7$=—$CH_2$—$CH_2$—$CO_2H$

The compound resulting from Example 18 and one equivalent of 10% Pd on carbon in EtOH was hydrogenated at room temperature for 3 hours. The catalyst was removed by filtration, the solvent was evaporated, and the resulting crude material was purified by RP—HPLC. to give the title compound in 60% yield. MS (FAB) m/e 918 (M+K)$^+$.

EXAMPLE 20

Formula II: $R^0$=ethyl; $R^5$=—OH; m=0; $R^7$=—$CH2$—$CH_2$—$CO_2CH(CH_3)_2$

To a stirred solution of crude compound resulting from Example 19 (0.3 g, 0.34 mmol) in $CH_2Cl_{12}$ at −10° C. was added isopropanol (0.03 mL, 0.41 mmol), N-methylmorpholine (0.19 mL, 1.7 mmol), EDCI (0.08 g, 0.41 mmol) and DMAP (0.004 g, 0.034 mmol) sequentially. After the reaction was stirred at −10° C. for 1 hour and room temperature for overnight, it was diluted with ethyl acetate and washed with 10% $KHSO_4$, saturated $NaHCO_3$ solution and brine. The organic phase was dried over sodium sulfate and concentrated in vacuo. The crude product was purified by NP-HPLC. on a microsorb column eluting with 20:80 acetone-hexane to afford the title compound (73%). MS (FAB) m/e 960 (M+K)$^+$.

EXAMPLE 21

Formula II: $R^0$=ethyl; $R^5$=—OH; m=0; $R^7$=—$CH_2$—$CH_2$—$CO_2CH(C_2H_5)_2$ The title compound was prepared in 57% yield by the procedure described in Example 20 substituting 3-pentanol for isopropanol. MS (FAB) m/e 988 (M+K)$^+$.

EXAMPLE 22

Formula II: $R^0$=ethyl; $R^5$=—OH; m=0; $R^7$=—$CH_2$—$CH_2$—$CONH_2$

The title compound was prepared in 43% yield by the procedure described in Example 8 substituting acrylamide for phenyl acrylate and reacting for two days at 75° C. MS (FAB) m/e 917 (M+K)$^+$.

EXAMPLE 23

Formula II: $R^0$=ethyl; $R^5$=—OH; m=0; $R^7$=—$CH_2$—$CH_2$—CO-(4-Morpholinyl)

The title compound was prepared in 14% yield by the procedure described in Example 8 substituting N-acryloylmorpholine for phenyl acrylate and reacting for two days at 75° C. MS (FAB) m/e 987 (M+K)$^+$.

EXAMPLE 24

Formula II: $R^0$=ethyl; $R^5$=—OH; m=0; $R^7$=—$CH_2$—$CH_2$—CONHOH

The N-Boc—O—Boc-acrylohydroxamate was prepared by the coupling of protected N-Boc—O—Boc-hydroxylamine and acryloyl chloride in THF in the presence of $Et_3N$ by the procedures described in Tetrahedron Letters, 35, (29) 5157–5160 (1994).

The protected title compound was prepared in 98% crude yield by the procedure described in Example 8 substituting N-Boc—O—Boc-acrylohydroxamate for phenyl acrylate.

The protected compound (0.5 g, 0.5 mmol) was deprotected with 48% aqueous HF (2 mL) in $CH_3CN$ for 3 hours. The tittle compound was collected from RP—HPLC. in 13% yield. MS (FAB) m/e 933 (M+K)+.

EXAMPLE 25

Formula II: $R^0$=ethyl; $R^5$=—OH; m=0;$R^5$=—$CH_2$—$CH_2$—CON($CH_3$)OH

The protect title compound was prepared in 75% crude yield by the procedure described in Example 24 substituting N-methyl—O—t-butyldiphenylsilyl-acrylohydroxamate for N-Boc—O—Boc-acrylohydroxamate.

The protected compound (0.6 g, 0.5 mmol) was deprotected with 48% aqueous HF (2 mL) in $CH_3CN$ for 30 minutes. The tittle compound was collected from RP—HPLC. in 45% yield. MS (FAB) m/e 947 (M+K)$^+$.

EXAMPLE 26

Formula II: $R^0$=ethyl; $R^5$=—OH; m=0;$R^7$=—$CH_2$—$CH_2$—CO—N(OH)CH($CH_3$)$_2$ The protected title compound was prepared in 34% purified yield by the procedure described in Example 24 substituting N-isopropyl—O—t-butyldiphenylsilyl-acrylohydroxamate for N-Boc—O—Boc-acrylohydroxamate.

The protected compound (0.6 g, 0.5 mmol) was deprotected with 48% aqueous HF (2 mL) in $CH_3CN$ for 30 minutes. The tittle compound was collected from RP—HPLC. in 63% yield. MS (FAB) m/e 975 (M+K)$^+$.

EXAMPLE 27

Formula II: $R^0$=ethyl; $R^5$=—OH; m=0;$R^7$=—$CH_2$—$CO_2$-Benzyl

The title compound was prepared in 93% yield by the procedure described in Example 8 substituting benzyl 2-bromoacetate for phenyl acrylate. MS (FAB) m/e 994 (M+K)$^+$.

EXAMPLE 28

Formula II: $R^0$=ethyl; $R^5$=—OH; m=0;$R^7$=—$CH_2$—$CO_2$—$CH_3$

The title compound was prepared in 81% yield by the procedure described in Example 8 substituting me 2-bromoacetate for phenyl acrylate. MS (FAB) m/e 918 (M+K)$^+$.

EXAMPLE 29

Formula II: $R^0$=ethyl; $R^5$=—OH; m=0;$R^7$=—$CH_2CO_2$—C($CH_3$)$_3$

The title compound was prepared in 79% yield by the procedure described in Example 8 substituting t-butyl 2-bromoacetate for phenyl acrylate. MS (FAB) m/e 960 (M+K)$^+$.

EXAMPLE 30

Formula II: $R^0$=ethyl; $R^5$=—OH; m=0;$R^7$=—$CF_2$—$CO_2H$

The title compound was prepared in 60% yield by the procedure described in Example 19 substituting the compound resulting from Example 27 for the compound resulting from Example 18. MS (FAB) m/e 904 (M+K)$^+$.

EXAMPLE 31

Formula II: $R^0$=ethyl: $R^{5=}$—OH; m=0;$R^7$=—$CH_2$—$CH_2$—$CH_2CH_3$

The title compound was prepared in 38% yield by the procedure described in Example 20 using the compound resulting from Example 30 and EtOH. MS (FAB) m/e 932 (M+K)$^+$.

EXAMPLE 32

Formula II: $R^0$=ethyl: $R^5$=—OH; m=0;$R^7$=—$CH_2$—$CO_2CH(CH_{32}$

The title compound was prepared in 21% yield by the procedure described in Example 20 using the compound resulting from Example 30 and isopropanol. MS (FAB) m/e 946 (M+K)$^+$.

EXAMPLE 33

Formula II: $R^0$=ethyl; $R^5$=—OH; m=0;$R^7$=—$CH_2$—$CO_2CH_2CF_3$

The title compound was prepared in 43% yield by the procedure described in Example 20 using the compound resulting from Example 30 and 2,2,2-trifluoroethanol. MS (FAB) m/e 986 (M+K)$^+$.

EXAMPLE 34

Formula II: $R^0$=ethyl; $R^5$=—OH; m=0; $R^7$=—$CH_2$—$CO_2CH_2CH_2OH$

The title compound was prepared in 49% yield by the procedure described in Example 20 using the compound resulting from Example 30 and 1,2-ethanediol. MS (FAB) m/e 948 (M+K)$^+$.

EXAMPLE 35

Formula II: $R^0$=ethyl; $R^5$=—OH; m=0;$R^7$=—$CH_2$—$CO_2CH_2CH_2OCH_3$

The title compound was prepared in 48% yield by the procedure described in Example 20 using the compound resulting from Example 30 and 2-methoxyethanol. MS (FAB) m/e 962 (M+K)$^+$.

EXAMPLE 36

Formula II: $R^0$=ethyl; $R^5$=—OH; m=0; $R^7$=—$CH_2$—$CO_2CH_2CH_2N(CH_3)_2$

The title compound was prepared by the procedure described in Example 20 using the compound resulting from Example 30 and 2(N,N-dimethylamino)ethanol. The pure compound was collected from RP-HPLC in 44 yield. MS (FAB) m/e 975 (M+K)$^+$.

EXAMPLE 37

Formula II: $R^0$=ethyl; $R^5$=—OH; m=0;$R^7$=—$CH_2CO_2CH_2CH_2$OBenzyl

The title compound was prepared in 38% yield by the procedure described in Example 20 using the compound resulting from Example 30 and 2benzyloxyethanol. MS (FAB) m/e 1038 (M+K)$^+$.

EXAMPLE 38

Formula II: $R^0$=ethyl; $R^5$=—OH; m=0;$R^7$=—$CH_2$—CONHOH

The title compound was prepared in 20% yield by the procedure described in Example 20 using the compound resulting from Example 30 and hydroxylamine hydrochloride. MS (FAB) m/e 919 (M+K)$^+$.

EXAMPLE 39

Formula II: $R^0$=ethyl; $R^5$=—OH; m=0;$R^7$=—$CH_2$—CON$CH_3$OH

The protected title compound was prepared in 48% yield by the procedure described in Example 24 using N-methyl 0-t-butyldiphenylsilyl 2-bromo acetic acid amide, which was prepared from the protected hydroxylamine and bromoacetyl bromide.

The protected compound (0.2 g, 0.17 mmol) was deprotected with 48% aqueous HF (0.1 mL) in $CH_3CN$ over 2 hours. The tittle compound was collected from RP-HPLC. in 52% yield. MS (FAB) m/e 933 $(M+K)^+$.

EXAMPLE 40

Formula II: $R^0$=ethyl; $R^5$=—OH; m=0;$R^7$=—$CH_2$—$CH(CH_3)$—$CO_2CH_3$

The title compound was prepared in 14% yield by the procedure described in Example 8 substituting methyl methacrylate for phenyl acrylate and a catalytic amount of tetrabutylammonium floride for diisopropylethylamine. MS (FAB) m/e 946 $(M+K)^+$.

EXAMPLE 41

Formula II: $R^0$=ethyl; $R^5$=—OH; m=0;$R^7$=—$CH_2$—$CH(CH_3)$—$CO_2CH_2CH_3$

The title compound was prepared in 15% yield by the procedure described in Example 8 substituting ethyl methacrylate for phenyl acrylate and a catalytic amount of tetrabutylammonium fluoride for diisopropylethylamine. MS (FAB) m/e 960 $(M+K)^+$.

EXAMPLE 42

Formula II: $R^0$=ethyl; $R^5$—OH; m=0;$R^7$=—$CH_2$—$CH(CH_3)$—$CO_2$Benzyl.

The title compound was prepared in 30% yield by the procedure described in Example 8 substituting benzyl methacrylate for phenyl acrylate and a catalytic amount of tetrabutylammonium fluoride for diisopropylethylamine. MS (FAB) m/e 1022 $(M+K)^+$.

EXAMPLE 43

Formula II: $R^0$=ethyl; $R^5$—OH; m=0;$R^7$=—$CH_2$—$CH(CH_3)$—$CO_2H$

The title compound was prepared in 49% yield by the procedure described in Example 19 substituting the compound resulting from Example 40 for the compound resulting from Example 18. MS (FAB) m/e 932 $(M+K)^+$.

EXAMPLE 44

Formula II: $R^0$=ethyl; $R^5$=—OH; m=0;$R^7$=—$CH_2CH_2OH$

The title compound was prepared in 26% yield by the procedure described in Example 8 substituting 2-bromo ethanol for phenyl acrylate and reacting for two days at 75° C. MS (FAB) m/e 890 $(M+K)^+$.

EXAMPLE 45

Formula II: $R^0$=ethyl; $R^5$=—OH; m=0;$R^7$=—$CH_2$—$CH_2$—$CH_2$—OH

The title compound was prepared in 15% yield by the procedure described in Example 8 substituting 3-bromo-1-propanol for phenyl acrylate and reacting for two days at 80° C. MS (FAB) m/e 904 $(M+K)^+$.

EXAMPLE 46

Formula II: $R^0$=ethyl; $R^5$=—OH; m=0;$R^7$=—$CH_2$—$CH_2$-(4-Hydroxyphenyl)

The title compound was prepared in 20% yield by the procedure described in Example 8 substituting 4-hydroxyphenyl alcohol tosylate for phenyl acrylate and for a reaction time of four days at room temperature. MS (FAB) m/e 966 $(M+K)^+$.

EXAMPLE 47

Formula II: $R^0$=ethyl; $R^5$=—OH; m=0;$R^7$=-(4-Hydroxyphenyl)

A mixture of the compound resulting from Example 1 (0.97 g, 1.05 mmol), diisopropylethylamine (0.88 mL, 5.04 mmol) and 4-hydroxythiophenol (0.32 g, 2.52 mmol) in acetonitrile (15 mL) was stirred at room temperature overnight. The solvent was evaporated in vacuo, and the residue was partitioned between ethyl acetate and 10% $KHSO_4$. The ethyl acetate layer was washed with brine, dried over sodium sulfate and concentrated in vacuo to afford 1.07 g of crude product, which was purified by NP-HPLC. on a microsorb column eluting with 20:80 acetone-hexane to give 600 mg (63%) of the title compound. MS (FAB) m/e 938 $(M+K)^+$.

EXAMPLE 48

Formula II: $R^0$=ethyl; $R^5$=:OH; m=1;$R^7$=(4-Hydroxyphenyl)

To a solution of the compound resulting from Example 47 (0.5 g, 0.55 mmol) in $CH_2Cl_2$ at –5° C. was added cesium carbonate (0.18 g, 0.55 mmol) followed by 3-chloroperoxybenzoic acid (0.16 g, 0.55 mmol). After the reaction was stirred at –5° C. for 15 minutes, the reaction mixture was diluted with ethyl acetate and washed with saturated $NaHCO_3$ solution and brine, dried over $Na_2SO_4$ and concentrated. The crude product was further purified by NP-HPLC eluting with 50:50 acetone-hexane to give 237 mg of the title compound in 47% yield. MS (FAB) m/e 954 $(M+K)^+$

EXAMPLE 49

Formula II: $R^0$=ethyl; $R^5$=—OH; m=2;$R^7$=-(4-Hydroxyphenyl)

The title compound (113 mg) was isolated as a side reaction product in the preparation of Example 48. MS (FAB) m/e 970 $(M+K)^+$.

EXAMPLE 50

Formula II: $R^0$=ethyl; $R^5$=—OH; m=1;$R^7$=—$CH_2CH_2OH$

The title compound was prepared in 55% yield by the procedure described in Example 48 substituting the compound resulting for Example 44 for the compound resulting from Example 47. MS (FAB) m/e 906 $(M+K)^+$.

EXAMPLE 51

Formula II: $R^0$=ethyl; $R^5$=—OH; m=2;$R^7$=—$CH_2CH_2OH$

The title compound was isolated in 14% yield as a side reaction product in the preparation of Example 50. MS (FAB) m/e 922 $(M+K)^+$. Diagnostic chemical shifts: $^1H$ NMR ($C_5D_5N$, 300 MHz) δC31-OMe (3.39), $SO_2CH_2CH_2OH$ (3.97, 4.1).

EXAMPLE 52

Formula II: $R^0$=ethyl; $R^5$=—OH; m=1;$R^7$=—$CH_2CH_2CH_2OH$

The title compound was prepared in 28% yield by the procedure described in Example 48 substituting the compound resulting from Example 45 for the compound resulting from Example 47. MS (FAB) m/e 920 $(M+K)^+$.

EXAMPLE 53

Formula II: $R^0$=ethyl; $R^5$=—OH; m=2; $R^7$=—$CH_2CH_2CH_2OH$

The title compound was isolated in 16% as a side reaction product in the preparation of Example 52. MS (FAB) m/e 936 (M+K)$^+$.

EXAMPLE 54

Formula II: $R^0$=ethyl; $R^5$=—OH; m=1; $R^7$=—$CH_2CO_2Benzyl$

The title compound was prepared in 51% yield by the procedure described in Example 48 substituting the compound resulting from Example 27 for the compound resulting from Example 47. MS (FAB) m/e 1010 (M+K)$^+$.

EXAMPLE 55

Formula II: $R^0$=ethyl $R^5$=—OH: m=1; $R^7$=—$CH_2CO_2Benzyl$.

The title compound was isolated in 41% as an other isomer of the compound resulting from Example 54. MS (FAB) m/e 1010 (M+K)$^+$.

EXAMPLE 56

Formula II: $R^0$=ethyl; $R^5$=—OH; m=2; $R^7$=—$CH_2CO_2Benzyl$

The title compound was isolated in 6% as a side reaction product in the preparation of Example 54. MS (FAB) m/e 1026 (M+K)$^+$.

EXAMPLE 57

Formula II: $R^0$=ethyl; $R^5$=—OH; m=2; $R^7$=—$CH_2CO_2CH_3$

The title compound was prepared in 46% yield by the procedure described in Example 48 substituting the compound resulting from Example 28 for the compound resulting from Example 47 and using 200 mole percent of the oxidizing reagents at ambient temperature. MS (FAB) m/e 950 (M+K)$^+$. Diagnostic chemical shifts: 1H NMR ($C_5D_5N$, 300 MHz) δC31-OMe (3.35), $SO_2CH_2CO$ (4.51, 4.77), OMe (3.66).

EXAMPLE 58

Formula II: $R^0$=ethyl; $R^5$=—OH: m=2; $R^7$=—$CH_2CO_2C(CH_3)_3$

The title compound was prepared in 69% yield by the procedure described in Example 48 substituting the compound resulting from Example 29 for the compound resulting from Example 47 and using 200 mole percent of the oxidizing reagents at ambient temperature. MS (FAB) m/e 992 (M+K)$^+$. Diagnostic chemical shifts: 1H NMR ($C_5D_5N$, 300 MHz) δC31-OMe (3.34), $SO_2CH_2CO$(4.39, 4.66), t-Bu (1.47).

EXAMPLE 59

Formula II: $R^0$=ethyl; $R^5$=—OH; m=2; $R^7$=—$CH_2CO_2CH_2CH_3$

The title compound was prepared in 33% yield by the procedure described in Example 48 substituting the compound resulting from Example 31 for the compound resulting from Example 47 and using 200 mole percent of oxidizing reagents at ambient temperature. MS (FAB) m/e 964 (M+K)$^+$.

EXAMPLE 60

Formula II: $R^0$=ethyl; $R^5$=—OH; m=1; $R^7$=—$CH_2CO_2CH_2CH_3$

The title compound was prepared in 74% yield by the procedure described in Example 48 substituting the compound resulting from Example 10 for the compound resulting from Example 47. MS (FAB) m/e 962 (M+K)$^+$.

EXAMPLE 61

Formula II: $R^0$=ethyl; $R^5$=—OH; m=2; $R^7$=—$CH_2CO_2CH_2CH_3$

The title compound was isolated in 8% as a side reaction product in the prepration of Example 60. MS (FAB) m/e 978 (M+K)$^+$.

EXAMPLE 62

Formula II: $R^0$=ethyl; $R^5$=—OH; m=1; $R^7$=—$CH_2CH_2CO_2Benzyl$

The title compound was prepared in 22% yield by the procedure described in Example 48 substituting the compound resulting from Example 18 for the compound resulting from Example 47. MS (FAB) m/e 1024 (M+K)$^+$.

EXAMPLE 63

Formula II: $R^0$=ethyl; $R^5$=—OH; m=1; $R^7$=—$CH_2CH_2CO_2Benzyl$

The title compound was isolated in 34% as the other sulfoxide isomer of Example 62. MS (FAB) m/e 1024 (M+K)$^+$.

EXAMPLE 64

Formula II: $R^0$=ethyl; $R^5$=—OH; m=2; $R^7$=—$CH_2CH_2CO_2Benzyl$

The title compound was isolated in 7% as a side reaction product in the preparation of Examples 62. MS (FAB) m/e 1040 (M+K)$^+$.

EXAMPLE 65

Formula II: $R^0$=ethyl; $R^5$=—OH; m=1; $R^7$=—$CH_2CH_2CO_2CH(CH_3)_2$

The title compound was prepared in 29% yield by the procedure described in Example 48 substituting the compound resulting from Example 20 for the compound resulting from Example 47. MS (FAB) m/e 976 (M+K)$^+$.

EXAMPLE 66

Formula II: $R^0$=ethyl; $R^5$=—OH; m=1; $R^7$=—$CH_2CH_2CO_2CH(CH_3)_2$

The title compound was isolated in 33% as the other sulfoxide isomer of Example 24 1. MS (FAB) m/e 976 (M+K)$^+$.

EXAMPLE 67

Formula II: $R^0$=ethyl; $R^5$ =—OH; m=1; $R^7$=—$CH_2CH_2CO_2CH(CH_2CH_3)_2$

The title compound was prepared in 29% yield by the procedure described in Example 48 substituting the compound resulting from Example 21 for the compound resulting from Exampe 47. MS (FAB) m/e 1004 (M+K)$^+$.

EXAMPLE 68

Formula II: $R^0$=ethyl; $R^7$=—OH; m=1;$R^7$=—CH$_2$CH$_2$CO$_2$CH(CH$_2$CH$_3$)$_{12}$ The title compound was isolated in 56% as the other sulfoxide isomer of Example 67. MS (FAB) m/e 1004 (M+K)$^+$.

EXAMPLE 69

Formula II: $R^0$=ethyl; $R^5$=—OH; m=1;$R^7$=—CH$_2$CH$_2$CON(OH)CH$_3$

The 0-t-butyldiphenylsilyl protected title compound was prepared in yield by the procedure described in Example 48 substituting the compound resulting from the protected precursor of Example 25 for the compound resulting from Example 47.

The title compound was prepared in 53% yield by deprotection of the above compound by the procedure described in Example 25. MS (FAB) m/e 963 (M+K)$^+$.

EXAMPLE 70

Formula II: $R^0$=ethyl: R&=—OH; m=1;$R^7$=—CH$_2$CH$_2$CON(OH)CH$_3$

The other sulfoxide isomer of the O-t-butyldiphenylsilyl protected title compound was isolated in 62% from the procedure used to prepare Example 69.

The title compound was prepared by deprotection of the above isomer in 54% yield by the procedure described in Example 25. MS (FAB) m/e 963 (M+K)$^+$.

EXAMPLE 71

Formula II: $R^0$=ethyl; $R^5$=—OH; m=1; $R^7$=—CH$_2$CH$_2$CON(OH)CH(CH$_3$)$_{12}$ The 0-t-butyldiphenylsilyl protected title compound was prepared in 32 % yield by the procedure described in Example 48 substituting the protected compound from Example 26 for the compound resulting from Example 47.

The title compound was prepared in 60% yield by deprotection of the above compound by the procedure described in Example 26. MS (FAB) m/e 991 (M+K)$^+$.

EXAMPLE 72

Formula II: $R^0$=ethyl; $R^5$=OH; m=1;$R^7$=—CH$_2$CH$_2$CON(OH)CH(CH$_3$)$_2$

The other sulfoxide isomer of the O-t-butyldiphenylsilyl protected title compound was isolated in 59% from the procedure used to prepare Example 71.

The title compound was prepared by deprotection of of the above compound by the procedure described in Example 26 in 60% yield. MS (FAB) m/e 991 (M+K)$^+$.

EXAMPLE 73

Formula II: $R^0$=ethyl; $R^5$=—OH; m=1;$R^7$=—CH$_2$CO$_2$H

The title compound was prepared by the procedure described in Example 19 substituting the compound resulting from Example 54 for the compound resulting from Example 18. The hydrogenation time was 45 minutes, and the yield was 55%. MS (FAB) m/e 920 (M+K)$^+$.

EXAMPLE 74

Formula II: $R^0$=ethyl; $R^5$—OH; m=1;$R^7$=—CH$_2$CO$_2$H

The title compound which is the other sulfoxide isomer of Example 73 was prepared by the procedure described in Example 19 substituting the compound resulting from Example 55 for the compound resulting from Example 18. The hydrogenation time was 45 minutes, and the yield was 55%. MS (FAB) m/e 920 (M+K)$^+$.

EXAMPLE 75

Formula II: $R^0$=ethyl; $R^5$=—OH; m=2;$R^7$=—CH$_2$CO$_2$H

The title compound was prepared by the procedure described in Example 19 substituting the compound resulting from Example 56 for the compound resulting from Example 18. The hydrogenation time was 45 minutes, and the yield was 41%. MS (FAB) m/e 936 (M+K)$^+$. Diagnostic chemical shifts: $^1$H NMR (C$_5$D$_5$N, 300 MHz) δC31-OMe (3.4,SO$_2$CH$_2$COOH (4.42, 4.46, 4.51, 4.72).

EXAMPLE 76

Formula II: $R^0$=ethyl; $R^5$=—OH; m=1;$R^7$=—CH$_2$CH$_2$CO$_2$H

The title compound was prepared by the procedure described in Example 19 substituting substituting the compound resulting from Example 62 for the compound resulting from Example 18. The hydrogenation time was 45 minutes, and the yield was 63%. MS (FAB) m/e 934 (M+K)$^+$.

EXAMPLE 77

Formula II: $R^0$=ethyl; $R^5$=—OH; m=1;$R^7$=—CH$_2$CH$_2$CO$_2$H

The title compound which is the other sulfoxide isomer of Example 76 was prepared by the procedure described in Example 19 substituting the compound resulting from Example 63 for the compound resulting from Example 18. The hydrogenation time was 45 minutes, and the yield was 56%. MS (FAB) m/e 934 (M+K)$^+$.

EXAMPLE 78

Formula II: $R^0$=ethyl: $R^5$=—OH; m=2;$R^7$=—CH$_2$CH$_2$CO$_2$H

The title compound was prepared by the procedure described in Example 19 substituting the compound resulting from Example 64 for the compound resulting from Example 18. The hydrogenation time was 45 minutes, and the yield was 34%. MS (FAB) m/e 950 (M+K)$^+$.

EXAMPLE 79

Formula II: $R^0$=ethyl; $R^5$=—OH; m=0;$R^7$=-Allyl

To the compound resulting from Example 8A (640 rag, 0.793 mmol) in 2 mL of CH$_3$CN was added 2 equivalents (137 gL) of allyl bromide. The reaction mixture was stirred overnight at room temperature and then Hünig's base (140 μL) was added. The reaction mixture was heated to reflux. After ~1 hour, the solvent was removed under reduced pressure to afford 1.1 g of crude material. Purification by column chromatography on silica gel eluting with 15% acetone in hexane afforded the title compound. MS (FAB) m/e 887 (M+K)$^+$. Anal calcd for C$_{46}$H$_{73}$NO$_{11}$S: C, 65.14;H, 8.68;N, 1.65. Found: C, 64.82;H, 8.74;N, 1.66. $^{13}$C NMR (CDCl$_3$) δ213.5,213.5(22), 196.2,192.4(9),168.9,168.6(1), 165.8, 164.7(8), 139.5,138.6(19), 134.8(monosubstituted allyl olefinic C), 131.8,131.3(27), 129.6(28), 123.2,122.9(20), 116.6,116.6(terminal olefinic allyl C), 98.5,96.8(10), 80.6,80.6(31), 77.4,76.7(26), 76.6,75.1(15), 73.6,73.5(13), 72.8,72.0(14), 70.1,69.3(24), 57.3,56.8(15OMe), 56.6, 56.2, 56.0 (31OMe, 2, 13OMe), 55.9(32), 54.8,54.6(21), 52.6(2), 48.5,48.3(18), 43.7,39.1(6), 43.1,42.7(23), 39.9,39.4(25), 35.5,32.5(16), 35.0(29), 34.6(30), 34.5,3 33.7,33.5(12), 32.7(33), 29.4(34), 27.6,26.0(3), 26.8(allylic $CH_2$), 26.3, 25.9(17), 24.5,24.5, 24.4,24.1 (5,35), 21.0,20.7(4), 20.4,19.3(17Me), 16.1,15.9(19Me), 15.7,15.6(11Me), 14.2,14.1(27Me), 11.6(36), 9.6,9.2(25Me). IR ($CHCl_3$) 3580,2920, 2880(shoulder), 2820(sh), 1740,1700,1650,1450 $cm^1$.

EXAMPLE 80

Formula II: $R^0$=ethyl; $R^5$=—OH; m=0;$R^7$=—$CH_2$—C(O)—$CH_3$

To the compound resulting from Example 8A (5.05 g) in $CH_3CH_3$ was added Hünig's base (diisopropylethylamine) followed by (2.5 equivalents) of chloroacetone. After ~2 hours at room temperature, the solvent was removed under reduced pressure. Purification by column chromatography on silica gel eluting with 25% acetone in hexane afforded 4 g of title compound. A portion of the product was further purified by NP-HPLC. on a microsorb column eluting with 28:72 acetone-hexane. m.p. 84°–87° C. MS (FAB) m/e 902 $(M+K)^+$. Anal calcd for $C_{46}H_{73}N_2O_{12}S$: C, 63.94;H, 8.51;N, 1.62. Found: C, 63.58;H, 8.64; N, 1.54.$^{13}$C NMR ($CDCl_3$) δ213.6,213.5(22), 205.5,205.4(acetone carbonyl C), 196.2, 192.4(9), 169.0,168.6(1), 165.8,164.7(8), 139.6,138.7(19), 132.1,131.6(27), 129.6,129.5(28), 123.2,123.0(20), 98.6,96.9(10), 80.7(31), 77.5,76.9(26), 76.6,75.2(15), 73.6, 73.6(13), 72.9,72.1(14), 70.1,69.2(24), 57.4,56.9(15OMe), 56.0(32), 54.9,54.6(21), 52.6(2), 48.5,48.4(18), 45.9, 45.8(acetone methyl C), 43.8,39.2(6), 43.3,42.9(23), 42.0(acetone methylene C), 40.0,39.5(25), 35.5,32.8(16), 34.9(29), 34.5,33.5(11), 33.2(30) 32.7,32.5(12), 29.3(34), 27.7(33), 27.6,26.2(3), 26.9(33),26.3,25.9(17) 24.6,24.5,24.1(5,35), 21.0,20.7(4), 20.4,19.4(17Me), 16.1, 15.9(11Me), 15.8,15.6(19Me), 14.2,14.0(27Me), 11.6(36), 9.7,9.3(25Me). IR ($CHCl_3$) 3440,2920,1740,1700,1650,1450 $cm^1$.

EXAMPLES 81A and 81B

Formula II: $R^0$=ethyl; $R^5$—OH; m=0;$R^7$=—$CH_2$-($CH_3$)C=N—NH—C(O)—$NH_2$

To the compound resulting from Example 80 (600 rag, 0.695 mmol) in 3.5 mL EtOH was added a solution of 89 mg of semicarbazide hydrochloride in 3 mL of EtOH followed by 146 δL of $Et_3N$. The reaction mixture was stirred 3 hours at room temperature and then additional aliquots of $Et_3N$ (7.3 μL, 0.75 equivalents) and semicarbazide hydrochloride (58 rag) were added. After 7 hours at room temperature, the solvents were removed under reduced pressure. The residue obtained was purified by column chromatography on silica gel eluting with 1:1 acetone-hexane to give 156 mg of 81A and 390 mg of the isomeric 81B. The 81B fraction was further purified by NP-HPLC. on a microsorb column eluting with 55% going to 62% acetone in hexane.

For compound 81A: m.p. 140°–145° C. MS (FAB) m/e 959 $(M+K)^+$. Anal calcd for $C_{49}H_{76}N_4O_{12}S$: C, 61.28;H, 8.32;N, 6.08. Found: C, 61.36;H, 8.21;N, 5.90. $^{13}$C NMR ($CDCl_3$) δ213.5(22), 196.3(9), 169.0,168.7(1), 165.8, 164.8(8), 157.5(semicarbazone carbonyl C), 147.2(semicarbazone imine C), 139.6,138.7(19), 132.0131.5(27), 129.7, 129.6(28), 123.2,123.0(20), 98.6,97.0(10), 80.7,80.5(31), 77.6,77.1(26), 76.6,75.2(15), 73.7(13), 72.9,72.1(14), 70.1, 69.2(24), 57.4,56.9(15OMe), 56.3(13OMe), 56.0(32), 54.9, 54.7(21), 52.6(2), 48.6,48.4(18), 44.9(acetone methyl C), 43.8,39.2(6), 43.4,43.1 (23), 40.1,39.5(25), 39.3(acetone methylene C), 35.5,32.9(16), 34.9(29), 34.6,33.5(11), 33.7(30), 32.7,32.5(12), 29.5(34),27.6,26.2(3) 26.9(33), 26.3,26.0(17), 24.6,24.5,24.2(5,35), 21.1,20.7(4), 20.4,19.4(17Me), 16.2,16.0(11Me), 15.8,15.7(19Me), 14.0, 14.2(27Me), 11.6(36), 9.7,9.4(25Me). IR ($CHCl_3$) 3580, 2930,1740,1700,1650,1570,1450 $cm^{-1}$.

For compound 81B: m.p. 155°–160° C. MS (FAB) m/e 959 $(M+K)^+$. Anal calcd for $C_{49}H_{76}N_4O_{12}S$ . 0.25 $H_2O$: C, 60.98;H, 8.32;N, 6.05. Found: C, 60.70;H, 8.30;N, 5.72. $^{13}$C NMR ($CDCl_3$) δ213.5 (C22), 196.3,192.6(9), 169.0,168.7(1), 165.8,164.8(8), 157.6(semicarbazone carbonyl C), 147.2(semicarbazone imine C), 139.6,138.6(19), 132.0,131.5(27), 129.7,(28), 123.2,123.0(20), 98.6,97.0(10), 80.5(31), 77.6,77.1(26), 76.6,75.2(15), 73.6(13) 72.9,72.1(14), 70.1,69.2(24), 57.4,56.9(15OMe), 56.3(13OMe), 54.9,54.7(21), 52.6(2), 48.6,48.3(18), 44.9, 44.9(acetone methyl C), 43.8,39.2(6), 43.4,43.1(23), 40.1, 39.5(25), 39.3(acetone methylene C), 35.5,32.9(16), 35.0(29), 34.5,33.5(11), 33.7(30), 32.7,32.5(12), 29.5(34), 27.6,26.2(3), 26.9(33 ), 26.3,26.0(17), 24.6,24.524.4,24.2(5, 35), 21.0,20.7(4), 20.4,19.4(17Me), 16.1,15.9(11Me), 15.8, 15.7(19Me), 14.2,14.0(27Me), 11.6(36), 99.7,9.3(25Me).

EXAMPLE 82

Formula II: $R^0$=ethyl; $R^5$=—OH; m=0;$R^7$=—$CH_{22}$—($CH_3$)C=N—O—$CH_3$

To a solution of the compound resulting from Example 80 (600 rag) in 3 mL of EtOH was added dropwise a solution of 61 mg of methoxylamine hydrochloride and 112 μL $Et_3N$ in 2 mL of ethanol. After stirring at room temperature for 2 hours, additional aliquots of $Et_3N$ (29 μL) and methoxylamine hydrochloride (14.5 rag, 0.25 equivalents) were added. After stirring an additional 2 hours at room temperature, 0.25 equivalents of $Et_3N$ and methoxylamine hydrochloride were added. After stirring an additional hour at room temperature, the solvents were removed in vacuo. The residue obtained was filtered through a silica gel plug eluting with 1:1 acetone-hexane to give 675 mg of partially purified material. This material was further purified by NP-HPLC on a microsorb column eluting with 23% acetone in hexane to afford the title compound as a mixture of isomers. m.p. 82°–85° C. MS (FAB) m/e 931 $(M+K)^+$. Anal calcd for $C_{47}H_{76}N_2O_{12}S$: C, 63.20;H, 8.57;N, 3.13. Found: C, 63.16;H, 8.42;N, 2.99. $^{13}$C NMR ($CDCl_3$) δ213.6,213.5(22), 196.2,192.3(9), 168.9,168.6(1), 165.8,164.7 (8), 154.6, 154.6(oxime quantenary CO, 139.6,138.6(19), 132.0,131.4(27), 129.6,128.2(28), 123.2,122.9(20), 98.6,96.9(10), 80.3(31), 77.4,76.7(26), 76.6,75.1(15), 73.6, 73.6(13), 72.8,72.1(14), 70.1,69.3(24), 61.4,61.1(oxime 0-methyl), 57.4,56.8(15OMe), 55.9(32), 54.9,54.6(21), 52.6(2), 48.5,48.3(18), 44.7,44.7(methyl alpha to oxime quant. C), 43.7,39.1(6), 43.2,42.7(23), 39.9,39.4(25), 36.2(methylene alpha to oxime quant. C), 35.5(16), 34.9(29), 34.5,33.4(11), 32.7,32.5(12), 29.4,29.1(34) 27.6, 25.9(3), 27.0(33), 26.3,25.9(17), 24.6,24.5,24.4,24.1(5,35), 21.0,20.7(4) 20.4,19.4(17Me), 16.1,15.9(11Me), 15.8,15.6(19Me), 14.2,14.1(27Me), 11.6(36), 9.6,9.2(25Me). IR ($CHCl_3$) 3460,2940,1740,1700,1650,1450 $cm^{-1}$.

EXAMPLES 83A and 83B

Formula II: $R^0$=ethyl; $R^7$=—OH; m=0;$R^7$=—$CH_2$—($CH_3$)C=N—OH

To a solution of the compound resulting from Example 80 (600 mg) in 3 mL of EtOH was added a solution of 53 mg of hydroxylamine hydrochloride and 112 μL of $Et_3N$ in 4 mL of ethanol. After stirring overnight at room temperature, MgSO$_4$ was added. After 3 hours, additional hydroxylamine hydrochloride (24 mg, 0.55 equivalents) in 1 mL of EtOH and 75 μL of Et$_3$N were added. After an additional hour of stirring at room temperature, an additional aliquot of 6 mg of hydroxylamine hydrochloride was added. After 2 more hours, insoluble material was removed by filtration and the flitrate concentrated in vacuo. The crude material obtained was passed through a plug of silica gel eluting with 40% acetone in hexane to afford 685 mg of partially purified product. This material was further purified by NP-HPLC. on a microsorb column eluting with 30% acetone in hexane to afford the title compound as two isomers (188 mg of 83A and 180 mg of 83B).

For compound 83A: m.p. 114°–116° C. MS (FAB) m/e 917 (M+K)$^+$. Anal calcd for C$_{46}$H$_{74}$N$_2$O$_{12}$S: C, 62.84;H, 8.48;N, 3.18. Found: C, 62.47;H, 8.45;N, 3.03. $^{13}$C NMR (CDCl$_3$) δ213.7,213.6(C22), 196.2,192.5(9), 169.0,168.6(1), 165.9,164.7(8), 155.7,155.7(38), 139.6,138.7(19), 131.9,131.4(27), 129.7,129.6(28), 123.2, 122.9(20), 98.6,96.9(10), 80.4,80.4(31), 77.5,76.9(26), 76.7, 75.2(15), 73.7,73.6(13), 72.9,72.1(14), 70.1,69.3(24), 57.4, 56.9(15OMe), 54.9,54.6(21), 52.6(2), 48.5,48.3(18), 44.7, 44.7(acetone methyl-alpha to oxime), 43.8,39.2(6), 43.3, 42.9(23), 39.6,39.4(25), 36.2(acetone methylene-alpha to oxime), 35.6,32.8(16), 34.9(29), 34.5,33.5(11), 33.9,33.8(30?), 32.7,32.5(12), 29.4(34), 27.6,26.2(3), 27.0, 27.0(33), 26.3,26.0(17), 24.6,24.5,24.5,24.1(5,35), 21.0,20.7(4), 20.4,19.4(17Me), 16.1,15.9(11Me), 15.8,15.6(19Me), 14.2,14.0(27Me), 11.6,11.6(36), 9.7,9.3(25Me). IR (CHCl$_3$) 3440,2930,1740,1710,1650,1450 cm$^{-1}$.

For compound 83B: m.p. 110°–112° C. MS (FAB) m/e 917 (M+K)$^+$. Anal calcd for C$_{46}$H$_{74}$N$_2$O$_{12}$S: C, 62.84;H, 8.48;N, 3.18. Found: C, 62.47;H, 8.45;N, 3.03.$^{13}$C NMR (CDCl$_3$) δ 213.6,213.6(C22), 196.2,192.5(9), 169.0,168.6(1), 165.9,164.7(8), 155.7,155.7(oxime quantenary C), 139.6,138.7(19), 131.9,131.4(27), 129.8,129.7(28), 123.2,123.0(20), 98.6,96.9(10), 80.3,80.3(31), 77.5,76.9(26), 76.7,75.2(15), 73.7(13), 72.9,72.1(14), 70.1, 69.2(24), 57.4,56.9(15OMe), 54.9,54.6(21), 52.6(2), 48.5, 48.3(18),46.0,45.9(acetone methyl ), 43.8,39.2(6), 43.3,43.0(23), 40.0,39.5(25), 35.6,32.8(16), 34.9(29), 34.5, 33.5(11), 33.7,33.6(30?), 32.7,32.5(12), 29.3(34), 27.6,26.2(3), 27.0(33?), 26.3,26.0(17), 24.6,24.5,24.4,24.2(5,35), 21.0,20.7(4), 20.4,19.4(17Me), 16.1,15.9(11Me), 15.8,15.7(19Me), 14.2,14.0(27Me), 11.6(36), 9.7,9.3(25Me). IR (CHCl$_3$) 3440,2930,1740,1710, 1650,1450 cm$^{-1}$.

EXAMPLE 84

Alternate Preparation of
Formula II: R$^0$=ethyl; R$^5$=—OH; m=0;R$^7$=-Acetyl

To the compound resulting from Example 8A (500 mg, 0.619 mmol) in 5 mL of methylene chloride was added diisopropylethylamine (4 equivalents, 348 μL) at 0° C. and acetyl chloride (85 μL, 2 equivalents) over one minute. The reaction solution was stirred at 0° C. for 5 minutes and then was allowed to stir at room temperature for 2 hours. The reaction was then concentrated under reduced pressure and dried to constant weight to provide 850 mg of crude product. Purification by silica gel column chromatography eluting with 25% acetone in hexane gave 498 mg of the title compound. m.p. 93°–95° C. MS (FAB) m/e 888 (M+K)$^+$. Anal calcd for C$_{45}$H$_{71}$NO12S: C, 63.57;H, 8.41;N, 1.64. Found: C, 63.31;H, 8.46;N, 1.58. $^{13}$C NMR (CDCl$_3$) δ213.4, 213.3(C22), 196.1,192.5(9), 194.9,194.8(acetyl carbonyl), 168.9,168.6(1), 165.7,164.7(8), 139.5,138.6(19), 132.3,131.8(27), 129.5,129.4(28), 123.2,123.0(20), 98.6,96.9(10), 78.6(31), 77.6,77.1(26), 76.6,75.1(15), 73.6, 73.6(13), 72.8,72.2(14), 70.0,69.1(24), 57.4,56.9(15OMe), 54.9,54.6(21), 52.6(2), 48.6,48.3(18), 43.9,43.8(32), 43.8, 39.1(6), 43.4,43.0(23), 40.1,39.5(25), 35.7,32.8(16), 34.6(29), 34.5,33.5(11), 32.6,32.5(12), 30.9(acetate methyl) 29.8(34), 28.1(33), 27.7,26.2(3), 26.3,26.0(17), 24.5,24.5, 24.4,24.1(5,35), 21.0,20.7(4), 20.4,19.4(17Me), 16.1,15.9(11Me), 15.7,15.6(19Me), 14.1,13.9(27Me), 11.6(36), 9.7,9.3(25Me).

EXAMPLE 85

Formula II: R$^0$=ethyl; R$^5$=—OH; m=0; R$^7$=-Pivaloyl

The title compound was prepared using the procedures described in
Example 80 and substituting pivaloyl chloride for chloroacetone and running the reaction at 0° C. for ~1 hour and at room temperature for 2 hours. The crude material was purified by chromatography on silica gel eluting with 15% acetone in hexane to afford the title compound. m.p. 116°–118° C. MS (FAB) m/e 930 (M+K)$^+$. Anal calcd for C$_{48}$H$_{77}$NO$_{12}$S: C, 64.61;H, 8.69;N, 1.56. Found: C, 64.60;H, 8.63;N, 1.63.$^{13}$C NMR (CDCl$_3$) δ213.4,213.3 (C22), 205.9, 205.9(acetyl carbonyl), 196.1,192.5(9),168.9, 168.6(1), 165.8,164.7(8), 139.5,138.6(19), 132.1,131.7(27), 129.8,129.6(28), 123.2,123.0(20), 98.6,97.0(10), 78.7,78.7(31), 77.7,77.2(26), 76.6,75.2(15), 73.6,73.6(13), 72.89,72.1(14), 70.0,69.2(24), 57.4,56.9(15OMe), 54.7,54.9(21), 52.6(2), 48.6,48.3(18), 46.7(quantenary acetyl C), 43.8,39.1(6), 43.4,43.1(23), 43.0(32), 40.1,39.5(25), 35.8,32.9(16), 34.6(29), 34.5,33.5(11), 32.6, 32.5(12), 26.7) 28.1,28.0(33), 27.6,26.2(3), 27.3((acetyl trimethyl carbons), 26.3,26.0(17), 24.5,24.5,234.4,24.1(5,35), 21.0,20.7(4), 20.4,19.4(17Me), 16.1,15.9(11Me), 15.7,15.6(19Me), 14.1,13.9(27Me), 11.6,11.6(36), 9.7,9.4(25Me). IR (CHCl$_3$) 50,2920,2960(shoulder), 2880(sh),2820(sh), 1740,1700,1680,1650,1450 cm$^{-1}$.

EXAMPLE 86

Formula II: R$^0$=ethyl; R$^5$=—OH; m=0;R$^7$=-Isobutyryl.

The title compound was prepared using the procedures described in Example 80 and substituting isobutyryl chloride for chloroacetone and running the reaction at 0° C. for ~1 hour and at room temperature for 2 hours. The crude material was purified by chromatography on silica gel eluting with 15% acetone in hexane to afford the title compound. MS (FAB) m/e 916 (M+K)$^+$. Anal calcd for C47H$_{75}$NO$_{12}$S: C, 64.28;H, 8.61;N, 1.59. Found: C, 63.99;H, 8.50;N, 1.82. Diagnostic Chemical Shifts: $^{13}$C NMR (CDCl$_3$) δ78.6,78.6 (C31), 43.1 (C32), side chain C's: SCO (203.1,203.1), CH (43.4), CH$_3$ (19.2), CH$_3$ (19.2). IR (CHCl$_3$) 3480,2960(shoulder),2930,2880(sh),2820(sh), 1740,1680,1650,1450 cm$^{-1}$.

EXAMPLE 87

Formula II: R$^0$=ethyl; R$^5$=—OH; m=0;R$^7$=-Benzoyl

The title compound was prepared using the procedures described in Example 80 and substituting benzoyl chloride for chloroacetone and running the reaction at 0° C. for ~1 hour and at room temperature for 2 hours. The crude material was purified by chromatography on silica gel eluting with 18% acetone in hexane to afford the title compound. MS (FAB) m/e 950 (M+K)$^+$. Anal calcd for $C_{50}H_{73}NO_{12}S$: C, 65.84;H, 8.07;N, 1.54. Found: C, 65.52;H, 7.70;N, 1.47. Diagnostic Chemical Shifts: $^{13}C$ NMR (CDCl$_3$) δ78.7 (C31), 43.9,43.8 (C32), side chain C's: SCO (191.0, 190.9), Ph (137.2-q, 133.2, 128.4-two C's, 127.2-two C's). IR (CHCl$_3$) 3480,2930,2820(sh),1740, 1710,1650,1450 cm$^{-1}$.

EXAMPLE 88

Formula II: $R^0$=ethyl; $R^5$=—OH; m=0;$R^7$=-Propionyl

The title compound was prepared using the procedures described in Example 80 and substituting propionyl chloride for chloroacetone and running the reaction at 0° C. for 30 minutes and at room temperature for 2.5 hours. The crude material was purified by chromatography on silica gel eluting with 15% acetone in hexane to afford the title compound. MS (FAB) m/e 902 (M+K)$^+$. Anal calcd for $C_{46}H_{73}NO_{12}S$: C, 63.93;H, 8.51;N, 1.62. Found: C, 63.92;H, 8.47;N, 1.63. Diagnostic Chemical Shifts: $^{13}C$ NMR (CDCl$_3$) δ78.6, 78.6 (C31), 43.4, 43.3 (C32), side chain C's: SCO(196.1), CH$_2$ (37.7), CH$_3$ (9.5). IR (CHCl$_3$) 3480,2920,2820(sh), 1740,1690,1650,1450 cm$^{-1}$.

EXAMPLE 89

Formula II: $R^0$=ethyl; $R^5$=—OH; m=2;$R^7$=—OH

To the compound resulting from Example 8A (1 g) in 10 mL of anhydrous methylene chloride was added 1.2 g of ground cesium carbonate. The reaction mixture was stirred at room temperature for 10 minutes and then cooled to 0° C. m-Chloroperbenzoic acid (1.2 g of ~50%) was added in portions over 15 minutes at 0° C. After an additional 15 minutes at 0° C, the reaction was complete. Cysteine methyl ester hydrochloride was added and stirring was continued to quench the excess m-chloroperbenzoic acid maintaing the temperature at 0° C. The reaction mixture was filtered cold through a bed of Celite and concentrated in vacuo. The residue obtained was filtered through a silica gel plug eluting with 30% isopropanol in methylene chloride. The partially purified material was further purified on RP-HPLC. MS (FAB) m/e 894 (M+K)$^+$, 932 (M+2K)$^+$.

EXAMPLE 90

Formula II: $R^0$=ethyl; $R^5$=—OH; m=0;$R^7$=—CH$_3$

A solution of 80% sodium hydride (106 mg) was heated in 10 mL of isopropanol at 60° C. until complete dissolution. To this solution cooled to −23° C. was added 1 g of 32-epi-thiol Ascomycin. The reaction mixture was allowed to warm to 0° C. and stirred for 10 minutes until the reaction mixture was homogeneous. To the reaction mixture recooled to −23° C. was added methyl trifluoromethanesulfonate (250 μL, 1.8 equivalents). After approximately 30 minutes, the reaction mixture was partitioned between water and ethyl acetate. The organic phase was washed with brine, dried over magnesium sulfate and concentrated in vacuo. The residue obtained was filtered through a plug of silica gel eluting with 30% acetone in hexane to give partially purified material. This material was further purified by NP-HPLC on a microsorb column eluting with 20% acetone in hexane to afford the title compound. MS (FAB) m/e 861 (M+K)$^+$. $^{13}C$ NMR (CDCl$_3$) δ213.6,213.5(C22), 196.2,192.3(9), 169.0, 168.6(1), 165.8,164.7(8), 139.6,138.7(19), 131.9,138.7(27), 129.7,129.6(28), 123.2,122.9(20), 98.6,96.9(10), 81.0,80.9(31), 77.4,76.7(26), 76.6,75.1(15), 73.6,73.6(13), 72.9,72.1(14), 70.1,69.3(24), 57.4,56.8(15OMe), 56.6,56.3, 56.0(31OMe, 13OMe,2)55.9(32), 54.9,54.6(21), 52.6(2), 48.5,48.3(18), 47.7,47.7(S-methyl), 43.7,39.1(6), 43.2,42.7(23), 39.9,39.4(25), 35.5,32.5(16), 35.0(29), 34.5, 33.4(11), 33.3,33.2(12), 32.7,28.8,26.6(30,33,34), 27.6,26.1(3), 26.3,25.9(17), 24.624.524.5,24.1(5,35), 21.0, 20.7(4), 20.5,19.4(17Me), 16.1,15.9(11Me), 15.8,15.6(19Me), 14.2,14.1(27Mer), 11.6(36), 9.7,9.2(25Me). IR (CHCl$_3$) 3450,2940,2830(sh), 1740,1710(sh), 1650,1450 cm$^{-1}$.

EXAMPLE 91

Formula II: $R^0$=ethyl; $R^5$=—OH; m=0;$R^7$=—C(O)—NH—CH$_2$CH$_3$

To a room temperature solution of the compound resulting from Example 8A (500 mg, 0.619 mmol) in 5 mL of methylene chloride was added 4 equivalents of diisopropylethylamine followed by 1.3 equivalents of ethyl isocyanate. The solution was stirred for two hours, and the solvent was removed under reduced pressure to afford 630 mg of crude product. Purification by column chromatography on silica gel eluting with 25% acetone in hexane gave 400 mg of the title compound. MS (FAB) m/e 917 (M+K)$^+$. $^{13}C$ NMR (CDCl$_3$) δ213.3,213.2(C22), 196.2,192.6(9), 168.9,168.6(1), 166.2(carbamoyl carbonyl C), 165.7,164.7(8), 139.5,138.5(19), 132.0,131.6(27), 129.9,129.6(28), 123.2,123.0(20), 98.5,96.9(10), 78.9(31), 77.6,77.4(26), 76.6,75.1(15), 73.6,73.5(13), 72.8,72.1(14), 69.9,69.1(24), 57.3,56.8(15OMe), 56.5,56.2,56.0,56.0,55.9(31OMe, 13OMe,2), 54.8,54.6(21), 52.5(2), 48.5,48.2(18), 45.2(32), 43.7,39.1(6), 43.4,43.2(23), 40.1,39.5(25), 36.2(carbamoyl ethyl methylene C), 35.4(30), 35.3,32.9(16), 34.6(29), 34.5,33.4(11), 32.6,32.4(12), 30.5(34), 28.0,28.0(33), 27.5,26.1(3), 26.2, 25.9(17), 24.5,24.4,24.4,24.1 (5,35), 20.9,20.7(4), 20.3,19.4(17Me), 16.1,15.9(11Me), 15.6,15.6(19Me), 14.8(carbamoyl methyl C), 14.0,13.7(27Me), 11.6,11.5(36), 9.6,9.3(25Me).

EXAMPLE 92

Formula II: $R^0$=ethyl; $R^5$=—OH; m=0;$R^7$=—C(O)—NH—CH$_2$CH$_2$CH$_3$

The title compound was prepared using the procedure described in Example 91 and substituting propyl isocyanate for ethyl isocyanate. MS (FAB) m/e 931 (M+K)$^+$. $^{13}C$ NMR (CDCl$_3$) δ213.4,213.3(C22), 196.2,192.5(9), 168.90,168.6(1), 165.8,164.7(8), 139.6,138.6(19), 132.1,131.7(27), 129.9,129.6(28), 132.2,132.0(20), 98.6,96.9(10), 79.0(31), 77.7,77.3(26), 76.6,75.2(15), 73.6, 73.6(13), 72.8,72.2(14), 70.0,69.2(24), 57.4,56.9(15OMe), 56.6,56.2,56.1,56.0(31OMe,13OMe, 2), 545.9,54.7(21), 52.6(2), 48.6,48.3(18), 45.3(32), 43.8,39.1(6), 43.4,43.2(23), 43.1(alpha methylene of propyl grp of carbamate), 40.2,39.6(25), 35.5(30), 35.4,32.9(16), 34.7(29), 34.5,33.5(11), 32.7,32.5(12), 30.5(34), 28.1(33 or 30?), 27.6,26.2(3), 26.3,26.0(17), 24.5,24.5,24.4,24.1 (5,35), 22.9(beta methylene of propyl grp of carbamate), 21.0, 20.7(4), 20.4,19.4(17Me), 16.1,15.9(11Me), 15.7,15.6(19Me), 14.1,13.8(27Me), 11.6,11.6(36), 11.2(methyl C. of propyl grp of carbamate), 9.7,9.3(25Me). IR (CHCl$_3$) 3440, 2920, 2940 (shoulder), 2880 (sh), 2820 (sh), 1740, 1650, 1450 cm$^{-1}$.

EXAMPLE 93

Formula II: $R^0$=ethyl; $R^5$=—OH; m=0;$R^7$=—C(O)—NH—CH(CH$_3$)$_2$

The title compound was prepared using the procedure described in Example 91 and substituting isopropyl isocyanate for ethyl isocyanate. MS (FAB) m/e 931(M+K)$^+$. $^{13}C$ NMR (CDCl$_3$) δ213.4,213.2(C22), 196.2,192.6(9), 168.9, 168.6(1), 165.7,164.7(8), 165.4(carbamate carbonyl), 139.5, 138.6(19), 132.0,131.6(27), 129.9,129.5(28), 123.2,123.0(20), 98.5,96.9(10), 79.0(31), 77.6,77.3(26), 76.6,75.1(15), 73.6,73.5(13), 72.8,72.1(14), 70.0,69.1(24), 57.3,56.8(15OMe), 56.5,56.2,56.1,55.9(31OMe, 13OMe, 2)54.8,54.6(21), 52.5(2), 48.6,48.3(18), 45.2(32), 43.7,39.1(6), 43.7(isopropyl methine C.), 43.4,43.2(23), 40.1,39.5(25), 35.4(30), 35.3,32.9(16), 34.7(29), 34.5,33.5(11), 32.6,32.5(12), 30.5(33 ? or 30?)27.6,26.1(3), 26.2,25.9(17), 24.5,24.4,24.4,24.1(5,35), 22.6(isopropyl methyl C's), 21.0,20.7(4), 20.3,19.4(17Me), 16.1,15.9(11Me), 15.7,15.6(19Me), 14.1,13.8(27Me), 11.6, 11.6(36), 9.6,9.3(25Me). IR (CHCl$_3$) 3480, 3320, 2920, 2960 (shoulder), 2880(shoulder), 2820 (shoulder), 1740, 1700, 1650, 1510 (wk), 1450cm$^{-1}$.

EXAMPLE 94

Formula II: R$^0$=ethyl; R$^5$=—OH; m=0;R$^7$=—C(O)—NH-Phenyl

The title compound was prepared using the procedure described in Example 91 and substituting phenyl isocyanate for ethyl isocyanate. MS (FAB) m/e 965 (M+K)$^+$. $^{13}$C NMR (CDCl$_3$) δ213.4,213.2(C22), 196.2,192.6(9), 168.9,168.6(1), 165.8,164.7(8), 165.1 (thiolcarbamate carbonyl), 139.5,138.6(19), 137.8(para-phenyl C), 129.0(bridgehead phenyl C), 124.2,119.6(39,43,40,42-2 sets of symmetrical C's), 132.2,131.8(27), 129.9,129.5(28), 123.2,123.0(20), 98.5,97.0(10), 79.0(31), 77.7,77.5(26), 76.6,75.2(15), 73.6,73.6(13), 72.8,72.2(14), 70.0,69.1(24), 57.4,56.9(15OMe), 56.5,56.2,56.1,56.1,56.0(13OMe, 31OMe,2), 54.9,54.7(21), 52.6(2), 48.6,48.3(18), 45.9,45.9(32), 43.8,39.1(6), 43.5,43.3(23), 40.2,39.6(25), 35.4,33.0(16), 34.7(29), 34.5,33.5(11), 32.6,32.5(12),30.4, 28.1,28.0(34,33,30) 27.6,26.2(3), 26.2,26.0(17), 24.5,24.5, 24.4,24.2(5,35), 21.20.7(4), 20.3,19.4(17Me), 16.1,15.9(11Me), 15.7,15.6(19Me), 14.1,13.7(27Me), 11.6, 11.6(36), 9.7,9.4(25Me). IR (CHCl$_3$) 3450, 2940, 1740, 1700, 1680 (shoulder), 1650 cm$^{-1}$.

EXAMPLE 95

Formula II: R$^0$=ethyl; R$^5$=—OH; m=0;R$^7$=—C(O)—NH—CH$_2$—CO$_2$CH$_2$CH$_3$ The title compound was prepared using the procedure described in Example 91 and substituting ethyl isocyanatoacetate for ethyl isocyanate. MS (FAB) m/e 975 (M+K)$^+$. $^{13}$C NMR (CDCl$_3$) δ 213.5,213.4(C22), 196.2,192.4(9), 169.3(glycine ethyl ester carbonyl C), 168.9,168.6(1), 167.2(thiolcarbamate carbonyl C), 165.8,164.7(8), 139.6, 138.7(19), 132.3,131.8(27), 129.5,129.4(28), 123.3,123.020), 98.6,96.9(10), 78.9(31), 77.6,77.0(26), 76.6,75.2(15), 73.7,73.6(13), 72.9,72.1(14), 70.1,69.2(24), 61.6(ethyl ester methylene C), 57.4,56.9(15OMe), 56.6, 56.3,56.1,56.0(31OMe, 13OMe,2), 54.9,54.6(21), 52.6(2), 48.6,48.4(18), 45.7(32), 43.8,39.2(6), 43.3,42.9(23), 42.7(glycine methylene C), 40.1,39.5(25), 35.5,32.8(16), 35.4,35.3(30), 34.7(29), 34.5,33.5(11), 32.7,32.6(12), 31.5(33 or 34), 28.0(33 or 34), 27.7,26.2(3), 26.3,26.0(17), 24.6,24.5,24.1(5,35), 21.1,20.8(4), 20.5,19.4(17Me), 16.2, 16.0(11Me), 15.8,15.6(19Me), 14.1(ethyl ester methyl C), 14.2,14.0(27Me), 11.6(36), 9.7,9.3(25Me). IR (CHCl$_3$) 3439(br), 2936, 2874(sh), 2826(sh), 1745, 1652, 1678(sh), 1454 cm$^{-1}$.

EXAMPLE 96

Formula II: R$^0$=ethyl; R$^5$=—OH; m=0;R$^7$=—C(O)—N(CH$_3$)$_2$

To a room temperature solution of the compound resulting from Example 8A (500 rag, 0.619 mmol) in 5 mL of freshly distilled tetrahydrofuran was added 8 equivalents of diisopropylethylamine followed by 4 equivalents of dimethylcarbamyl chloride and then a catalytic amount of dimethylaminopyridine. The reaction mixture was stirred for 30 hours at room temperature and then concentrated under reduced pressure. The residue obtained was dried to a constant weight (900 mg) and purified by silica gel column chromatography eluting with 25% acetone in hexane to give 310 mg of the title compound. MS (FAB) m/e 917 (M+K)$^+$. $^{13}$C NMR (CDCl$_3$) δ213.3,213.2(C22), 196.1,192.5(9), 168.9, 168.6(1), 167.5,167.4(carbamoyl C), 165.7,164.7(8), 139.5, 138.6(19), 132.0,131.6(27), 130.1,129.7(28), 123.2,123.0(20), 98.5,96.9(10), 78.9(31), 77.7,77.4(26), 76.6,75.1(15), 73.6,73.5(13), 72.8,72.1(14), 70.0,69.1(24), 57.4,56.8(15OMe), 56.5,56.2,56.1,56.0(31OMe, 13OMe,2), 54.9,54.7(21), 52.6(2), 48.6,48.3(18), 45.3,45.3(32), 43.7, 39.1(6), 43.4,43.2(23), 40.2,39.5(25), 36.6(dimethyl C's of thiolcarbamate), 35.9,35.8(30), 35.4,32.9(16), 34.7(29), 34.5,33.5(11), 32.6,32.5(12), 30.3(34), 28.0,27.9(33), 27.6, 26.1(3), 26.2,25.9(17), 24.5,24.4,24.1(5,35), 21.0,20.7(4), 20.3,19.4(17Me), 16.1,15.9(11Me), 15.6,15.7(19Me), 14.1, 13.8(27Me), 11.6(36), 9.7,9.4(25Me). IR (CHCl$_3$) 3445(br), 2935(s), 2878(sh),1744,1716(sh), 1652(s),1455 cm$^{-1}$.

EXAMPLE 97

Formula II: R$^0$=ethyl; R$^5$=—OH; m=0;R$^7$=—C(O)—N(CH$_2$CH$_2$)$_2$

The title compound was prepared using the procedure described in Example 96 and substituting diethylcarbamyl chloride for dimethylcarbamyl chloride. MS (FAB) m/e 945 (M+K)$^+$. $^{13}$C NMR (CDCl$_3$) δ213.4,213.3(C22),196.1, 192.5(9), 168.9,168.6(1), 166.4,166.3(carbamoyl carbonyl C), 165.8,164.7(8), 139.6,138.6(19), 132.0,131.5(27), 130.2,129.9(28), 123.3,123.1(20), 98.6,97.0(10), 79.0(31), 77.7,77.4(26), 76.6,75.2(15), 73.6,73.6(13), 72.8,72.2(14), 70.1,69.2(24), 57.4,56.9(15OMe), 56.6,56.2,56.1,56.0(31OMe, 13OMe,2), 54.9,54.7(21), 52.6(2), 48.6,48.3(18), 45.0,44.9(32), 43.8,39.1(6), 43.5, 43.2(23), 42.0(carbamoyl methylenes), 40.2,39.6(25), 35.9, 35.8(30), 35.5,33.0(16), 34.7(29), 34.5,33.5(11), 32.7,32.5(12), 30.3(34), 28.1,28.0(33), 27.6,26.2(3), 26.3, 26.0(17), 24.6,24.5,24.4,24.2(5,35), 21.0,20.8(4), 20.4,19.4(17Me), 16.1,15.9(11Me), 15.7,15.6(19Me), 14.1, 13.8(27Me), 11.6(36), 9.7,9.4(25Me). IR (CHCl$_3$) 3452(br), 2935,2969(sh),2876(sh),2825(sh),1744,1707,1649(s),1455 cm$^{-1}$.

EXAMPLE 98

Formula II: R$^0$=ethyl; R$^5$=—OH; m=0;R$^7$=—C(O)-(4-Morpholinyl)

The title compound was prepared using the procedure described in Example 96 and substituting 4-morpholinecarbonyl chloride for dimethylcarbamyl chloride. MS (FAB) m/e 959 (M+K)$^+$. $^{13}$C NMR (CDCl$_3$) δ213.3,213.2(C22), 196.1,192.6(9), 168.9,168.6(1), 167.0,167.0(thiolcarbamoyl carbonyl C), 165.7,164.7(8), 139.6,138.6(19), 132.1,131.7(27), 130.1,129.8(28), 123.3,123.1(20), 98.6,97.0(10), 78.9(31), 77.9,77.6(26), 76.6,75.2(15), 73.6, 73.6(13), 72.8,72.2(14), 70.0,69.1(24), 66.4(morpholino methylene C's alpha to O), 57.4,56.9(15OMe), 56.5,56.2, 56.2,56.0(31OMe, 13OMe,2), 54.9,54.7(21), 52.6(2), 48.6, 48.3(18), 45.3,45.4(32), 43.8,39.1(6), 43.5,43.4(23), 40.3, 39.6(25), 35.8(morpholino methylene C's alpha to N), 35.7(30), 35.5,33.0(16), 34.7(29), 34.5,33.6(11), 32.6,32.5(12), 30.3(34), 28.0,28.0 (33), 27.6,26.2(3), 26.2, 26.0(17), 24.6,24.4,24.2(5,35), 21.0,20.7(4), 20.3,19.4(17M), 15.9,16.1(11Me), 15.7,15.6(19Me), 14.0, 13.7(27Me), 11.6(36), 9.7,9.4(25Me). IR (CHCl$_3$) 3488 2934,2861,1744, 17 11,1650, 1451 cm$^{-1}$.

EXAMPLE 99

Formula II: R$^0$=ethyl; R$^5$=—OH; m=0; R$^7$=—C(O)—NHCH$_2$CO$_2$CH$_2$(4-Methoxyphenyl)

EXAMPLE 99A

4-Nitrophenylcarbamoylglycine 4-methoxybenzyl ester

The HCl salt of glycine 4-methoxybenzyl ester (1 g, 4.3 mmol) to was cooled to 0° C. and 7 mL of pyridine was added. After 10 minutes at 0° C., 4-nitrophenylchloroformate (980 mg, ~1.15 equivalents) was added over 5 minutes. The reaction mixture was stirred at 0° C. for 5 minutes and then allowed to warm to room temperature. After 1.5 hours at room temperature, the reaction mixture was diluted with ether and washed with cold 0.5N HCl and brine. The organic layer was dried over MgSO$_4$ and concentrated under reduced pressure to give 1.5 g of crude product.

EXAMPLE 99B

Formula II: R$^0$=ethyl; R$^5$=—OH; m=0; R$^7$=—C(O)—NHCH$_2$CO$_2$CH$_2$(4-Methoxyphenyl)

To a room temperature solution of the compound resulting from Example 8A (1.2 g, 1.49 mmol) in 12 mL of pyridine was added the compound resulting from Example 99A (2.5 equivalents, 1.34 g). The reaction mixture was heated to 70° C. After 6 hours the reaction was diluted with ether, and the solids were filtered. The organic flitrate was washed with 1N HCl followed by brine. The organic layer was dried over MgSO$_4$ and concentrated to give 2.2 g of crude product. Purification on silica gel column chromatography eluting with 30% acetone in hexane afforded 860 mg of the title compound. MS (FAB) m/e 1067 (M+K)$^+$. $^{13}$C NMR (CDCl$_3$) δ213.6,213.5(C22), 196.2,192.4(9), 169.3(glycine ester carbonyl C), 168.6(1), 167.3(thiolcarbamate carbonyl C), 165.9,164.7(8), 159.9(para aryl C), 139.7,138.7(19), 132.4,131.8(27), 130.3(meta aryl C's), 129.5(28), 127.1(Aryl C connecting benzylic methylene), 123.3,123.0(20), 114.1(ortho aryl C's), 98.7,97.0(10), 79.0(31), 77.6,77.0(26), 76.6,75.2(15), 73.7,73.7(13), 72.9, 72.2(14), 70.2,69.3(24), 67.2(benzylic methylene C's), 57.5, 56.9(15OMe), 56.2,56.3,56.2,56.1(5,35), 55.3(Aryl methoxy group), 55.0,54.7(21), 52.7(2), 48.6,48.5(18), 45.7(32), 43.8,39.2(6), 43.3,42.8(23), 42.8(glycine methylene C), 40.2,39.5(25), 35.6,32.9(16), 35.5,35.3(30), 34.7(29), 34.6, 33.5(11), 32.8,32.6(12), 30.5(33 or 34), 28.1(33 or 34), 27.7,26.2(3), 26.4,26.0(17), 24.6,24.5,24.2(5,35), 21.1,20.8(4), 20.5,19.5(17Me), 16.2,16.0(11Me), 15.9,15.7(19Me), 14.3,14.1(27Me), 11.7(36), 9.7,9.3(25Me). IR (CHCl$_3$) 3440(br), 2930, 2820(sh), 1740, 1650(s), 1680(sh), 1610(sh), 1515, 1450 cm$^{-1}$.

EXAMPLE 100

Formula II: R$^0$=ethyl; R$^5$=—OH; m=0; R$^7$=—C(O)—NHCH$_2$CO$_2$CH$_2$CH$_2$Si(CH$_3$)$_3$

EXAMPLE 100A

4-Nitrophenylcarbamoylglycine trimethylsilylethyl ester

The title compound was prepared using the procedure described for Example 99A and substituting the HCl salt of glycine trimethylsilylethyl ester for the HCl salt of glycine 4-methoxybenzyl ester.

EXAMPLE 100B

Formula II: R$^0$=ethyl; R$^5$=—OH; m =0; R$^7$=—C(O)—NHCH$_2$CO$_2$CH$_2$CH$_2$Si(CH$_3$)$_3$ To δ0° C. solution of the compound resulting from Example 8A (500 mg, 0.619 mmol) and diisopropylethylamine (3 equivalents, 325 μL) in 6 mL of methylene chloride was added a solution of the compound resulting from Example 100A (2.5 equivalents, 526 mg) in 3 mL of methylene chloride in one portion at 0° C. After stirring at 0° C. for 5 minutes, the reaction mixture was stirred at room temperature for 7 hours. The solvent was removed in vacuo, and the residue was dried to constant weight (1.13 g). Purification by silica gel column chromatography eluting with 25% acetone in hexane afforded 420 mg of the title compound. MS (FAB) m/e 1047 (M+K)$^+$. $^{13}$C NMR (CDCl$_3$) δ213.6,213.5(22), 196.2,192.4(9), 169.4(glycine ester carbonyl C), 169.0,168.6(1), 167.3(thiol carbamate carbonyl C), 165.8,164.7(8), 139.6,138.7(19), 132.3,131.8(27), 129.5,129.4(28), 123.3,123.0(20), 98.6,96.9(10), 79.0(31), 77.6,76.9(26), 76.6,75.2(15), 73.7, 73.6(13), 72.9,72.2(14), 70.1,69.2(24), 64.0,(TMS ethyl methylene C alpha to O), 57.4,56.9(15OMe), 56.6,56.3,56.1, 56.1 (2,31OMe, 13OMe), 54.9,54.7 (21), 52.7(2), 48.6, 48.4(18), 45.7(32), 43.8,39.2(6), 43.3,42.9(23), 42.9(glycine carbonyl C), 40.1,39.5(25), 35.6,32.8(16), 35.4,35.3(30), 34.7(29), 34.6,33.5(11), 32.7,32.6(12), 30.4(33 or 34), 28.0(33 or 34), 27.7,26.2(3), 26.4,26.0(17), 24.6,24.5,24.2(5,35), 21.1,20.8(4), 20.5,19.4(17Me), 17.3(TMS ethyl methylene C alpha to Silane), 16.2,16.0(11Me), 15.7,15.8(19Me), 14.2,14.1(27Me), 11.7(36), 9.7,9.3(25Me). IR (CHCl$_3$) 3440(br), 2930(s), 2820(sh), 1740(s), 1650(s), 1680(sh), 1450 cm$^{-1}$.

EXAMPLE 101

Formula II: R$^0$=ethyl: R$^5$=—OH; m =0; R$^7$=—C(O)—NHCH$_2$C(O)-(4-Morpholinyl)

4-Nitrophenylcarbamoylglycine morpholine amide was prepared using the procedure described for Example 100A and substituting the HCl salt of glycine morpholine amide for the HCl salt of glycine 4-methoxybenzyl ester.

The title compound was prepared using the procedure described in Example 100B and substituting the compound obtained above for the compound resulting from Example 100A. MS (FAB) m/e 1016(M+K)$^+$. $^{13}$C NMR (CDCl$_3$) δ213.6(C22), 196.3,192.3(9), 169.0,168.6(1), 167.0(thiolcarbamate carbonyl), 166.1,164.8(8), 139.7,138.7(19), 132.3,131.8(27), 129.2(28), 123.3,123.0(20), 98.6,96.9(10), 79.0(31), 77.4(26), 76.6,75.2(15), 73.7,73.7(13), 72.9,72.1(14), 70.2,69.3(24), 66.7,66.3(morpholino methylene C's alpha to O), 57.4,56.9(15OMe), 56.7,56.3,56.2(31OMe, 13OMe,2), 55.0,54.6(21), 52.7(2), 48.6,48.4(18), 45.5(32), 44.8(glycine methylene C), 43.8, 39.243.2,42.7(23), 42.3,42.4(morpholine methylene C's alpha to N), 40.0,39.4(25), 32.8(16), 35.5,35.4(30), 34.7(29), 34.6,33.5(11), 32.8,32.6(12), 30.5(33 or 34), 28.0(34 or 33), 27.7,26.2(3), 26.4,26.0(17), 24.5,24.2(5,35), 21.2,20.8(4), 20.5, 19.4(17Me), 16.2,16.0(11Me), 15.9,15.7(19Me), 14.3,14.2(27Me), 11.7(36), 9.7,9.3(25Me). IR (CHCl$_3$) 3440(br), 2940,2880(sh), 2830(sh), 1740,1710,1650(s), 1460 cm$^{-1}$.

EXAMPLE 102

Formula II: R$^0$=ethyl; R$^5$=—OH; m=0; R$^7$=—C(O)—NHCH$_2$C(O)-(1-Piperidinyl)

4-Nitrophenylcarbamoylglycine pipeddine amide was prepared using the procedure described for Example 100A and substituting the HCl salt of glycine piperidine amide for the HCl salt of glycine 4-methoxybenzyl ester.

The title compound was prepared using the procedure described in Example 100B and substituting the compound obtained above for the compound resulting from Example 100A. MS (FAB) m/e 1014 (M+K)$^+$. $^{13}$C NMR (CDCl$_3$) δ78.9(C31),45.3(C32), side chain C's:SCO(166.7), NHCH2(45.4), CO(165.3), Piperidine CH2's(43.1-two C's, 26.1-two C's, 25.3).

EXAMPLE 103

Formula II: R$^0$=ethyl; R$^5$=—OH; m=0; R$^7$=—C(O)—NHCH$_2$C(O)-(1-Pyrrolidinyl)

4-Nitrophenylcarbamoylglycine pyrrolidine amide was prepared using the procedure described for Example 100A and substituting the HCl salt of glycine pyrrolidine amide for the-HCl salt of glycine 4-methoxybenzyl ester.

The title compound was prepared using the procedure described in Example 100B and substituting the compound obtained above for the compound resulting from Example 100A. MS (FAB) m/e 1000 (M+K)$^+$. $^{13}$C NMR (CDCl$_3$) δ213.5(C22), 196.3,192.3(9), 168.9,168.6(1), 166.8(thiolcarbamate carbonyl C), 165.8,164.7(8), 165.7(glycine amide carbonyl C), 139.6,138.7(19), 132.2,131.6(27), 129.2(28), 123.2,122.9(20), 98.5,96.8(10), 78.9(31), 77.3,76.6(26), 76.6,75.1(15), 73.6(13), 72.9,72.0(14), 70.1,69.3(24), 57.3, 56.8(15OMe), 56.6,56.3,56.1(31OMe, 13OMe,2), 54.9,54.6(21), 52.6(2), 48.5,48.3(18), 45.9(32), 45.3(glycine alpha C), 43.7,39.1(6), 43.3(pyrrolidine C's alpha to N), 43.1,42.6(23), 39.9,39.3(25), 35.5,32.7(16), 34.6(29), 34.5, 33.4(11), 32.7,32.5(12), 30.5(33 or 34), 27.9(33 or 34), 27.7,26.2(3), 26.3,25.9(17), 25.8(pyrrolidine C's beta to N), 24.5,24.1,24.0(5,35), 21.1,20.7(4), 20.5,19.4(17Me), 16.1, 15.9(11Me), 15.8,15.6(19Me), 14.2,14.1(27Me), 11.6(36), 9.9,9.2(25Me). IR (CHCl$_3$) 3438(br), 2935, 2876(sh), 2826(sh), 1743, 1706, 1650 (s), 1452 cm$^{-1}$.

EXAMPLE 104

Formula II: R$^0$=ethyl; R$_5$=—OH; m=0; R$^7$=—C(O)—NHCH$_2$C(O)—CH$_2$CH(OCH$_2$CH$_3$)$_2$ 4-Nitrophenylcarbamoyl glycinediethylacetal was prepared using the procedure described in Example 100A and substituting aminoacetaldehyde diethyl acetal for the HCl salt of glycine 4-methoxybenzyl ester.

The title compound was prepared using the procedure described in Example 100B and substituting the compound obtained above for the compound resulting from Example 100A and utilizing NP-HPLC on a Rainin Microsorb column eluting with 25% acetone in hexane. MS (FAB) m/e 1005 (M+K)$^+$. $^{13}$C NMR (CDCl$_3$) δ213.5,213.4 (C22), 196.2, 192.5 (9), 168.9, 168.6 (1), 166.9 (carbamoyl carbonyl C), 165.8, 164.7 (8), 139.6, 138.7 (19), 132.2, 131.7 (27), 129.6, 129.5 (28), 123.3, 123.0 (20), 100.5 (acetal roethine C), 98.6, 97.0 (10), 79.0 (31), 77.6, 77.1 (26), 76.6, 75.2 (15), 73.7, 73.6 (13), 72.9, 72.2 (14), 69.2 (24), 62.9, 62.8 (ethyl acetal methylene C's), 57.4, 56.9 (15OMe), 56.6, 56.3, 56.1, 56.0 (31OMe, 13OMe, 2), 54.9, 54.7 (21), 52.6 (2), 48.6, 48.4 (18) 45.5 (32), 43.8, 39.2 (6), 43.6 (glycine alpha C), 43.4, 43.0 (23), 40.1, 39.5 (25), 35.4 (30), 35.5, 32.9(16), 34.7, (29), 34.5, 33.5 (11), 32.7, 32.6 (12), 30.5 (33 or 34), 28.0 (33 or 34), 27.6,2 6.2 (3), 26.3, 26.0 (17), 24.6, 24.5, 24.1 (5,35), 21.1, 20.8 (4), 20.4, 19.4 (17Me), 16.2, 16.0 (11Me), 15.8, 15.6 (19Me), 15.3, 15.2 (ethyl acetal methyl C's), 14.2, 14.0 (27Me), 11.6 (36), 9.7, 9.3 (25Me). IR (CHCl$_3$) 3429(br),2935(s),1740,1710(sh),1651(s),1455 cm$^{-1}$.

EXAMPLE 105

Formula II: R$^0$=ethyl; R$^5$=—OH; m=0; R$^7$=—C(O)—NHCH$_2$C(O)—CH$_2$CHO

To a room temperature solution of compound from Example 104 (650 mg, 0.672 mmol) and 10 mL of acetone was added 0.3 equivalents of p-toluenesulfonic acid monohydrate. The reaction was stirred for 6 hours. The reaction mixture was then filtered through a silica gel plug eluting with 40% acetone in hexane. The eluant was concentrated to give 629 mg of crude product. Purification by silica gel column chromatography eluting with 32% acetone in hexane gave 213 mg of the title compound. MS (FAB) m/e 931 (M+K)$^+$. $^{13}$C NMR (CDCl$_3$) δ213.4,213.3(C22), 196.2,192.6(9), 195.7(aldehyde C), 168.9,168.6(1), 167.5(thiolcarbamate carbonyl C), 165.8,164.7(8), 139.5, 138.6(19), 132.2,131.8(27), 129.6,129.4(28), 123.2,123.0(20), 98.5,96.9(10), 78.9(31), 77.6,77.2(26), 76.6,75.1(15), 73.6,73.5(13), 72.8,72.1(14), 70.0,69.1(24), 57.4,56.9(15OMe), 56.5,56.2,56.1,56.0(31OMe,13OMe,2), 54.9,54.7 (21), 52.6(2), 51.4(glycinal alpha C), 48.6,48.3(18), 45.7,45.7(32), 43.8,39.1(6), 43.4,43.1(23), 40.1,39.5(25), 35.4,32.9(16), 35.2(30), 34.6(29), 34.5,33.5(11), 32.6,32.5(12), 30.3(33 or 34), 28.0(33 or 34), 27.6,26.1(3), 26.2,25.9(17), 24.5,24.5,24.4,24.1(5,35), 21.0, 20.7(4), 20.4,19.4(17Me), 16.1,15.9(11Me), 15.7,15.6(19Me), 14.1,13.8(27Me), 11.6(36), 9.7,9.3(25Me). IR (CHCl$_3$) 3429 (br), 2935 (s), 1740, 1710 (sh), 165.1 (s), 1455 cm$^{-1}$.

EXAMPLE 106

Formula II: R$^0$=ethyl; R$^5$=—OH; m=0; R$^7$=—CO$_2$—CH$_2$CH$_3$

To a room temperature solution of the compound resulting from Example 8A (500 mag, 0,619 mmols) and diisopropylethylamine (5 equivalents, 540 μL) in 5 mL of methylene chloride was added ethyl chloroformate (1.2 equivalents, 71 μL) followed by 4-dimethylaminopyridine (1 equivalent, 75 mag). After 16 hours, the reaction-was concentrated under reduced pressure, and the residue was dried to give 750 mg of crude product. Purification by silica gel column chromatography eluting with 25% acetone in hexane provided 500 mg of the title compound. MS (FAB) m/e 918 (M+K)$^+$. $^{13}$C NMR (CDCl$_3$) δ213.3(C22), 196.1,192.5(9), 170.5, 170.4(thiolcarbonate carbonyl C), 168.9,168.6(1), 1655.7, 164.6(8), 139.5,138.6(19), 132.3,131.7(27), 129.2(28), 123.2,122.9(20), 98.5,96.8(10), 78.7(31), 77.4,76.8(26), 76.5,75.1(15), 73.6,73.5(13), 72.8,72.1 (14), 70.069.1(24), 63.3,63.3(methylene of ethyl grp of carbonate), 57.3,56.8(15OMe), 56.5,56.2,56.1,55.9(31OMe, 13OMe,2), 54.8,54.6(21), 52.6(2), 48.5,48.3(18), 46.2,46.1(methyl C of ethyl carbamate), 43.7,39.1(6), 43.2,42.8(23), 39.9,39.4(25), 35.4,32.7(16), 35.2(30), 34.5(29), 34.4,33.5(11), 32.6,32.4(12), 29.8(34), 27.7(33), 27.6,26.1(3), 26.2,25.9(17), 24.5,24.4,24.1,24.0(5,35), 21.0,20.7(4), 20.4, 19.4(17Me), 16.1,15.9(11Me), 15.7,15.6(19Me), 14.1,14.0(27Me), 11.6(36), 9.6,9.2(25Me). IR (CHCl$_3$) 3480, 2920, 2880 (shoulder), 2820, 1740, 1700, 1650, 1450 cm$^{-1}$.

EXAMPLE 107

Formula II: R$^0$=ethyl; R$^5$=—OH; m=0; R$_7$=—CO$_2$—CH$_2$CH(CH$_3$)$_2$

The title compound was prepared using the procedure described for Example 106 and substituting isobutyl chloroformate for ethyl chloroformate. MS (FAB) m/e 946 (M+K)$^+$. $^{13}$C NMR (CDCl$_3$) δ213.5,213.5(C22), 196.2,192.4(9), 170.7,170.6(carbonate carbonyl C), 169.0, 168.6(1),165.8,164.7(8), 139.6,138.7(19), 132.4,131.8(27), 129.3,129.2(28), 123.3,123.0(20), 98.6,96.9(10), 78.8(31), 77.5,76.8(26), 76.6,75.2(15), 73.7,73.6(13), 73.4, 73.3(isobutyl methylene), 72.9,72.1(14), 70.1,69.2(24), 57.4,56.9(15OMe), 56.6,56.3,56.2,56.2,56.0(31OMe, 13OMe,2), 54.9,54.6(21), 52.7(2), 48.5,48.4(18), 46.2,46.2(32), 43.8,39.2(6), 43.2,42.8(23), 40.0,39.5(25), 35.5,32.7(16), 32.8,32.5(12), 29.9(34), 27.8(33), 27.8(isobutyl methine C), 27.6,26.2(3), 26.4,26.0(17), 24.6, 24.6,24.5,24.1(5,35), 21.1,20.8(4), 20.5,19.4(17Me), 18.9(isobutyl methyl C's), 16.2,16.0(11Me), 15.8,15.6(19Me), 14.3,14.1(27Me), 11.6(36), 9.7,9.2(25Me). IR (CHCl$_3$) 3450, 2920, 2960 (shoulder=sh), 2880 (sh), 2820, 1740, 1700, 1650, 1450 cm$^{-1}$.

EXAMPLE 108

Formula II: R$^0$=ethyl; R$^5$=—OH; m=0; R$^7$=—CO$_2$—CH$_2$-(Phenyl)

The title compound was prepared using the procedure described for Example 106 and substituting benzyl chloroformate for ethyl chloroformate. MS (FAB) m/e 980 (M+K)$^+$. $^{13}$C NMR (CDCl$_3$) δ213.4(C22), 196.2,192.4(9), 170.6(carbonate carbonyl C), 168.9,168.6(1), 165.8,164.6(8), 139.6,138.7(19), 135.1(bridgehead phenyl C), 132.4,131.8(27), 129.1(28), 128.5,128.4,128.2(phenyl C's), 123.2,122.9(20), 98.6,96.9(10), 78.7(31), 77.4,76.7(26), 76.6,75.1(15), 73.6,73.5(13), 72.8,72.1(14), 70.0,69.2(24), 68.8,68.8(benzylic methylene C), 57.4,56.8(15OMe), 56.6,56.2,56.2,56.0(31OMe,13OMe,2), 54.9,54.6(21), 52.6(2), 48.5,48.4(18), 46.4(32), 43.8,39.1(6), 43.2,42.7(23), 39.9,39.4(25), 35.5,32.5(16), 35.2,35.0(30), 34.5(11 and/or 29), 33.5(11), 32.7(12), 29.8(34), 27.8(33), 27.6,26.2(3), 26.3,25.9(17), 24.5,24.5, 24.1(5,35), 21.1,20.7(4), 20.4,19.4(17Me), 16.1,15.9(11Me), 15.8,15.6(19Me), 14.2,14.1(27Me), 11.6(36), 9.7,9.2(25Me). IR (CHCl$_3$) 3440, 2920, 2880 (shoulder=sh), 2840(sh), 1740, 1700, 1650, 1450 cm$^{-1}$.

EXAMPLE 109

Formula II: R$^0$=ethyl; R$^5$=—OH; m=0; R$^7$=—CO$_2$—CH$_2$CH$_2$CH$_3$

The title compound was prepared using the procedure described for Example 106 and substituting propyl chloroformate for ethyl chloroformate. MS (FAB) m/e 932 (M+K)$^+$. $^{13}$C NMR (CDCl$_3$) δ213.5,213.5(C22), 196.2,192.4(9), 170.6(thiolcarbonate carbonyl C), 169.0, 168.6(1), 165.8,164.7(8); 139.6,138.7(19), 132.4,131.8(27), 129.3,129.2(28), 123.3,123.0(20), 98.6,96.9(10), 78.8(31), 77.5,76.8(26), 76.6,75.2(15), 73.7,73.6(13), 72.9,72.1(14), 70.1,69.2(24), 69.0(n-propyl methylene C alpha to O), 57.4, 56.9(15OMe), 56.6,56.3,56.2,56.0(31OMe,13OMe,2), 54.9, 54.6(21), 52.7(2), 48.5,48.4(18), 43.8,39.2(6), 43.2,42.8(23), 40.0,39.4, 25), 35.5(16), 35.3,35.1(30), 34.6(29), 34.5,33.5(11), 32.7,32.6(12), 29.9(33 or 34), 27.8(33 or 34), 27.7,26.2(3), 26.4,26.0(17), 24.6,24.6,24.5, 24.1(5,35), 22.0(n-propyl methylene C beta to O), 21.1, 20.8(4), 20.5,19.4(17Me), 16.2,16.0(11Me), 15.8,15.6(19Me), 14.3,14.1(27Me), 11.6(36), 10.2(n-propyl methyl C), 9.7,9.2(25Me). IR (CHCl$_3$) 3480(br), 2930, 2960(sh),2880(sh),2820(sh), 1740,1700,1650,1460 cm$^{-1}$.

EXAMPLE 110

Formula II: R$^0$=ethyl; R$^5$=—OH; m=0; R$^7$=—CO$_2$—(CH$_2$)$_3$CH$_3$

The title compound was prepared using the procedure described for Example 106 and substituting butyl chloroformate for ethyl chloroformate. MS (FAB) m/e 946 (M+K)$^+$. $^{13}$C NMR (CDCl$_3$) δ213.6,213.6(C22), 196.2,192.4(9), 170.7(Thiolcarbonate carbonyl C), 169.0, 168.7(1), 165.8,164.7(8), 139.7,138.8(19), 132.4,13.1.8(27), 129.3,129.2(28), 123.3,123.0(20), 98.7, 97.0(10), 78.8(31), 77.5,76.8(26), 76.6,75.2(15), 73.7,73.6(13), 72.9,72.2(14), 70.1,69.2(24), 67.3(n-butyl methylene alpha to O), 57.5,56.9(15OMe), 56.7,56.3,56.2, 56.1(31OMe, 13OMe,2), 55.0,54.7(21), 52.7(2), 48.6,48.5(18), 46.2(32), 43.8,39.2(6), 43.3,42.7(23), 40.1, 39.5(25), 35.6(16), 35.3,35.2(30), 34.7(29), 34.6,33.6(11), 32.8,32.6(12), 30.7(33 or 34), 30.0(n-butyl methylene C beta to O), 27.8(33 or 34), 27.7,26.2(3), 26.4,26.0(17), 24.7,24.5,24.2(5,35), 21.2,20.8(4), 20.5,19.5(17Me), 19.0(n-butyl methylene C gamma to 0), 16.2,16.0(11Me), 15.9,15.6(19Me), 14.3,14.2(27Me), 13.6(n-butyl methyl C), 11.7(36), 9.7,9.3(25Me). IR (CHCl$_3$) 3475 (br), 2936, 2960 (sh), 2875 (sh), 2826 (sh), 1745, 1707, 1652, 1455 cm$^{-1}$.

EXAMPLE 111

Formula II: R$^0$=ethyl; R$^5$=—OH; m 32 0; R$^7$=—C(O)—CO$_2$CH$_3$

The title compound was prepared by the procedure described in Example and substituting methyl oxalyl chloride for acetyl chloride. The methyl oxalyl chloride was added at −78° C., and the reaction was run at −78° C. MS (FAB) m/e 932 (M+K)$^+$. $^{13}$C NMR (CDCl$_3$) δ213.5,213.4(C22), 196.1,192.4(9), 184.2,184.2(thioester carbonyl C), 168.9,168.6(1), 165.8,164.6(8), 159.5, 159.5(oxaloyl beta carbonyl C), 139.6,138.7(19), 132.7, 132.1(27), 129.0(28), 123.2,122.9(20), 98.6,96.9(10), 78.4(31), 77.5,76.8(26), 76.5,75.1(15), 73.6,73.6(13), 72.8, 72.1(14), 70.0,69.1(24), 57.4,56.9(15OMe), 56.6,56.3,56.3, 56.2,56.0(13OMe,31OMe,2), 54.9,54.6(21), 53.7(methyloxalyl methyl C), 52.6(2), 48.5,48.4(18), 44.7,44.6(32), 43.8,39.1(6), 43.2,42.8(23), 40.0,39.4(25), 35.5,32.5(16), 35.4,35.3(30), 34.5(29), 34.5,33.5(11), 32.7,32.7(12), 29.2(34), 28.0(33) 27.6,26.1(3), 26.3,25.9(17), 24.5,24.524.4,24.1(5,35),21.1,20.7(4),20.4,19.4(17Me), 16.1,15.9(11Me), 15.8,15.6(19Me), 14.2,14.1(27Me), 11.6(36), 9.6,9.2(25Me). IR (CHCl$_3$) 3480 (br), 2920 (s), 2880 (sh), 2830 (sh), 1740 (s), 1700, 1680, 1650 (s), 1450 cm$^{-1}$.

EXAMPLE 112

Formula II: R$^0$=ethyl; R$^5$=—OH; m=0; R$^7$=—C(O)-(2-Acetoxyphenyl)

The title compound was prepared by the procedure described in Example 84 and substituting acetylsalicyloyl chloride for acetyl chloride. MS (FAB) m/e 1008 (M+K)$^+$. $^{13}$C NMR (CDCl$_3$) δ213.4,213.3(C22), 196.1,192.5(9), 189.4,189.4(thioester carbonyl C), 169.2(aceto carbonyl C), 168.9,168.6(1), 165.8,164.7(8), 147.7,133.2,130.7,125.9, 123.8(phenyl C's), 139.5,138.6(19), 132.3,131.9(27), 129.5, 129.4(28), 123.2,123.0(20), 98.5,96.9(10), 78.6(31), 77.6, 77.1(26), 76.6,75.1(15), 73.6,73.6(13), 72.8,72.1(14), 70.0, 69.1(24), 57.4,56.9(15OMe), 56.5,56.2,56.1,56.0(13OMe, 31OMe,2), 54.9,54.6(21), 48.5,48.3(18), 44.1,44.1(32), 43.7,39.1(6), 43.3,43.0(23), 40.1,39.5(25), 35.9,32.8(16), 34.6(29), 34.5,33.5(11), 32.6,32.5(12), 29.6(34), 28.2(33), 27.6,26.1(3), 26.3,25.9(17), 24.5,24.4,24.1(5,35), 21.0,20.7(4), 20.9(Acetyl methyl C), 20.4,19.4(17Me), 16.1, 15.9(11Me), 15.7,15.6(19Me), 14.2,13.9(27Me), 11.6(36), 9.7,9.3(25Me). IR (CHCl$_3$) 3451(br), 2936(s), 2077 (sh), 2825(sh), 1772, 1744, 1707, 1652(s), 1448(s) cm$^1$.

EXAMPLE 113

Formula II: R$^0$=ethyl; R$^5$=—OH; m=0; R$^7$=—C(O)-(3-Pyridyl)

The title compound was prepared by the procedure described in Example and substituting nicotinoyl chloride for acetyl chloride with prolonged reaction time (16 hours) at room temperature. MS (FAB) m/e 951 (M+K)$^+$. $^{13}$C NMR (CDCl$_3$) δ213.4,213.3(C22), 196.2,192.6(9), 189.6,189.5(37), 168.9,168.6(1), 165.8,164.7(8), 153.6, 148.5,148.4,123.2(pyridine ring C's), 132.8(pyridine ring bridgehead C), 139.5,138.6(19), 132.5,132.0(27), 129.5,129.3(28), 123.3,123.0(20), 98.6,96.9(10), 78.6(31), 77.7,77.2(26), 76.6,75.2(15), 73.6,73.6(13), 72.8,72.2(14), 70.0,69.1(24), 57.4,56.9(15OMe), 56.5,56.3,56.2,56.0(31OMe, 13OMe,2), 54.9,54.7(21), 48.6,48.3(18), 44.4,44.4(32), 43.8,39.1(6), 43.4,43.1(23), 40.2,39.5(25), 35.7,32.9(16), 35.6,35.4(30), 34.6(29), 34.5, 33.6(11), 32.6,32.5(12), 29.7(34), 28.1(33), 27.6,26.2(3), 26.3,26.0(17), 24.5,24.5,24.4,24.1(5,35), 21.1,20.7(4), 20.4, 19.4(17Me), 16.1,15.9(11Me), 15.7,15.6(19Me), 14.1,13.9(27Me), 11.6(36), 9.7,9.3(25Me). IR (CHCl$_3$) 3392, 3244, 3057, 2973, 2934 (sh), 2831 (sh), 1653 (s), 1590, 1487 cm$^{-1}$.

EXAMPLE 114

Formula II: R$^0$=ethyl; R$^5$=—OH; m=0; R$^7$=—C(O)-(4-Pyridyl)

The title compound was prepared by the procedure described in Example 84 and substituting isonicotinoyl chloride hydrochloride for acetyl chloride. MS (FAB) m/e 951 (M+K)$^+$. $^{13}$C NMR (CDCl$_3$) δ212.9,212.8(C22), 195.7, 192.2(9), 189.9(thioester carbonyl C), 168.5,168.2(1), 165.3,164.3(8), 150.2(2 pyridine ring C's ortho to N), 143.0(pyridine ring bridgehead C), 139.1,138.2(19), 132.1, 131.7(27), 129.2,128.9(28), 122.9,122.6(20), 119.9(2 pyridine ring C's meta to N), 98.2,96.6(10), 78.2(31), 77.4, 77.0(26), 76.2,74.8(15), 73.2(13), 72.4,71.8(14), 69.5,68.6(24), 57.0,56.5(15OMe), 56.1,55.9,55.8,55.6(31OMe, 13OMe,2), 54.5,54.3(21), 52.2(2), 48.2,47.9(18), 44.3,44.2(32), 43.4,38.7(6), 43.1, 42.9(23), 39.8,39.2(25), 35.3,32.6(16), 35.1,35.0(30), 34.2(29), 34.1,33.2(11), 32.2,32.1 (12), 29.2(34), 27.7(33), 27.1(3), 25.8,25.6(17), 24.1,24.0,23.7(5,35), 20.6,20.3(4), 19.9,19.0(17Me), 15.7,15.5(11Me), 15.3,15.2(19Me), 13.7, 13.4(27Me), 11.2(36), 9.3,9.0(25Me). IR (CHCl$_3$) 3446 (br), 2936 (s), 2877 (sh), 2826 (sh), 1744, 1711, 1653 (s), 1556, 1454 cm$^{-1}$.

EXAMPLE 115

Formula II: R$^0$=ethyl; R$^5$=—OH; m=0; R$^7$=—C(O)—CH$_2$NH—C(O)CH$_3$

To the compound resulting from Example 8A (400 mg, 0.496 mmol) in 5 mL of methylene chloride was added N-acetylglycine (93 mg, 1.6 equivalents), diisopropylcarbodiimide (156 μL, 2 equivalents), diisopropylethylamine (86 μL, 1 equivalent), 4-dimethylaminopyridine (67 mg, 1.1 equivalents), and 1-hydroxybenzotriazole hydrate (67 mag, 1 equivalent). The reaction was stirred at room temperature for 16 hours, and the solvent was evaporated under reduced pressure. The residue obtained was dried to constant weight to give 1 g of crude product. After filtration of the crude material through a silica gel plug by elution with 50% acetone in hexane, the filtrate was concentrated under reduced pressure. Purification by NP-HPLC using a Rainin Microsorb column eluting with 40% acetone in hexane afforded 160 mg of pure title compound. MS (FAB) m/e 945 (M+K)$^+$. $^{13}$C NMR (CDCl$_3$) δ213.4,213.3(C22), 196.2,192.6(9), 195.9,195.8(37), 170.0(thioester carbonyl C), 169.0,168.6(1), 165.8,164.7(8), 139.5,138.7(19), 132.4, 131.9(27), 129.5,129.3(28), 123.2,123.0(20), 98.5,96.9(10), 78.6,78.5(31), 77.6,77.2(26), 76.6,75.2(15), 73.6,73.6(13), 72.8,72.2(14), 70.0,69.1(24), 57.4,56.9(15OMe), 56.5,56.2, 56.0(13OMe,31OMe,2)54.9,54.7 (21), 52.6(2), 49.4(glycine methylene C), 48.6,48.3(18), 44.0,43.9(32),43.8,39.1(6), 43.4,43.1(23), 40.1,39.5(25), 35.4 (30),35.3,32.9(16), 34.5(29), 34.5,33.5(11), 32.6,32.5(12), 29.6,28.0(34,33), 27.6,26.1(3), 26.3,26.0(17), 24.5,24.4,24.1(5,35), 22.9(acetyl methyl C), 21.0,20.7(4), 20.4,19.4(17Me), 16.1, 15.9(11Me), 15.7,15.6(19Me), 14.1,13.9(27Me), 11.6(36), 9.7,9.3(25Me).

EXAMPLE 116

Formula II: R$^0$=ethyl; R$^5$=—OH; m=0; R$^7$=—C(O)—(CH$_2$)$_2$NH—C(O)CH$_3$

The title compound was prepared by the procedure described in Example 115 and substituting N-acetyl-β-alanine for N-acetylglycine. MS (FAB) m/e 959 (M+K)$^+$. $^{13}$C NMR (CDCl$_3$) δ213.3,213.2(C22), 197.7,197.6((thioester carbonyl C), 196.2,192.6(C9), 170.1(N-acetyl carbonyl C), 168.9,168.6(1), 165.8,164.7(8), 139.5,138.6(19), 132.3,131.9(27), 129.4,129.2(28), 123.2,122.9(20), 98.5,96.9(10), 78.7(31), 77.6,77.1(26), 76.6,75.1(15), 73.5(13), 72.8,72.1(14), 69.9,69.0(24), 57.3,56.8(15OMe), 56.5, 56.2, 56.2, 55.9 (13OMe, 31OMe, 2), 54.8,54.6(21), 52.6(2), 48.5,48.2(18), 43.8(32), 43.7,39.1(6), 43.6(methylene C alpha to beta Ala carbonyl), 43.3,43.1(23),40.0,39.4(25), 35.2,32.8(16), 35.4(30), 35.4(methylene C beta to carbonyl in beta Ala), 34.4, 33.5(11), 34.6(29), 32.6,32.4(12), 29.7(34), 28.0(33), 27.5, 26.1(3), 26.2,25.9(17), 24.4,24.4,24.1(5,35), 23.0(41), 21.0, 20.7(4), 20.3,19.4(17Me), 16.1,15.9(11Me), 15.7,15.6(19Me), 14.1,13.8(27Me), 11.5(36), 9.6,9.2(25Me). IR (CHCl$_3$) 3400(br), 2920(s),2880(sh), 2840(sh), 1740,1680(sh),1650(s),1450 cm$^{-1}$.

EXAMPLES 117A and 117B

Formula II: R$^0$=ethyl; R$^5$=—OH; m=0; R$^7$=(D or L) —C(O)—CH(CH$_3$)NH—C(O)CH$_3$ The title compound was prepared by the procedure described in Example 115 and substituting N-acetyl-L-alanine for N-acetylglycine. Racemization of the N-acetylalanine during coupling gave rise to a mixture diastereomeric products. The diastereomers were separated by NP-HPLC using a Rainin Microsorb column.

Example 177A: MS (FAB) m/e 959 (M+K)$^+$. $^{13}$C NMR (CDCl$_3$) δ213.5,2 13.4(C22), 200.1,200.0(thioester carbonyl C), 196.2,192.5(9), 169.5(Acetyl carbonyl C), 169.0, 168.7(1), 165.8,164.7(8), 139.6,138.7(19), 132.4,132.0(27), 129.6,129.4(28), 123.3,123.0(20), 98.6,97.0(10), 78.7,78.6(31), 77.8,77.3(26), 76.6,75.2(15), 73.7,73.6(13), 72.9,72.2(14), 70.1,69.1(24), 57.4,56.9(15OMe), 56.6,56.3, 56.2,56.1 (13OMe,31OMe,2), 55.2(Ala alpha C), 55.0,54.7(21), 52.7(2), 48.6,48.4(18), 44.1,44.0(32), 43.8, 39.2(6), 43.5,43.1(23), 40.3,39.6(25), 35.6,35.5(30), 35.5, 33.0(16), 34.6(29), 34.6,33.6(11), 32.7,32.6(12), 29.6(34), 28.1,28.0(33), 27.6,26.2(3), 26.3,26.0(17), 24.6,24.5,24.2(5, 35), 23.2(Acetyl methyl C), 21.1,20.8(4), 20.4,19.5(17Me), 19.2,19.1(Ala methyl C), 16.2,16.0(11Me), 15.8,15.7(19Me), 14.1,13.9(27Me), 11.7(36), 9.8,9.4(25Me). IR (CHCl$_3$) 3433(br),2936(s),2875(sh), 2823(sh),1744,1688,1653(s),1532,1453 cm$^{-1}$.

Example 177B: MS (FAB) m/e 959 (M+K)$^+$. $^{13}$C NMR (CDCl$_3$) δ213.5,213.4(C22), 199.9,199.8(thioester carbonyl C), 196.2,192.5(9), 169.4(Acetyl carbonyl C), 169.0,168.7(1), 165.9,164.7(8), 139.6,138.7(19), 132.4,131.9(27), 129.4,129.3(28), 123.2,123.0(20), 98.6,97.0(10), 78.5(31), 77.6,77.0(26), 76.6,75.2(15), 73.7, 73.6(13), 72.9,72.2(14), 70.1,69.2(24), 57.4,56.9(15OMe), 56.6,56.3,56.1,56.0(13OMe,31OMe,2), 55.3,55.3(Ala alpha C), 54.9,54.7(21), 52.7(2), 48.6,48.4(18), 44.0,44.0(32), 43.8,39.2(6), 43.4,43.0(23), 40.1,39.5(25), 35.6,35.5(30), 35.5,32.9(16), 32.7,32.6(12), 29.6(34), 28.2,28.1(33), 27.6, 26.2(3), 26.3,26.0(17), 24.6,24.5,24.5,24.2(5,35), 23.1(acetyl methyl C), 21.1,20.7(4), 20.5,19.4(17Me), 19.5(Ala methyl C), 16.2,16.0(11Me), 15.8,15.7(19Me), 14.2,14.0(27Me), 11.7,11.6(36), 9.7,9.3(25Me). IR (CHCl$_3$) 3432(br),2936(s),2877(sh),2826(sh), 43,1688,1653(s), 1532,1453 cm$^{-1}$.

EXAMPLE 118

Formula II: $R^0$=ethyl; $R^5$=—OH; m=0; $R^7$=—C(O)-(2-Acetamidophenyl)

The title compound was prepared by the procedure described in Example 115 and substituting N-acetylanthranilic acid for N-acetylglycine and running the reaction for 72 hours. MS (FAB) m/e 1007 (M+K)$^+$. $^{13}$C NMR (CDCl$_3$) δ213.2,213.1(C22), 195.9,192.2(9), 194.7,194.7(thioester carbonyl C), 168.8(acetyl carbonyl C), 168.7,168.4(1), 165.5,164.4(8), 139.3,138.4(19), 138.3(aryl ring C attached to thioester linkage), 134.3,129.3,122.2,120.5(aryl C's), 132.2,131.7(27), 1290.3,29.1(28), 123.0,122.8(20), 122.5(aryl ring C attached to N-acetyl), 98.3,96.7(10), 78.4(31), 77.4,77.0(26), 76.3,74.9(15), 73.4,73.3(13), 72.6, 71.9(14), 69.7,68.8(24), 57.2,56.7(15OMe), 56.3,56.0,56.0, 55.8(13OMe,31OMe,2), 54.7,54.4(21), 52.4(2), 48.3,48.1 (18), 44.2(32), 43.5,38.9(6), 43.1,42.9(23), 39.9,39.3(25), 35.4,32.7(16), 35.3,35.2(30), 34.4(29), 34.3,33.3(11), 32.4, 32.3(12), 29.4(34), 27.9(33), 27.3,25.9(3), 26.0,25.7(17), 25.1 (acetyl methyl C), 24.3,24.2,23.9(5,35), 20.8,20.5(4), 20.2,19.2(17Me), 15.9,15.7(11Me), 15.5,15.4(19Me), 13.9, 13.7(27Me), 11.4(36), 9.5,9.1(25Me). IR (CHCl$_3$) 3450 (br), 2930 (s), 2880 (sh), 2820 (sh), 1740, 1705, 1650 (s), 1580, 1520, 1450 cm$^{-1}$.

EXAMPLE 119

Formula II: $R^0$=ethyl; $R^5$=—OH; m=0; $R^7$=—C(O)-(2-Cyanophenyl)

The title compound was prepared by the procedure described in Example 115 and substituting phthalamic acid for N-acetylglycine. MS (FAB) m/e 975 (M+K)$^+$. $^{13}$C NMR (CDCl$_3$) δ213.3,213.2(C22), 196.1,192.6(9), 189.1, 189.1(thioester carbonyl C), 168.9,168.6(1), 165.7,164.7(8), 139.7(aryl ring C bonded to thioester), 139.5,138.6(19), 134.8,132.5,132.4,129.0(aryl ring C's), 132.4,132.0(27), 129.8,129.4(28), 123.3,123.0(20), 117.3,117.3(nitrile C), 110.1,110.1(aryl ring C bonded to nitrile), 98.5,97.0(10), 78.5(31), 77.8,77.5(26), 76.6,75.2(15), 73.6,73.5(13), 72.8, 72.2(14), 69.9,69.0(24), 57.4,56.9(15OMe), 56.5,56.4,56.4, 56.2,56.0(13OMe,31OMe,2), 54.9,54.7(21), 52.6(2), 48.6, 48.3(18), 45.3,45.2(32), 43.8,39.1(6), 43.5,43.3(23), 40.3, 39.6(25), 35.7,33.0(16), 35.6,35.4(30), 34.5(29), 34.5,33.5(11), 32.6,32.5(12), 26.5(34), 28.3,28.2(33), 27.6, 26.2(3), 26.2,26.0(17), 24.5,24.4,24.4,24.1 (5,35), 21.0,20.7(4),20.3,19.4(17Me), 16.1,15.9(11Me), 15.7,15.6(19Me), 14.1,13.8(27Me), 11.6,11.6(36), 9.7,9.4(25Me). IR (CHCl$_3$) 3500 (br), 2940 (s), 2880 (sh), 2840 (sh), 2240 (wk), 1740, 1720, 1650 (vs), 1450 cm$^{-1}$.

EXAMPLE 120

Formula II: $R^0$=ethyl; $R^5$=—OH; m=0; $R^7$=—C(O)-(2-Pyridyl)

The title compound was prepared by the procedure described in Example 115 and substituting picolinic acid for N-acetylglycine. MS (FAB) m/e 951 (M+K)$^+$. $^{13}$C NMR (CDCl$_3$) δ213.6,213.4(C22), 196.2,192.3(9), 92.3, 192.2(thioester carbonyl Carbon), 169.0,168.6(1), 165.8, 164.7(8), 152.0,148.9,137.1,127.6,120.5(pyridine ring carbons), 139.6,138.7(19), 132.4,131.9(27), 129.2,129.1(28), 123.2,122.9(20), 98.5,96.8(10), 78.9(31), 77.4(26), 76.6, 75.1(15), 73.6,73.5(13), 72.9,72.0(14), 70.0,69.3(24), 57.3, 56.9(15OMe), 56.6,56.3,56.2,56.0(31OMe, 13OMe,2), 54.9,54.6(21), 52.6(2), 48.4,48.3(18), 43.7,39.1(6), 43.1(32), 42.7,42.6(23), 39.6,39.4(25), 35.6,35.4(30), 35.5, 32.7(16), 34.8(29), 34.5,33.4(11), 32.6,32.5(12), 29.8(34), 28.1(33), 27.6,26.1(3), 26.3,25.9(17), 24.6,24.4,24.1(5,35), 21.1,20.7(4), 20.5,19.3(17Me), 16.1,15.9(11Me), 15.8,15.6(19Me), 14.3,14.2(27Me), 11.6(36), 9.6,9.0(25Me). IR (CHCl$_3$) 3450(br),2940(s),2880(sh), 2830(sh), 1740,1710,1650(s),1455 cm$^{-1}$.

EXAMPLE 121

Formula II: $R^0$=ethyl; $R^5$=—OH; m=0; $R^7$=—C(O)—CH$_2$—NH—C(O)—NH$_2$

To the compound resulting from Example 8A (450 mg, 0.558 mmol) in 2.5 mL of dimethylformamide was sequentially added hydantoic acid (85 mg, 1.3 equivalents), 1-(3-dimethylaminopropyl)-3-ethylcarbodiimide hydrochloride (EDCI) (321 mg, 3 equivalents), N-methylmorpholine (123 μL, 2 equivalents), and 1-hydroxybenzotriazole hydrate (75 mg, 1 equivalent). The reaction was stirred at room temperature for 20 hours and then diluted with ethyl acetate and washed with 1N HCl followed by brine. After drying over MgSO$_4$, the organic phase was concentrated under reduced pressure and dried to give 419 mg of crude product. After filtration of the crude material through a silica gel plug by elution with 60% acetone in hexane, the filtrate was concentrated under reduced pressure to provide 250 mg of semi-pure material. Final purification by NP-HPLC using a Rainin Microsorb column and eluting with 58% acetone in hexane afforded 110 mg of pure title compound. MS (FAB) m/e 946 (M+K)$^+$. $^{13}$C NMR (CDCl$_3$) δ213.5,213.3(C22), 197.6,197.6(thioester carbonyl C), 196.3,192.9(9), 169.1, 168.8(1), 165.8,164.9(8), 158.3(carbamoyl C), 139.6,138.7(19), 132.3,132.0(27), 130.1,129.6(28), 123.3, 123.1(20), 98.6,97.1(10), 78.7(31), 78.0,77.9(26), 76.7,75.3(15), 73.7(13), 72.9,72.3(14), 70.069.1(24), 57.5, 57.0(15OMe), 56.6,56.3,56.1(13OMe,31OMe,2), 54.9,54.8(21), 52.8(2), 50.4(glycine methylene C), 48.8, 48.4(18), 43.9,39.3(6), 43.8(32), 43.7(23), 40.3,39.7(25), 35.5,33.1(16), 34.6(29), 34.6,33.7(11), 32.7,32.6(12), 29.7(34), 28.1,28.0(33), 27.6,26.3(3), 26.3,26.1(17), 24.5, 24.5,24.3(5,35),21.0,20.8(4),20.4,19.5(17Me), 16.2,16.0(11Me), 15.8(19Me), 14.2,13.7(27Me), 11.7(36), 9.8,9.6(25Me).

EXAMPLE 122

Formula II: $R^0$=ethyl; $R^5$=—OH; m=0; $R^7$=(L)—C(O)CH-(CH(OH)—$CH_3$)—NH—C(O)$CH_3$ The title compound was prepared by the procedure described in Example 121 and substituting N-acetyl-L-threonine for hydantoic acid. MS (FAB) m/e 989 (M+K)$^+$. $^{13}$C NMR (CDCl$_3$) δ213.4,213.3(C22), 198.2, 198.2(thioester carbonyl C), 196.2,192.5(9), 170.5(acetyl carbonyl C), 169.0,168.7(1), 165.8,164.8(8), 139.6,138.7(19), 132.4,132.0(27), 129.6,129.3(28), 123.2, 123.0(20), 98.6,97.0(10), 79.2,79.1(31), 77.7,77.4(26), 76.6, 75.2(15), 73.6,73.6(13), 72.9,72.2(14), 70.0,69.1(24), 68.4, 68.4(sidechain C of threonine), 64.1,64.1(alpha methine C of threonine), 57.4,57.0(15OMe), 56.6,56.4,56.2, 56.0(13OMe,31OMe,2), 54.9,54.7(21), 52.7(2), 48.6,48.4(18), 44.2,44.1(32), 43.8,39.2(6), 43.4,43.3(23), 40.2,39.6(25), 35.5,33.0(16), 35.1,34.9(30), 34.7(29), 34.5, 33.5(11), 32.6,32.5(12), 29.4(34), 28.4,28.3(33), 27.6,26.2(3), 26.3,26.0(17), 24.5,24.4,24.2(5,35), 23.0(acetyl methyl C), 21.0,20.7(4), 20.4,19.4(17Me), 19.4(methyl side chain C in threonine), 16.1,15.9(11Me), 15.8,15.7(19Me), 14.1,13.8(27Me), 11.6(36), 9.7,9.4(25Me). IR (CHCl$_3$) 3434 (br), 2935 (s), 2877 (sh), 2826 (sh), 1743, 1684(sh), 1652 (s), 1519, 1454 cm$^{-1}$.

EXAMPLE 123

Formula II: $R^0$=ethyl; $R^5$=—OH; m=0; $R^7$=(L)—C(O)—CH(OH)—$CH_3$

The title compound was prepared by the procedure described in Example 121 and substituting L-lactic acid for hydantoic acid. MS (FAB) m/e 918 (M+K)$^+$. $^{13}$C NMR (CDCl$_3$) δ213.4,213.3(C22), 203.4,203.4(thioester carbonyl), 196.0,192.3(9), 168.8,168.5(1), 165.7,164.6(8), 139.5, 138.6(19), 132.3,131.9(27), 129.3,129.2(28), 123.1,122.9(20), 98.5,96.9(10), 78.6(31), 77.5,77.0(26), 76.5,75.1(15), 74.0(13), 73.5(lactic acid alpha methine C), 72.7,72.0(14), 69.9,69.0(24), 57.3,56.8(15OMe), 56.5,56.1, 56.1,55.9(13OMe,31OMe,2), 54.8,54.6(21), 52.5(2), 48.5, 48.3(18), 43.7,39.1(6), 43.2,42.9(23), 43.2,43.1(32), 40.0, 39.4(25), 35.4(30), 35.3,32.8(16), 34.6(29), 34.4,33.4(11), 32.6,32.4(12), 29.6(34), 27.9(33), 27.5,26.1(3), 26.2,25.9(17), 24.4,24.3,24.0(5,35), 20.9,20.6(4), 20.9(lactic acid methyl C), 20.3,19.3(17Me), 16.0,15.8(11Me), 15.7, 15.5(19Me), 14.1,13.9(27Me), 11.5,11.5(36), 9.6,9.2(25Me). IR (CHCl$_3$) 3450 (br), 2936 (s), 2877 (sh), 2826 (sh), 1745, 1685, 1652 (s), 1454 cm$^{-1}$.

EXAMPLE 124

Formula II: $R^0$=ethyl; $R^5$=—OH; m=0; $R^7$=(D)-C(O)—CH(OH)—$CH_3$

The title compound was prepared by the procedure described in Example 121 and substituting D-lactic acid for hydantoic acid. MS (FAB) m/e 918 (M+K)$^+$. $^{13}$C NMR (CDCl$_3$) δ213.4,213.3(C22), 203.4,203.4(thioester carbonyl C), 196.2,192.5(9), 168.9,168.6(1), 165.8,164.7(8), 139.5, 138.7(19), 132.3,131.9(27), 129.5,129.3(28), 123.2,123.0(20), 98.6,96.9(10), 78.6(31), 77.6,77.2(26), 76.6,75.1(15), 74.0(13), 73.6,73.6(lactic acid roethine C), 72.8,72.1(14), 70.0,69.1(24), 57.4,56.9(15OMe), 56.5, 56.2, 56.2, 56.0(13OMe, 31OMe, 2), 54.9,54.7(21), 52.6(2), 48.6, 48.3(18), 43.7,39.1(6), 43.4,43.3(32), 43.3,43.1(23), 40.1, 39.5(25), 35.5(30), 35.4,32.9(16), 34.6(29), 34.5,33.5 (11), 32.6,32.5(12), 29.7(34), 28.0(33), 27.5,26.1(3), 26.3,26.0(17), 24.5, 24.4, 24.1(5,35), 21.1(lactic acid methyl C), 21.0,10.7(4), 20.4,19.4(17Me), 16.1, 15.9(11Me), 15.7, 15.6(19Me), 14.1,13.9(27Me), 11.6(36), 9.7,9.3(25Me). IR (CHCl$_3$) 3448(br),2936(s),2877(sh),2826(sh),1745,1685, 1652(s),1454 cm$^{-1}$.

EXAMPLE 125

Formula II: $R^0$=ethyl; $R^5$=—OH; m=0; $R^7$=(D)-C(O)—$CH_2$(OH)

The title compound was prepared by the procedure described in Example 121 and substituting glycolic acid for hydantoic acid. MS (FAB) m/e (M+K)$^+$. $^{13}$C NMR (CDCl$_3$) δ213.6,213.5(22), 200.0,200.0(thioester carbonyl C), 196.2, 192.5(9), 169.0,168.7(1), 165.8,164.7(8), 139.6,138.7(19), 132.5,132.0,(27), 129.4,129.3(28), 123.3,123.0(20),98.6,97.0(10), 78.7(31), 77.7,77.1(26), 76.6,75.2(15), 73.7,73.6(13), 72.9,72.2(14), 70.1,69.2(24), 68.5(glycolic acid methylene C), 57.5,56.9(15OMe), 56.6, 56.3,56.3,56.3,56.1(13OMe,31OMe,2), 55.0,54.7(21), 52.7(2), 48.6,48.4(18), 43.8,39.2(6), 43.4,43.3(32), 43.4, 43.0(23), 40.2,39.6(25), 35.5,35.5(30), 35.4,32.9(16), 34.7(29), 34.6,33.6(11), 32.7,32.6(12), 29.8(34), 28.0(33), 27.6,26.2(3), 26.3,26.0(17), 24.6,24.5,24.2(5,35), 21.1,20.8(4), 20.5,19.4(17Me), 16.2,16.0(11Me), 15.8,15.7(19Me), 14.2,14.0(27Me), 11.7,11.7(36), 9.7,9.4(25Me).

EXAMPLE 126

Alternate Preparation of Formula II: $R^0$=ethyl; $R^5$=—OH; m=0; $R^7$=—$CH_3$

To 50° C. solution of the compound resulting from Example 8A (2 g, 2.48 mmol) in 20 mL of acetonitrile was added finely powdered Cs$_2$CO$_3$ (1.5 g, 2 equivalents) over two minutes. After stirring for 5 minutes, the reaction mixture was cooled to −23° C. Methyl iodide (470 μL, 3 equivalents) was then added over 5 minutes. Upon complete addition, the reaction was stirred at −23° C. for 10 minutes and then warmed to 0° C. After stirring at 0° C. for 1 hour, the reaction mixture was diluted with ethyl acetate and decanted through fluted filter paper to remove solids. The filtrate was then concentrated under reduced pressure, and the residue was dried to give 2.1 g of crude product. After purification by silica gel column chromatography eluting with 20% acetone in hexane 1.3 g of the title compound was obtained.

EXAMPLE 127

Formula II: $R^0$=ethyl; $R^5$=—OH; m=1; $R^7$=—$CH_3$

To the compound resulting from Example 8A (1.09 g, 1.32 mmol) in 11 mL of methylene chloride was added finely powdered cesium carbonate (1.3 g, 3 equivalents). After stirring at room temperature for 10 minutes, the reaction was cooled to 0° C. and then 50% m-chloroperbenzoic acid (547 mg, 1.2 equivalents) was added portionwise over 20 minutes. After stirring at 0° C. for 1 hour, the cold reaction mixture was filtered through a bed of Celite. The flitrate was concentrated under reduced pressure, and the residue was dried to constant weight to give 1.2 g of a crude product mixture containing the isomeric title compounds and the sulfonyl compound. Initial purification was by silica gel column chromatography eluting with 50% acetone in hexane. Final purification was performed on a Rainin Microsorb NP-HPLC column eluting with 30% acetone in hexane to give 135 mg of the title compound. MS (FAB) m/e 876 (M+K)$^+$. $^{13}$C NMR (CDCl$_3$) $\delta$213.4,213.3(C22), 196.2,192.5(9), 169.0,168.6(1), 165.9,164.7(8), 139.5,138.7(19), 132.7,132.0(27), 129.2(28), 123.2,123.0(20), 98.5,96.9(10), 79.1(31), 77.6,76.8(26), 76.6,75.2(15), 73.6(13), 72.9,72.1(14), 70.0,69.1(24), 63.7, 63.6(32), 57.3,56.9(15OMe), 56.6,56.4,56.3,56.3, 56.0(13OMe,31OMe,2), 54.9,54.6(21), 52.6(2), 48.5,48.3(18), 43.7,39.2(6), 43.4,43.0(23), 40.6(sulfoxide methyl C), 40.1,39.7(25), 35.5,32.8(16), 34.6(29), 34.5, 33.5(11), 33.6,33.5(30), 32.7,32.5(12), 27.7(33 or 34), 27.7, 26.1(3), 26.3,26.0(17), 24.5,24.4,24.1(5,35), 23.3(33 or 34), 21.0,20.7(4), 20.4,19.4(17Me), 16.1,15.9(11Me), 15.7,15.8(19Me), 14.2,14.2(27Me), 11.6(36), 9.7,9.3(25Me). IR (CHCl$_3$) 3540(br), 2920(s), 2870(sh), 2820(sh), 1740, 1710, 1650(s), 1450 cm$^{-1}$.

EXAMPLE 128

Formula II: R$^0$=ethyl; R$^5$=—OH; m=1; R$^7$=—CH$_3$

The title compound (350 mg) was obtained as the other sulfoxide isomer from the preparation of Example 127. MS (FAB) m/e 876 (M+K)$^+$. $^{13}$C NMR (CDCl$_3$) $\delta$213.3(C22), 196.0,192.6(9), 169.9,168.6(1), 165.7,164.7(8), 139.5,138.6(19), 131.4,131.1(27), 129.1,128.9(28), 123.2, 123.1(20), 98.6,97.0(10), 78.2,77.3(26), 76.6,75.1(15), 73.6(13), 73.1,73.1(31), 72.8,72.2(14), 70.1,69.0(24), 66.6, 66.7(32), 57.4,56.9(15OMe), 56.8,56.7,56.6,56.2(13OMe, 31OMe,2), 54.9,54.7(21), 52.8(2), 48.7,48.5(18), 43.8,39.3(6), 43.5,43.4(23), 40.5,39.9(23), 36.4,36.4(sulfoxide methyl C), 35.4,32.8(16), 34.5,33.6(11), 32.7,32.5(12), 31.2,31.0(30), 30.1(29), 29.8,29.7(33 or 34), 27.3,26.1(3), 26.3,26.0(17), 24.6,24.5,24.4,24.2(5,35), 21.2, 20.8(4), 20.4,19.5(17Me), 17.6,17.4(33 or 34), 16.2,15.9(11Me), 15.6(19Me), 13.7(27Me), 11.6(36), 9.9, 9.5(25Me). IR (CHCl$_3$) 3440(br), 2920(s), 2880(sh), 2820(sh), 1740, 1710, 1650(s), 1450 cm$^{-1}$.

EXAMPLE 129

Formula II: R$^0$=ethyl; R$^5$=—OH; m=2; R$^7$=—CH$_3$

The title compound (175 mg) was obtained as a side product from the preparation of Example 127. MS (FAB) m/e 892 (M+K)$^+$. $^{13}$C NMR (CDCl$_3$) $\delta$213.5(C22), 196.0, 192.9(9), 169.0,168.7(1), 165.6,164.6(8), 139.6,138.7(19), 132.0,131.5(27), 129.1(28), 123.3,123.0(20), 98.7,97.1(10), 78.0,77.3(26), 76.5,75.2(15), 73.7(13), 72.8,72.3(14), 70.1, 69.0(24), 64.6,64.2(32??), 57.5,56.9(15OMe), 56.6,56.5, 56.4,56.3,56.0(13OMe,31OMe,2), 52.9(2), 48.7,48.5(18), 44.0,39.3(6), 43.5,43.1(23), 42.2,41.9(sulfone methyl C?), 40.4,39.9(25), 35.1,32.8(16), 34.5,33.8(11), 32.7,32.5(12), 31.0,30.9(30), 29.0,28.7(33 or 34), 27.5,26.2(3), 26.3,26.0(17), 24.6,24.5,24.4,24.1(5,35), 21.1,20.8(4), 20.4, 19.5(17Me), 16.2,15.9(11Me), 15.8,15.6(19Me), 13.8(27Me), 11.6(36), 9.9,9.5(25Me). IR (CHCl$_3$) 3500(br), 2930(s), 2880 (sh), 2830 (sh), 1740, 1715 (sh), 1650 (s), 1460 cm$^{-1}$.

EXAMPLE 130

Formula II: R$^0$=ethyl;R$^5$=—OH; m=0; R$^7$=—CH$_2$SCH$_3$

The title compound was prepared by the procedure described in Example 80 and substituting chloromethyl methyl sulfide for chloroacetone. MS (FAB) m/e 906 (M+K)$^+$. $^{13}$C NMR (CDCl$_3$) $\delta$213.8,213.7(C22), 195.5,192.6(9), 169.2,168.8(1), 166.0,164.9(8), 139.9,138.9(19), 132.2,131.7(27), 129.8(28), 123.5,123.2(20), 98.8,97.1(10), 81.0(31), 77.7,77.0(26), 76.8,75.4(15), 73.9(13), 73.1,72.3(14), 70.4,69.5(24), 57.6, 57.1(15OMe), 56.8, 56.5, 56.3, 56.2(31OMe, 13OMe,32, 2)55.2,54.8(21), 52.8(2), 48.7,48.6(18), 44.2(sulfide methyl C), 44.0,39.4(6), 43.4,43.0(23), 40.2,39.7(25), 38.1(methylene C bridging sulfur atoms), 35.8,32.8(16), 35.3(29), 34.8, 33.7(11), 34.2,34.1(12), 33.0(30) 29.8(34), 27.9,26.4(3), 27.6(33), 26.6,26.2(17), 24.8,24.7,24.3(5,35), 21.3,21.0(4), 20.7,19.6(17Me), 16.4,16.2(11Me), 16.0,15.8(19Me), 14.5, 14.3(27Me), 11.9(36), 9.9,9.5(25Me). IR (CHCl$_3$) 3448 (br), 2934 (s), 2877 (sh), 2824(sh), 1744, 1707, 1651(s), 1453 cm$^{-1}$.

EXAMPLE 131

Formula II: R$^0$=ethyl;R$^5$=—OH; m=0; R$^7$=—CH$_2$OCH$_3$

The title compound was prepared by the procedure described in Example 80 and substituting methoxymethyl chloride (MOM-Cl) for chloroacetone and running the reaction at room temperature for 3 hours. MS (FAB) m/e 890 (M+K)$^+$. $^{13}$C NMR (CDCl$_3$) $\delta$213.6,213.5(C22), 196.2,192.3(9), 169.0,168.6(1), 165.8,164.7(8), 139.6,138.7(19), 132.0,131.4(27), 129.7(28), 123.2,123.0(20), 98.6,96.9(10),80.5,80.5(31), 77.5,76.8(26),76.6,75.2(15), 75.2(thiomethylene Carbon), 73.7,73.6(13), 72.9,72.1(14), 70.1,69.3(24), 57.4,56.9(15OMe), 56.6,56.3,56.1,55.9,55.6(31OMe, 13OMe,32,2), 54.9,54.6(21), 52.6(2), 48.5,48.4(18), 44.3, 44.3(thiomethyl methyl ether methyl Carbon), 43.8,39.2(6), 40.0,39.4(25), 35.6,32.6(16), 35.0(29), 34.5,33.5(11) 33.8, 33.7(12), 32.8,32.7(30), 30.1(34), 27.6,26.2(3), 27.1(33), 26.3,25.9(17), 24.6,24.6,24.5,24.1(5,35), 21.1,20.7(4), 20.5, 19.4(17Me), 16.2,16.0(11Me), 15.8,15.6(19Me), 14.2,14.1(27Me), 11.6(36), 9.7,9.3(25Me). IR (CHCl$_3$) 3440(br),2930(s),2820(sh),1740,1650,1450 cm$^{-1}$.

EXAMPLE 132

Alternate Preparation of Formula II: R$^0$=ethyl;.R$^5$=—OH; m=0; R$^7$=-Phenyl

To δ0° C. solution of the compound resulting from Example 1, 32-trifluoromethanesulfonate ascomycin, (2 g, 2.17 mmol) in 12 mL of acetonitrile was added diisopropylamine (4 equivalents, 1.5 mL) dropwise over 5 minutes. Thiophenol (375 µL, 1.7 equivalents) was then added over 5 minutes, and the resultant solution was stirred at 0° C. for one hour. The solvent was then removed under reduced pressure and the residue dried to constant weight to give 2.6 g of crude product. Purification by silica gel column chromatography eluting with 20% acetone in hexane gave 1.39 g of pure title compound. MS (FAB) m/e 922 (M+K)$^+$. $^{13}$C NMR (CDCl$_3$) $\delta$213.6,213.6(C22), 196.2,192.3(9), 169.0, 168.7(1), 165.8,164.7(8), 139.7,138.7(19), 135.7(phenyl C bridged to S), 132.1,132.1,128.8,126.7,126.7(phenyl C's), 131.5(27), 129.6,129.6(28), 123.3,123.0(20), 98.6,96.9(10), 80.0(31), 77.5,76.8(26), 76.6,75.2(15), 73.7,73.6(13), 72.9, 72.1(14), 70.2,69.3(24), 57.4,56.9(15OMe), 56.7,56.3,56.1, 55.8(31OMe, 13OMe,2), 55.0,54.6(21), 49.3(32), 48.5,48.4(18), 43.8,39.2(6), 43.2,42.7(23), 40.0,39.5(25), 35.6,32.8(16), 34.9(29), 34.6,33.5(11), 33.9,33.7(30), 32.7, 32.6(12), 28.9(33 or 34), 27.7,26.2(3), 26.6(33 or 34), 26.4,26.0(17), 24.6,24.6,24.5,24.1(5,35), 21.1,20.8(4), 20.5, 19.4(17Me), 16.2,16.0(11Me), 15.8,15.6(19Me), 14.3,14.1(27Me), 11.7(36), 9.7,9.3(25Me). IR (CHCl$_3$)

3473 (br), 2935 (s), 2876 (sh), 2824 (sh), 1744, 1717 (sh), 1704(sh), 1651 (s), 1454 cm$^{-1}$.

EXAMPLES 133A and 133B

Formula II: $R^0$=ethyl; $R^5$=—OH; m=1; $R^7$=-Phenyl

To the compound resulting from Example 132 (900 mg, 1.02 mmol) in 6.5 mL of methanol was sequentially added tellurium (IV) oxide (32 mg, 0.3 equivalents) and 288 μL (2.5 equivalents) of 30% aqueous hydrogen peroxide and 18 μL concentrated HCl. The reaction was stirred at room temperature for 8 hours and partitioned between water and methylene chloride. The organic layer was washed with 1M aqueous NaHSO$_3$ solution followed by a brine. After drying the organic layer with MgSO$_4$, the solids were filtered, and the flitrate was concentrated under reduced pressure. The residue was dried to constant weight to give 975 mg of crude product as a mixture of sulfoxide isomers. After purification by silica gel column chromatography eluting with 35% acetone in hexane, 236 mg of isomer 133A and 600 mg of the other isomer (133B) were obtained. Example 133A: MS (FAB) m/e 938 (M+K)$^+$. $^{13}$C NMR (CDCl$_3$) δ213.5(C22), 196.2,192.4(9), 169.1,168.7(1), 165.9,164.7(8), 144.6(Phenyl ring C attached to S), 139.6,138.7(19), 132.4,131.7(27), 130.8, 129.2, 129.0, 125.2, 125.2(phenyl ring C's), 128.9(28), 123.2,123.0(20), 98.6,96.9(10), 78.2,78.1 (31), 77.7,76.9(26), 76.6,75.2(15), 73.7,73.6(13), 72.9,72.1(14), 70.1,69.2(24), 65.9,65.6(32), 57.4,56.9(15OMe), 56.7,56.3, 56.1,56.0,55.9(13OMe,31OMe,2), 54.9,54.6(21), 52.7(2), 48.5,48.4(18), 43.8,39.2(6), 43.4,42.8(23), 40.2,39.7(25), 35.5,33.3(16), 34.5,33.5(11), 33.4(29), 32.8(12), 32.7,32.6(30), 28.8,28.7(33 or 34?), 27.7,26.1(3), 26.4, 26.0(17), 24.6,24.5,24.1(5,35), 22.0,21:8(33 or 34?), 21.2, 20.8(4), 20.5,19.4(17Me), 16.2,16.0(11Me), 15.8,15.7(19Me), 14.2,14.1(27Me), 11.6(36), 9.8,9.3(25Me). IR (CHCl$_3$) 3440(br), 2930(s), 2880(sh), 2830(sh), 1740,1710(sh), 1650(s), 1450 cm$^{-1}$.

Example 133B: MS (FAB) m/e 938 (M+K)$^+$. $^{13}$C NMR (CDCl$_3$) δ213.4(C22), 196.0,192.6(9), 169.0,168.7(1), 165.8,164.8(8), 143.3(phenyl C attached to S), 139.6,138.6(19), 131.4,129.2,128.9,125.5(phenyl C's), 131.2,131.0(27), 129.0(28), 123.3,123.1(20), 98.6,97.1(10), 78.3,77.8(26), 76.6,75.2(15), 73.7,73.6(13), 73.1(31), 72.8, 72.2(14), 70.2,69.2(24), 69.1,69.0(32), 57.4,56.9(15OMe), 56.9,56.7,56.2,56.0(13OMe,31OMe,2), 55.0,54.7(21), 52.8(2), 48.8,48.5(18), 43.8,39.3(6), 43.5,43.5(23), 40.5, 39.9(25), 35.4,32.8(16), 34.5,33.6(11), 32.7,32.5(12), 31.3, 31.0(30), 30.0(29), 29.8,29.7(33 or 34), 27.2,26.1(3), 26.3, 26.0(17), 24.6,24.5,24.3(5,35), 21.2,20.8(4), 20.4,19.5(17Me), 17.3(33 or 34?), 16.2,16.0(11Me), 15.6(19Me), 13.7,13.6(27Me), 11.6(36), 9.9,9.6(25Me). IR (CHCl$_3$) 3440 (br), 2930 (s), 2880 (sh), 2830 (sh), 1740, 1700 (sh), 1650 (s), 1455, 1445 cm$^{-1}$.

TABLE 1

Diagnostic $^{13}$C Chemical Shifts (C$_5$D$_5$N)δ

| Example No. | C31 | C32 | Side Chain Carbons |
|---|---|---|---|
| 8 | 80.9, 81.0 | 46.3,46.4 | SCH$_2$CH$_2$(27.3, 27.4, 27.5), CO(170.9), OPh(151.5-q, 129.8-2C, 126.1-1C, 122.3-2C) |
| 9 | 81.0, 81.1 | 46.4, 46.5 | CH$_2$CH$_2$(27.6, 27.4), CO(172.7), OMe(51.7) |
| 10 | 81.0, 81.1 | 46.3, 46.5 | SCH$_2$CH$_2$(27.3, 27.4, 27.5), CO(172.1), OCH$_2$(60.6), CH3(14.4) |
| 11 | 81.0, 81.1 | 46.3, 46.4 | SCH$_2$CH$_2$(27.3, 27.4, 27.5), CO(172.2), OCH$_2$(63.9), CH$_2$(70.6), OMe(58.6) |
| 12 | 81.0, 81.1 | 46.5 | SCH$_2$CH$_2$(27.0, 27.1, 27.4), CO(170.9), OCH$_2$(60.1, 60.4, 60.7, 61.0), CF3(123.2, 125.2) |
| 13 | 81.0, 81.1 | 46.3, 46.4 | SCH$_2$CH$_2$(27.3, 27.4, 27.6), CO(172.4), OCH$_2$(60.4), CH$_2$OH(67.0) |
| 14 | 81.0, 81.1 | 46.2, 46.3 | SCH$_2$CH$_2$(27.4, 27.5, 27.7), CO(171.6), OCyc(72.8-CH, 31.9-2CH$_2$, 25.6-1CH$_2$, 23.9-2CH$_2$) |
| 15 | 81.0, 81.1 | 46.1, 46.2 | SCH$_2$CH$_2$(27.4, 27.6), CO(171.5), Ot-Bu(28.1) |
| 16 | 81.0, 81.1 | 46.3, 46.4 | SCH$_2$CH$_2$(27.1, 27.4, 27.6), CO(172.0), OCH$_2$(59.3), CH$_2$(56.1), N(CH$_3$)$_2$(43.1) |
| 18 | 81 | 46.3, 46.4 | SCH$_2$CH$_2$(27.3, 27.4), CO(172.0), OCH$_2$ (66.4), Ph(136.9-q, 128.9-2C, 128.5-3C) |
| 19 | 81.1, 81.2 | 46.3, 46.5 | SCH$_2$CH$_2$(27.6, 27.8), COOH(174.6) |
| 20 | 81.0, 81.1 | 46.2, 46.3 | SCH$_2$CH$_2$(27.4, 27.5), CO(171.6), OCH (67.9), (CH$_3$)$_2$(21.8) |
| 21 | 81.1 | 46.2 | SCH$_2$CH$_2$(27.4, 27.6), CO(172.0), OCH (76.8), 2CH$_2$(26.8), 2CH$_3$(9.8) |
| 22 | 81.0, 81.1 | 46.3, 46.5 | SCH$_2$CH$_2$(27.3, 28.2), CONH(174.0) |
| 23 | 81.1, 81.2 | 46.7, 46.8 | SCH$_2$CH$_2$(27.4, 27.6, 28.0, 28.1), CO (170.2), Mor(67.0, 66.8, 46.1, 42.3) |
| 24 | 80.9, 81.0 | 46.2, 46.3 | SCH$_2$CH$_2$(28.1, 28.3, 27.2, 27.3), CO (168.9, 168.1)NHOH |
| 25 | 81.0, 81.1 | 46.4, 46.5 | SCH$_2$CH$_2$(27.3, 27.5), CO(172.8), N(OH)CH3(36.5) |
| 26 | 81.0, 81.1 | 41.3, 41.1 | SCH$_2$CH$_2$(27.3, 27.4), CO(172.6), N (OH)CH(47.4), (CH$_3$)$_2$(19.4) |
| 27 | 81.1, 81.2 | 46.2, 46.3 | SCH$_2$(27.3, 27.4), CO(170.9), OCH$_2$ (66.9), Ph(136.7-q, 129.0-2C, 128.7-1C, 128.6-2C) |
| 28 | 81.1, 81.2 | 46.2, 46.3 | SCH$_2$(27.3, 27.4), CO(171.5), OMe(52.1) |
| 29 | 81.1, 81.2 | 46.0, 46.1 | SCH$_2$(27.3, 27.4), CO(170.3), Ot-Bu (28.1) |
| 30 | 81.2, 81.3 | 45.9, 46.0 | SCH$_2$(27.4), COOH(173.6) |
| 31 | 81.1, 81.2 | 46.1, 46.2 | SCH$_2$(27.3, 27.4), CO(170.9), OCH$_2$ |

TABLE 1-continued

| | Diagnostic $^{13}$C Chemical Shifts ($C_5D_5N$)δ | | |
|---|---|---|---|
| Example No. | C31 | C32 | Side Chain Carbons |
| | | | (61.1), CH3(14.2) |
| 32 | 81.1, 81.2 | 46.0, 46.1 | SCH$_2$(27.3, 27.4), CO(170.5), OCH (68.5), (CH$_3$)$_2$(21.7) |
| 33 | 81.2, 81.3 | 46.4, 46.5 | SCH$_2$(27.3), CO(169.8), OCH$_2$ (60.3, 60.8, 61.3, 61.7), CF3(122.2–125.9) |
| 34 | 81.0, 81.1 | 46.0, 46.1 | SCH$_2$(27.2), CO(171.1), OCH$_2$(60.1), CH$_2$OH(67.4) |
| 35 | 81.1, 81.2 | 46.0, 46.1 | SCH$_2$(27.3, 27.4), CO(171.0), OCH$_2$ (64.3), CH$_2$(70.5), OMe(58.5) |
| 36 | 81.3, 81.4 | 46.7 | SCH$_2$(27.6), CO(171.0), OCH$_2$(60.0), CH$_2$(56.1), N(CH$_3$)$_2$(43.3) |
| 37 | 81.1, 81.2 | 46.0, 46.1 | SCH$_2$(27.3, 27.4), CO(171.1), OCH$_2$ (64.5), CH$_2$(73.1), OCH$_2$(68.4), Ph (138.9-q, 128.8-2C, 128.1-2C, 128.0-1C) |
| 38 | 80.9, 81.0 | 46.4, 46.6 | SCH$_2$(27.3, 27.4), CO(167.5), NHOH |
| 39 | 81.0, 81.1 | 45.5, 45.6 | SCH$_2$(27.3, 27.4), CO(171.4), N(OH)CH$_3$ (36.6) |
| 40 | 80.9, 81.0 | 46.6, 46.7 | SCH$_2$(27.3), CH(40.9, 40.8), CH3(17.1), CO(175.6), OMe(51.6) |
| 41 | 81 | 46.5, 46.6 | SCH$_2$(27.3, 27.4), CH(40.9, 40.8), CH3 (17.1), CO(175.2), OCH$_2$(60.5), CH3 (14.3) |
| 42 | 81.0, 81.1 | 46.6, 46.7 | SCH$_2$(27.3, 27.4), CH(41.0, 41.1), CH3 (17.1), CO(175.1), OCH$_2$(66.4), Ph (137.0-q, 129.0-2C, 128.5-3C) |
| 43 | 81.1, 81.0 | 46..7,46.8 | SCH$_2$(27.3, 27.4), CH(41.3, 41.2), CH3 (16.9), COOH(177.8) |
| 44 | 81.1 | 46.3, 46.4 | SCH$_2$(27.3, 27.5), CH$_2$OH(62.1) |
| 45 | 81.1, 81.2 | 46.0, 46.1 | SCH$_2$(27.4, 27.5), CH$_2$(28.9, 29.0), CH$_2$OH(61.0) |
| 46 | 81.0, 81.1 | 45.9, 46.0 | SCH$_2$(27.3, 27.4), CH$_2$(34.0, 34.1), PhOH(157.3-q, 131.7-q, 130.5, 130.0-2C, 116.1-2C) |
| 47 | 80.4 | 51.0, 51.1 | SPhOH(159.0-q, 124.4-q, 136.4-2C, 117.1-2C) |
| 48 | 73.9, 69.3 | 56.8 | SOPhOH(162.0-q, 133.7-q, 128.2-2C, 117.0-2C) |
| 49 | 76.9 | 65.2 | SO$_2$PhOH(163.5-q, 131.3-q, 131.9-2C, 116.1-2C) |
| 50 | 79.5, 73.8 2 diast | 64.6, 61.1 2 diast | SOCH$_2$(53.5, 47.4), CH$_2$OH(55.5)2 diast |
| 52 | 79.4, 73.7 2 diast. | 64.6, 64.7 | SOCH$_2$(51.4, 51.5, 47.3, 47.5), CH$_2$, C30, 33, 34(31.6, 29.9, 27.5, 27.1, 23.5, 18.1), CH$_2$OH(60.9, 61.0)2 diast. |
| 53 | 77.4 | 62.8 | SO$_2$CH$_2$(52.0), CH$_2$, C30, 33, 34(31.7, 31.6, 29.0, 25.6, 21.3),CH$_2$OH(60.4) |
| 54 | 79.2 | 61.2, 61.3 | SOCH$_2$(58.4, 58.6), CO(166.7), OCH$_2$ (67.4), Ph(136.2-q, 128.9-2C, 128.6-3C) |
| 55 | 73.7 | 64.4, 64.5 | SOCH$_2$(54.9), CO(166.9), OCH$_2$(67.5), Ph(136.2-q, 129.0-2C, 128.7-3C) |
| 56 | 77.9 | 62.1, 62.3 | SO$_2$CH$_2$(60.5), CO(164.1), OCH$_2$(67.8), Ph(130.2, 130.4-q, 129.0-2C, 128.7-1C, 128.6-2C) |
| 59 | 78 | 62 | SO$_2$CH$_2$(60.6), CO(164.1), OCH$_2$(62.1), CH3(14.0) |
| 60 | 79.2, 80.4 2 diast. | 61.3, 64.6 2 diast. | SOCH$_2$(48.6, 48.7, 44.8, 44.6), CH$_2$, C30, 33, 34(34.0, 31.5, 29.9, 28.3, 27.5, 23.4, 18.0), CO(172.0), OCH$_2$(61.0, 60.9), CH3 (14.2), 2 diast. |
| 61 | 77.3 | 63.1 | SO$_2$CH$_2$(50.3), CH$_2$, C30, 33, 34(31.5, 31.6, 28.9, 29.0, 27.0, 21.3), CO(171.1), OCH$_2$(61.1), CH3(14.2) |
| 62 | 79.2, 79.3 | 61.3, 61.4 | SOCH$_2$(48.5), CH$_2$, C30, 33, 34(33.9, 28.3, 27.8, 23.4, 23.5), CO(171.8), OCH$_2$ (66.7) Ph(136.7-q, 128.9-2C, 128.5-3C) |
| 63 | 73.5 | 64.4, 64.5 | SOCH$_2$(44.5), CH$_2$, C30, 33, 34(31.4, 31.3, 29.7, 29.8, 27.5, 17.9), CO(171.9), OCH$_2$(66.7), Ph(136.6-q, 128.9-2C, 128.5-3C) |
| 64 | 77.2 | 63.1 | SO$_2$CH$_2$(50.2), CH$_2$, C30, 33, 34(31.5, 31.4, 28.8, 28.9, 27.0, 21.3), CO(171.0), OCH$_2$(66.9), Ph(136.5-q, 128.9-2C, 128.5-3C) |
| 65 | 79.2 | 61.2, 61.4 | SOCH$_2$(48.7, 48.8), CH$_2$, C30, 33, 34 (34.0, 28.1, 23.4) CO(171.4), OCH(68.3), |

TABLE 1-continued

| | Diagnostic $^{13}$C Chemical Shifts $(C_5D_5N)\delta$ | | |
|---|---|---|---|
| Example No. | C31 | C32 | Side Chain Carbons |
| 66 | 73.6 | 64.5 | (CH$_3$)$_2$(21.7) SOCH$_2$((44.8), CH$_2$, C30, 33, 34(31.5, 29.8, 27.7, 17.9), CO(171.5), OCH(68.4), (CH$_3$)$_2$(21.7) |
| 67 | 79.3 | 61.3, 61.4 | SOCH$_2$(48.8), CH$_2$, C30, 33, 34(34.0, 28.3, 28.2, 23.4)CO(171.8), OCH(77.3), 2CH$_2$(26.7), 2CH$_3$(9.7) |
| 68 | 73.7 | 64.6 | SOCH$_2$(44.9, 44.8), CH$_2$, C30, 33, 34 (31.6, 29.8 17.6, 18.0), CO(171.9), OCH (77.4), 2CH$_2$(26.7), 2CH$_3$(9.7) |
| 69 | 79.2, 79.3 | 61.2, 61.3 | SOCH$_2$(48.8, 48.9), CH$_2$, C30, 33, 34 (34.0, 28.3, 26.1, 23.3, 23.4), CO(172.1), N (OH)CH$_3$(34.8, 34.9) |
| 70 | 73.7 | 64.7 | SOCH$_2$(45.1, 45.0), CH$_2$, C30, 33, 34 (31.6, 31.5, 29.8, 25.8, 18.1), CO(172.1), N(OH)CH$_3$(30.7) |
| 71 | 79.3 | 61.3, 61.4 | SOCH$_2$(48.8, 48.9), CH$_2$, C30, 33, 34 (34.1, 28.4, 26.8, 23.4, 23.5), CO(172.0), N(OH)CH(47.6), (CH3)2(19.3) |
| 72 | 73.6 | 64.7 | SOCH$_2$(45.1, 45.0), CH$_2$, C30, 33, 34 (31.6, 31.5 29.8, 29.9, 26.5, 26.4, 18.1)CO (171.8), N(OH)CH(47.5), (CH$_3$)$_2$(19.2) |
| 73 | 79.2 | 60 | |
| 74 | 73.8 | 64 | SOCH$_2$(55.9, 56.0), COOH(170.1) |
| 76 | 79.3, 79.4 | 61.3, 61.4 | SOCH$_2$(49.3), CH$_2$, C30, 33, 34(34.1, 28.3, 23.5), COOH(174.4) |
| 77 | 73.7 | 64.6 | SOCH$_2$(45.6), CH$_2$, C30, 33, 34(31.6, 29.9, 28.4, 18.1)COOH(174.9) |
| 78 | 77.3 | 62.9 | SO$_2$CH$_2$(51.0), CH$_2$, C30, 33, 34 (33.2, 31.7, 31.5, 28.9, 21.3), COOH(173.8) |

In Vitro Assay of Biological Activity

The immunosuppressant activity of the compounds of the present invention was determined using the human mixed lymphocyte reaction (MLR) assay described by Kino, T. et al. in *Transplantation Proceedings*, XIX(5):36–39, Suppl. 6 (1987). The results of the assay, shown below in Table 2, demonstrate that the compounds tested are effective immunomodulators at sub-micromolar concentrations.

TABLE 2

| Example No. | IC$_{50}$ (1 × 10$^{-9}$ M) |
|---|---|
| 18 | 18.5 |
| 90 | 0.75 |
| 126 | 0.75 |
| 127 | 12.5 |
| 128 | 15.5 |
| 129 | 1.15 |
| 130 | 0.58 |
| 131 | 5.2 |
| 132 | 3.4 |
| 133A | 6.2 |
| 133B | 6.5 |

In vitro Assay of Biological Activity (Serum Free MLR)

The in viitro immunosuppressant activity of the compounds of the present invention can also be determined using a variation of the human mixed lymphocyte reaction (MLR) assay described by Kino, T. et al. in Transplantation Proceedings, XIX(5):36–39, Suppl. 6 (1987). In this assay, the cell culture was performed in a serum-free medium, AIM V (GibcoBRL Life Technologies, Grand Island, N.Y.), instead of the usual RPMI 1640 plus 10% heat-inactivated fetal bovine serum medium. The final cell concentrations of the responder and stimulator peripheral blood mononuclear cells were, respectively, 5×105/mL and 2×106/mL of cells pooled from four donors. The results of the assay, shown below in Table 3, demonstrate that the compounds tested are effective immunomodulators at sub-micromolar concentrations.

TABLE 3

| Example No. | IC$_{50}$ (1 × 10$^{-9}$ M) |
|---|---|
| 2 | 0.16 |
| 8 | 1.8 |
| 8A | 0.75 |
| 9 | 8.9 |
| 10 | 3.2 |
| 11 | 2.1 |
| 12 | 1.7 |
| 13 | 3.1 |
| 14 | 6.2 |
| 15 | 1.5 |
| 16 | 2.2 |
| 17 | 31.2 |
| 19 | 2.9 |
| 20 | 12.7 |
| 21 | 5.4 |
| 22 | 0.02 |
| 23 | 0.04 |
| 24 | 0.8 |
| 25 | 0.2 |
| 26 | 7.0 |
| 27 | 3.7 |
| 28 | 1.6 |
| 29 | 1.8 |
| 30 | 9.1 |
| 31 | 8.2 |
| 32 | 6.5 |
| 33 | 47.0 |

TABLE 3-continued

| Example No. | $IC_{50}$ ($1 \times 10^{-9}$ M) |
|---|---|
| 34 | 60.8 |
| 35 | 27.1 |
| 36 | 24.2 |
| 37 | 16.4 |
| 38 | 7.5 |
| 39 | 4.8 |
| 40 | 14.9 |
| 41 | 46.4 |
| 42 | 63.4 |
| 43 | 22.6 |
| 48 | 0.9 |
| 49 | 2.5 |
| 50 | 0.24 |
| 51 | 0.17 |
| 52 | 1.8 |
| 53 | 0.04 |
| 54 | 8.7 |
| 55 | 8.1 |
| 56 | 8.1 |
| 57 | 2.0 |
| 58 | 2.1 |
| 59 | 7.5 |
| 60 | 6.1 |
| 61 | 2.5 |
| 62 | 29.2 |
| 63 | 15.0 |
| 64 | 9.2 |
| 65 | 32 |
| 67 | 25.6 |
| 69 | 6.24 |
| 72 | 32.24 |
| 73 | 9.6 |
| 74 | 57.7 |
| 78 | 30 |
| 79 | 14 |
| 80 | 4.3 |
| 81A | 1.3 |
| 81B | 1.6 |
| 82 | 64 |
| 83A | 70 |
| 83B | 67 |
| 85 | 0.48 |
| 86 | 1.7 |
| 88 | 0.61 |
| 91 | 0.09 |
| 92 | 0.26 |
| 93 | 0.3 |
| 94 | 1.9 |
| 95 | 10.9 |
| 96 | 0.1 |
| 97 | 0.5 |
| 98 | 0.2 |
| 99 | 8.7 |
| 100 | 5.8 |
| 101 | 1.1 |
| 102 | 2.0 |
| 104 | 2.5 |
| 111 | 4.1 |
| 112 | 0.49 |
| 113 | 0.15 |
| 114 | 0.14 |
| 115 | 0.02 |
| 116 | 3.1 |
| 117A | 2.4 |
| 117B | 2.5 |
| 118 | 2.5 |
| 119 | 3.0 |
| 120 | 1.2 |
| 121 | 2.6 |
| 122 | 1.5 |
| 123 | 2.8 |
| 124 | 2.0 |
| 125 | 3.5 |

When examined for immunomodulatory activity using a common in vitro biological assay, the compounds of the invention are seen to be potent immunosuppressive agents. Consequently, the compounds of the invention have immunosuppressive, antimicrobial, antifungal, antiviral, antiinflammatory and antiproliferative activity. Moreover, the compounds of the invention have the ability to reverse chemotherapeutic drug resistance. As agents which block T-cell activation, a prerequisite for HIV proliferation, the compounds are useful as prophylactics for the prevention of HIV replication. While the compounds of the invention are useful when used independently of other agents, combination therapy with other immunosuppressants is beneficial as well. These other agents include but are not limited to FK-506, rapamycin, cyclosporin A, mycophenolic acid, azathioprine, prednisolone, cyclophosphamide, brequinar and leflunomide.

The potent immunomodulatory activity which compounds of the instant invention demonstrate, in common in vitro biological assays, indicate that these compounds possess immunosuppressive, antimicrobial, antifungal, antiviral, antiinflammatory, and antiproliferative activity, and possess the ability to reverse chemotherapeutic drug resistance. As agents which block T-cell activation, a prerequisite for HIV proliferation, the compounds are useful as prophylactics for the prevention of HIV replication. While the compounds of the invention are useful when used alone, combination therapy with other immunosuppressants, such as, FK506, rapamycin, cyclosporin A, picibanil, mycophenolic acid, azathioprine, prednisolone, cyclophosphamide, brequinar and leflunomide, is also beneficial.

As immunosuppressants, the compounds of the present invention are useful when administered for the prevention immune-mediated tissue or organ graft rejection. Examples of transplanted tissues and organs which suffer from these effects are heart, kidney, liver, medulla ossium, skin, cornea, lung, pancreas, intestinum tenue, limb, muscle, nervus, duodenum, small-bowel, pancreatic-islet-cell, and the like; as well as graft-versus-host diseases brought about by medulla ossium transplantation. The regulation of the immune response by the compounds of the invention also finds utility in the treatment of autoimmune diseases, such as rheumatoid arthritis, systemic lupus erythematosus, Hashimoto's thyroiditis, multiple sclerosis, myasthenia gravis, type I diabetes, uveitis, allergic encephalomyelitis, glomerulonephritis, and the like; and further infectious diseases caused by pathogenic microorganisms, such as HIV. In the particular cases of HIV-1, HIV-2 and related retroviral strains, inhibition of T-cell mitosis will suppress the replication of the virus, since the virus relies upon the host T-cell's proliferative functions to replicate.

Further uses include the treatment and prophylaxis of inflammatory and hyperproliferative skin diseases and cutaneous manifestations of immunologically-mediated illnesses, such as psoriasis, atopical dermatitis, contact dermatitis and further eczematous dermatitises, seborrhoeis dermatitis, Lichen planus, Pemphigus, bullous pemphigoid, Epidermolysis bullosa, urticaria, angioedemas, vasculitides, erythemas, cutaneous eosinophilias, Lupus erythematosus, acne and Alopecia areata; various eye diseases (autoimmune and otherwise) such as keratoconjunctivitis, vernal conjunctivitis, keratitis, herpetic keratitis, conical cornea, dystrophia epithelialis corneae, corneal leukoma, ocular pemphigus, Mooren's ulcer, Scleritis, Graves' opthalmopathy, Vogt-Koyanagi-Harada syndrome, sarcoidosis, etc.; reversible obstructive airway disease, which includes conditions such as asthma (for example, bronchial asthma, allergic asthma, intrinsic asthma, extrinsic asthma and dust asthma), particularly chronic or inveterate asthma (for example, late asthma and airway hyper-responsiveness), bronchitis and the like; inflammation of mucosa and blood vessels such as gastric ulcers, vascular damage caused by ischemic diseases and thrombosis. Moreover, hyperproliferative vascular diseases such as intimal smooth muscle cell hyperplasia, restenosis and vascular occlusion, particularly following biologically- or mechanically-mediated vascular injury can be treated or prevented by the compounds of the invention.

Other treatable conditions include but are not limited to ischemic bowel diseases, inflammatory bowel diseases, necrotizing enterocolitis, intestinal lesions associated with thermal burns and leukotriene $B_4$-mediated diseases; intestinal inflammations/allergies such as Coeliac diseases, proctitis, eosinophilic gastroenteritis, mastocytosis, Crohn's disease and ulcerative coliris; food-related allergic diseases which have symptomatic manifestation remote from the gastrointestinal tract (e.g., migraine, rhinitis and eczema); renal diseases such as interstitial nephritis, Goodpasture's syndrome, hemolytic-uremic syndrome and diabetic nephropathy; nervous diseases such as multiple myositis, Guillain-Barre syndrome, Meniere's disease, polyneuritis, multiple neuritis, mononeuritis and radiculopathy; endocrine diseases such as hyperthyroidism and Basedow's disease; hematic diseases such as pure red cell aplasia, aplastic anemia, hypoplastic anemia, idiopathic thrombocytopenic purpura, autoimmune hemolytic anemia, agranulocytosis, pernicious anemia, megaloblastic anemia and anerythroplasia; bone diseases such as osteoporosis; respiratory diseases such as sarcoidosis, fibroid lung and idiopathic interstitial pneumonia; skin disease such as dermatomyositis, leukoderma vulgaris, ichthyosis vulgaris, photoallergic sensitivity and cutaneous T cell lymphoma; circulatory diseases such as arteriosclerosis, atherosclerosis, aortitis syndrome, polyarteritis nodosa and myocardosis; collagen diseases such as scleroderma, Wegener's granuloma and Sjogren's syndrome; adiposis; eosinophilic fasciitis; periodontal disease such as lesions of gingiva, periodontium, alveolar bone and substantia ossea dentis; nephrotic syndrome such as glomerulonephritis; male pattern aleopecia or alopecia senilis by preventing epilation or providing hair germination and/or promoting hair generation and hair growth; muscular dystrophy; Pyoderma and Sezary's syndrome; Addison's disease; active oxygen-mediated diseases, as for example organ injury such as ischemia-reperfusion injury of organs (such as heart, liver, kidney and digestive tract) which occurs upon preservation, transplantation or ischemic disease (for example, thrombosis and cardiac infraction): intestinal diseases such as endotoxin-shock, pseudomembranous colitis and colitis caused by drug or radiation; renal diseases such as ischemic acute renal insufficiency and chronic renal insufficiency; pulmonary diseases such as toxinosis caused by lung-oxygen or drug (for example, paracort and bleomycins), lung cancer and pulmonary emphysema; ocular diseases such as cataracta, siderosis, retinitis, pigmentosa, senile macular degeneration, vitreal scarring and corneal alkali burn; dermatitis such as erythema multiforme, linear IgA ballous dermatitis and cement dermatitis; and others such as gingivitis, periodontitis, sepsis, pancreatitis, diseases caused by environmental pollution (for example, air pollution), aging, carcinogenis, metastasis of carcinoma and hypobaropathy; disease caused by histamine or leukotriene-$C_4$ release; Behcet's disease such as intestinal-, vasculo- or neuro-Behcet's disease, and also Behcet's which affects the oral cavity, skin, eye, vulva, articulation, epididymis, lung, kidney and so on. Furthermore, the compounds of the invention are useful for the treatment and prevention of hepatic disease such as immunogenic diseases (for example, chronic autoimmune liver diseases such as the group consisting of autoimmune hepatitis, primary biliary cirrhosis and sclerosing cholangitis), partial liver resection, acute liver necrosis (e.g., necrosis caused by toxin, viral hepatitis, shock or anoxia), B-virus hepatitis, non-A/non-B hepatitis, cirrhosis (such as alcoholic cirrhosis) and hepatic failure such as fulminant hepatic hilure, late-onset hepatic failure and "acute-on-chronic" liver failure (acute liver failure on chronic liver diseases), and moreover are useful for various diseases because of their useful activity such as augmention of chemotherapeutic effect, preventing or treating activity of cytomegalovirus infection, particularly HCMV infection, anti-inflammatory activity, and so on.

Additionally, some compounds also possess FK-506 antagonistic properties, and are thus useful in the treatment of immunodepression or a disorder involving immunodepression. Examples of disorders involving immunodepression include AIDS, cancer, senile dementia, trauma (including wound healing, surgery and shock), chronic bacterial infection, and certain central nervous system disorders. The immunodepression to be treated may be caused by an overdose of an immunosuppressive macrocyclic compound, for example derivatives of 12-(2-cyclohexyl-1-methylvinyl)-13, 19,21,27-tetramethyl-11,28-dioxa-4-azatricyclo [$22.3.1.0^{4,9}$] octacos-18-ene such as FK-506, or rapamycin. Overdosing of such medicants by patients is quite common upon their realizing that they have forgotten to take their medication at the prescribed time and can lead to serious side effects.

A further situation in which the compounds of the present invention may be used to treat immunosuppression is in vaccination. It is sometimes found that the antigen introduced into the body for the acquisition of immunity from disease also acts as an immunosuppressive agent, and therefore antibodies are not produced by the body and immunity is not acquired. By introducing a compound of the present invention into the body (as in a vaccine), the undesired immunosuppression may be overcome and immunity acquired.

The compounds of the present invention may also find utility in the chemosensitization of drug resistant target cells. Cyclosporin A and FK-506 are known to be effective modulators of P-glycoprotein, a substance which binds to and inhibits the action of anticancer drugs; by inhibiting P-glycoprotein, they are capable of increasing the sensitivity of multidrug resistant (MDR) cells to chemotherapeutic agents. It is believed that the compounds of the invention may likewise be effective at overcoming resistance expressed to clinically useful antitumour drugs such as 5-fluorouracil, cisplatin, methotrexate, vincristine, vinblastine and adriamycin, colchicine and vincristine.

Further, it has recently been shown that the steroid receptor-associated heat shock proteins, hsp56 or hsp59, belong to the FK506 family of immunophilin proteins. The ability of asteroid receptor-associated heat shock protein to bind the immunosuppressive macrolide FK506 may suggest that the steroid receptor and immunophilin signal transduction pathways are functionally interrelated. The combined treatment of compounds of the present invention and low concentrations of asteroid ligand (eg. progesterone, dexamethasone) may result in a significant enhancement of target gene expression over that seen in response to ligand alone. Thus, the compounds of the present invention may potentiate steroid-mediated transactivation.

Aqueous liquid compositions of the present invention are particularly useful for the treatment and prevention of various diseases of the eye such as autoimmune diseases (including, for example, conical cornea, keratitis, dysophia epithelialis corneae, leukoma, Mooren's ulcer, sclevitis and Graves' ophthalmopathy) and rejection of corneal transplantation.

Accordingly the pharmaceutical compositions of the present invention are those which comprise a therapeutically effective amount of a compound of the invention in combination a pharmaceutically acceptable carrier. Particular compositions are those which are useful for treating a patient for immune-mediated organ or tissue allograft rejection, a graft-versus-host disease, an autoimmune disease, a reversible obstructive airway disease, a hyperproliferative disease, or an ischemic or inflammatory intestinal or bowel disease.

Likewise, the methods of the present invention comprising treating a patient in need of immunosuppresive, antiinflammatory, antimicrobial, antifungal, antiviral or antiproliferative thereapy, or requiring the reversal of chemotherapeutic drug resistance, by administering a therapeutically effective amount of a compound of the invention for such time and in such amounts as is necessary to produce the desired result.

When used in the above or other treatments, by "therapeutically effective amount" of one of the compounds of the present invention is meant a sufficient amount of the compound to treat a particular disorder, at a reasonable benefit/risk ratio. The compounds of the invention may be employed in pure form or, where such forms exist, in pharmaceutically acceptable salt, ester or prodrug form. Alternatively, the compound may be administered as pharmaceutical compositions containing the compound of interest in combination with one or more pharmaceutically-acceptable excipients. It will be understood, however, that the total daily usage of the compounds and compositions of the present invention will be decided by the attending physician within the scope of sound medical judgement.

The specific therapeutically-effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or other mammal may range from about 0.001 to about 10 mg/kg of patients body mass/day. For purposes of oral administration, more preferable doses may be in the range of from about 0.005 to about 3 mg/kg/day. If desired, the effective daily dose may be divided into multiple doses for purposes of administration; consequently, single dose compositions may contain such amounts or submultiples thereof to make up the daily dose.

In the pharmaceutical compositions of the present invention, a compound of the invention is combined with a pharmaceutically acceptable carrier or excipient, meaning a non-toxic solid, semi-solid or liquid filler, diluent, encapsulating material or formulation auxiliary of any type. The compositions may be administered orally, rectally, parenterally, intracisternally, intravaginally, intraperitoneally, topically (as by powders, ointments, drops or transdermal patch), bucally, or as an oral or nasal spray. The term "parenteral" as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically-acceptable sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity may be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like, Prolonged absorption of the injectable pharmaceutical form may be brought about by the inclusion of agents which delay absorption, such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues.

The injectable formulations may be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically-acceptable excipient or carrier, such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules may be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically-acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions may contain, in addition to the active compounds, suspending agents as, for example, ethoxylated isostearyl alcohols, polyoxyethylene sorbitol and sorbitan esters, microcrystalline cellulose, aluminum metahydroxide, bentonire, agar-agar, and tragacanth, and mixtures thereof.

Topical administration includes administration to the skin or mucosa, including surfaces of the lung and eye. Compositions for topical administration, including those for inhalation, may be prepared as a dry powder which may be pressurized or non-pressurized. In non-pressurized powder compositions, the active ingredient in finely divided form may be used in admixture with a larger-sized pharmaceutically-acceptable inert carrier comprising particles having a size, for example, of up to 100 micrometers in diameter. Suitable inert carriers include sugars such as lactose. Desirably, at least 95% by weight of the particles of the active ingredient have an effective particle Size in the range of 0.01 to 10 micrometers.

Alternatively, the composition may be pressurized and contain a compressed gas, such as nitrogen or a liquified gas propellant. The liquified propellant medium and indeed the total composition is preferably such that the active ingredient does not dissolve therein to any substantial extent. The pressurized composition may also contain a surface active agent, such as a liquid or solid non-ionic surface active agent or may be a solid anionic surface active agent. It is preferred to use the solid anionic surface active agent in the form of a sodium salt.

A further form of topical administration is to the eye, as for the treatment of immune-mediated conditions of the eye such as automimmue diseases, allergic or inflammatory conditions, and corneal transplants. The compound of the invention is delivered in a pharmaceutically acceptable ophthalmic vehicle, such that the compound is maintained in contact with the ocular surface for a sufficient time period to allow the compound to penetrate the corneal and internal regions of the eye, as for example the anterior chamber, posterior chamber, vitreous body, aqueous humor, vitreous humor, cornea, iris/cilary, lens, choroid/retina and sclera. The pharmaceutically-acceptable ophthalmic vehicle may, for example, be an ointment, vegetable oil or an encapsulating material.

Compositions for rectal or vaginal administration are preferably suppositories which may be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention may also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically-acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic. Methods to form liposomes are known in the art. See, for example, Prescott, Ed., *Methods in Cell Biology*, Volume XIV, Academic Press, New York, N.Y. (1976), p. 33 et seq.

It is understood that the foregoing detailed description and accompanying examples are merely illustrative and are not to be taken as limitations upon the scope of the invention, which is defined solely by the appended claims and equivalents thereof. Variations and modifications of the disclosed embodiments will be apparent to those skilled in the art. Such variations and modifications, including without limitation those relating to the chemical structures, substituents, derivatives, intermediates, syntheses, formulations and/or methods of use of the invention, may be made without departing from the spirit and scope thereof.

What is claimed is:

1. A compound having the formula:

wherein n is zero or one;

m is zero, one or two;

R⁰ is hydrogen, methyl, ethyl, allyl, propyl, 2-hydroxyethyl, cyclopropylmethyl, 2-oxopropyl or 2-ethanal;

R¹ and R² are independently hydrogen or hydroxy, subject to the proviso that when one of R¹ or R² is hydroxy, the other of R¹ and R² is hydrogen; or, alternatively, R¹ and R² taken together are oxo;

R³ and R⁴ are independently hydrogen, halogen, or hydroxy, subject to the proviso that when one of R³ or R⁴ is halogen or hydroxy, the other of R³ and R⁴ is hydrogen; or, alternatively, R³ and R⁴ taken together are oxo;

R⁵ is hydrogen, hydroxy, or protected hydroxy, and R⁶ is hydrogen; or alternatively, R⁵ and R⁶ taken together form a C-23/C-24 bond; and R⁷ is selected from the group consisting of
- (a) —L₁—OH wherein L₁ is alkylene;
- (b) —L₃—C(O)R⁸ wherein L₃ is alkylene and R⁸ is
  - (i) —O—R⁹ wherein R⁹ is hydrogen, loweralkyl, haloalkyl, alkoxyalkyl, aminoalkyl, alkylaminoalkyl, dialkylaminoalkyl, hydroxyalkyl, arylalkyl, aryl, arylalkoxyalkyl, cycloalkyl, cycloalkylalkyl or sulfonic acid-substituted alkyl;
  - (ii) —N(OH)R¹⁰ wherein R¹⁰ is hydrogen or loweralkyl; or
  - (iii) —NR¹¹R¹² wherein R¹¹ and R¹² are independently selected from hydrogen, loweralkyl, and cycloalkyl or R¹¹ and R¹² taken together with the nitrogen to which they are bonded from a heterocyclic ring selected from aziridinyl, azetidinyl, pyrrolidinyl, piperidinyl, piperazinyl, morpholinyl and thiomorpholinyl;
- (c) —C(O)R¹³ wherein R¹³ is
  - (i) heterocyclic,
  - (ii) hydroxyalkyl,
  - (iii) alkoxycarbonyl,
  - (iv) —L₄—NR¹⁴R¹⁵ wherein L₄ is alkylene or hydroxy-substituted alkylene, R¹⁴ is hydrogen or lower alkyl and R¹⁵ is —C(O)—R¹⁶ wherein R¹⁶ is loweralkyl or —NH₂ or R¹⁴ and R¹⁵ taken together with the nitrogen atom to which they are bonded form a heterocyclic ring selected from aziridinyl, azetidinyl, pyrrolidinyl, piperidinyl, piperazinyl, morpholinyl and thiomorpholinyl;
  - (v) —NR¹⁷R¹⁸ wherein R¹⁷ is hydrogen or loweralkyl and R¹⁸ is loweralkyl, aryl, arylalkyl, dialkoxyalkyl or —L₅—C(O)R¹⁹ wherein L₅ is alkylene and R¹⁹ is hydrogen, loweralkyl, cycloalkyl, aryl, arylalkyl, aziridinyl, azetidinyl, pyrrolidinyl, piperidinyl, piperazinyl, morpholinyl, thiomorpholinyl, —OH or (R²⁰)₃—Si—(CH₂)₂- wherein R²⁰ is loweralkyl;
  - (vi) —OR²¹ wherein R²¹ is loweralkyl, aryl or arylalkyl; or
  - (vii) —N(OR¹⁷)R¹⁸ wherein R¹⁷ and R¹⁸ are as defined above;

with the proviso that when R⁷ is —C(O)—R¹³, m is 0;
- (d) —C(=NH)NH₂ wherein m is 0;
- (e) loweralkyl wherein m is 1 or 2;
- (f) cycloalkyl;
- (g) loweralkenyl;
- (h) alkoxyalkyl;
- (i) thioalkoxyalkyl;
- (j) aryl wherein m is 1 or 2;
- (k) arylalkyl wherein m is 1 or 2;
- (l) —L₆—C(R²²)—R²³ wherein L₆ is alkylene, R²² is =O or =N—R²⁴ wherein R²⁴ is —OH, alkoxy, or —NHC(O)NH₂, and R²³ is loweralkyl; and
- (m) hydroxy with the proviso that when R⁷ is hydroxy, m is 2;

or a pharmaceutically acceptable salt, ester, amide or prodrug thereof.

2. A compound according to claim 1 wherein the integer n is one.

3. A compound according to claim 1 wherein R⁰ is selected from the group consisting of ethyl, allyl and propyl.

4. A compound according to claim 1 wherein R¹ and R², taken together, are oxo.

5. A compound according to claim 1 wherein R³ and R⁴ are independently selected from the group consisting of hydrogen and hydroxy, provided that at least one of R³ and R⁴ is hydrogen.

6. A compound according to claim 1 wherein R⁵ is selected from the group consisting of hydrogen and hydroxy.

7. A compound according to claim 6 wherein R⁵ is hydroxy.

8. A compound according to claim 1 wherein R⁷ is (a) —L₁—OH wherein L₁ is alkylene; (b) —L₃—C(O)R⁸ wherein L₃ is alkylene and R⁸ is (i) —O—R⁹ wherein R⁹ is hydrogen, loweralkyl, haloalkyl, alkoxyalkyl, aminoalkyl, alkylaminoalkyl, dialkylaminoalkyl, hydroxyalkyl, arylaalkyl, or aryl; (ii) —N(OH)R¹⁰ wherein R¹⁰ is hydrogen or loweralkyl; or (iii) —NR¹¹R¹² wherein R¹¹ and R¹² are independently selected from hydrogen and loweralkyl or R¹¹ and R¹² taken together with the nitrogen to which they are bonded form a heterocyclic ring selected from aziridinyl, azetidinyl, pyrrolidinyl, piperidinyl, piperazinyl, and morpholinyl; (c) —C(O)R¹³ wherein R¹³ is (i) heterocyclic, (ii) hydroxyalkyl, (iii) —L₄—NR¹⁴R¹⁵ wherein L₄ is alkylene or hydroxy-substituted alkylene, R¹⁴ is hydrogen or lower alkyl and R¹⁵ is —C(O)—R¹⁶ wherein R¹⁶ is loweralkyl or —NH₂, or (iv) —NR¹⁷R¹⁸ wherein R¹⁷ is hydrogen or loweralkyl and R¹⁸ is loweralkyl, aryl, arylalkyl, dialkoxyalkyl or —L₅—C(O)R¹⁹ wherein L₅ is alkylene and R¹⁹ is hydrogen, loweralkyl, aziridinyl, azetidinyl, pyrrolidinyl, piperidinyl, piperazinyl, or morpholinyl; (d) loweralkyl wherein m is 1 or 2; (e) thioalkoxyalkyl; (f) aryl wherein m is 1 or 2; or (g) —L₆—C(R²²)—R²³ wherein L₆ is alkylene, R²² is =O or =N—R²⁴ wherein R²⁴ is —OH, alkoxy, or —NHC(O)NH₂, and R²³ is loweralkyl.

9. A compound according to claim 1 wherein $R^7$ is (a) —$L_1$—OH wherein $L_1$ is alkylene; (b) —$L_3$—C(O)$R^8$ wherein $L_3$ is alkylene and $R^8$ is (i) —O—$R^9$ wherein $R^9$ is loweralkyl, or haloalkyl; (ii) —N(OH)$R^{10}$ wherein $R^{10}$ is hydrogen, or loweralkyl; or (iii) —NR$^{11}$R$^{12}$ wherein $R^{11}$ and $R^{12}$ are independently selected from hydrogen and loweralkyl or $R^{11}$ and $R^{12}$ taken together with the nitrogen to which they are bonded form a heterocyclic ring selected from aziridinyl, azetidinyl, pyrrolidinyl, piperidinyl, piperazinyl, and morpholinyl; (c) —C(O)$R^{13}$ wherein $R^{13}$ is (i) heterocyclic, (ii) hydroxyalkyl, (iii) —$L_4$—NR$^{14}$R$^{15}$ wherein $L_4$ is alkylene or hydroxy-substituted alkylene, $R^{14}$ is hydrogen or lower alkyl and $R^{15}$ is —C(O)—$R^{16}$ wherein $R^{16}$ is loweralkyl or (iv) —NR$^{17}$R$^{18}$ wherein $R^{17}$ is hydrogen or loweralkyl and $R^{18}$ is loweralkyl, aryl or —$L_5$—C(O)$R^{19}$ wherein $L_5$ is alkylene and $R^{19}$ is aziridinyl, azetidinyl, pyrrolidinyl, piperidinyl, piperazinyl, or morpholinyl; (d) loweralkyl wherein m is 1 or 2; (e) thioalkoxyalkyl; or (f) —$L_6$—C($R^{22}$)—$R^{23}$ wherein $L_6$ is alkylene, $R^{22}$ is =N—$R^{24}$ wherein $R^{24}$ is —NHC(O)NH$_2$, and $R^{23}$ is loweralkyl.

10. A compound according to claim 1 wherein $R^7$ is (a) —$L_1$—OH wherein $L_1$ is alkylene; (b) —$L_3$—C(O)$R^8$ wherein $L_3$ is alkylene and $R^8$ is (i) —N(OH)$R^{10}$ wherein $R^{10}$ is hydrogen or loweralkyl or (ii) —NR$^{11}$R$^{12}$ wherein $R^{11}$ and $R^{12}$ are independently selected from hydrogen and loweralkyl or $R^{11}$ and $R^{12}$ taken together with the nitrogen to which they are bonded form a morpholinyl ring; (c) —C(O)$R^{13}$ wherein $R^{13}$ is (i) heterocyclic, (ii) hydroxyalkyl, or (iii) —$L_4$—NR$^{14}$R$^{15}$ wherein $L_4$ is alkylene or hydroxy-substituted alkylene, $R^{14}$ is hydrogen or lower alkyl and $R^{15}$ is —C(O)—$R^{16}$ wherein $R^{16}$ is loweralkyl; (d) loweralkyl wherein m is 1 or 2; or (e) thioalkoxyalkyl.

11. A compound according to claim 1 wherein $R^7$ is (a) —$L_1$—OH wherein $L_1$ is alkylene; (b) —$L_3$—C(O)$R^8$ wherein $L_3$ is alkylene and $R^8$ is (i) —N(OH)$R^{10}$ wherein $R^{10}$ is hydrogen or loweralkyl or (ii) —NR$^{11}$R$^{12}$ wherein $R^{11}$ and $R^{12}$ are independently selected from hydrogen and loweralkyl or $R^{11}$ and $R^{12}$ taken together with the nitrogen to which they are bonded form a morpholinyl ring; (c) —C(O)$R^{13}$ wherein $R^{13}$ is (i) heterocyclic, (ii) hydroxyalkyl, or (iii) —$L_4$—NR$^{14}$R$^{15}$ wherein $L_4$ is alkylene or hydroxy-substituted alkylene, $R^{14}$ is hydrogen or lower alkyl and $R^{15}$ is —C(O)—$R^{16}$ wherein $R^{16}$ is loweralkyl; (d) loweralkyl wherein m is 1 or 2; or (e) thioalkoxyalkyl.

12. A compound according to claim 1 having the formula:

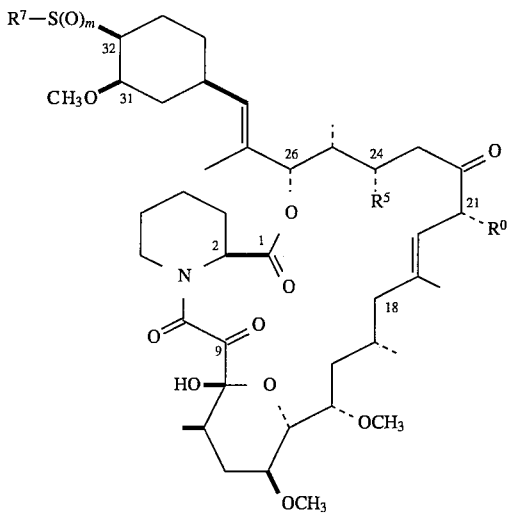

wherein $R^0$, $R^5$, $R^7$ and m are as defined therein.

13. A compound according to claim 12 wherein $R^0$ is selected from the group consisting of ethyl, allyl and propyl.

14. A compound according to claim 12 wherein $R^5$ is selected from the group consisting of hydrogen and hydroxy.

15. A compound according to claim 12 wherein $R^5$ is hydroxy.

16. A compound according to claim 12 wherein $R^7$ is (a) —$L_1$—OH wherein $L_1$ is alkylene; (b) —$L_3$—C(O)$R^8$ wherein $L_3$ is alkylene and $R^8$ is (i) —O—$R^9$ wherein $R^9$ is hydrogen, loweralkyl, haloalkyl, alkoxyalkyl, aminoalkyl, alkylaminoalkyl, dialkylaminoalkyl, hydroxyalkyl, arylaalkyl, or aryl; (ii) —N(OH)$R^{10}$ wherein $R^{10}$ is hydrogen or loweralkyl; or (iii) —NR$^{11}$R$^{12}$ wherein $R^{11}$ and $R^{12}$ are independently selected from hydrogen and loweralkyl or $R^{11}$ and $R^{12}$ taken together with the nitrogen to which they are bonded form a heterocyclic ring selected from aziridinyl, azetidinyl, pyrrolidinyl, piperidinyl, piperazinyl, and morpholinyl; (c) —C(O)$R^{13}$ wherein $R^{13}$ is (i) heterocyclic, (ii) hydroxyalkyl, (iii) —$L_4$—NR$^{14}$R$^{15}$ wherein $L_4$ is alkylene or hydroxy-substituted alkylene, $R^{14}$ is hydrogen or lower alkyl and $R^{15}$ is —C(O)—$R^{16}$ wherein $R^{16}$ is loweralkyl or —NH$_2$, or (iv) —NR$^{17}$R$^{18}$ wherein $R^{17}$ is hydrogen or loweralkyl and $R^{18}$ is loweralkyl, aryl, arylalkyl, dialkoxyalkyl or —$L_5$—C(O)$R^{19}$ wherein $L_5$ is alkylene and $R^{19}$ is hydrogen, loweralkyl, aziridinyl, azetidinyl, pyrrolidinyl, piperidinyl, piperazinyl, or morpholinyl; (d) loweralkyl wherein m is 1 or 2; (e) thioalkoxyalkyl; (f) aryl wherein m is 1 or 2; or (g) —$L_6$—C($R^{22}$)—$R^{23}$ wherein $L_6$ is alkylene, $R^{22}$ is =O or =N—$R^{24}$ wherein $R^{24}$ is —OH, alkoxy, or —NHC(O)NH$_2$, and $R^{23}$ is loweralkyl.

17. A compound according to claim 12 wherein $R^7$ is (a) —$L_1$—OH wherein $L_1$ is alkylene; (b) —$L_3$—C(O)$R^8$ wherein $L_3$ is alkylene and $R^8$ is (i) —O—$R^9$ wherein $R^9$ is loweralkyl, or haloalkyl; (ii) —N(OH)$R^{10}$ wherein $R^{10}$ is hydrogen or loweralkyl; or (iii) —NR$^{11}$R$^{12}$ wherein $R^{11}$ and $R^{12}$ are independently selected from hydrogen and loweralkyl or $R^{11}$ and $R^{12}$ taken together with the nitrogen to which they are bonded form a heterocyclic ring selected from aziridinyl, azetidinyl, pyrrolidinyl, piperidinyl, piperazinyl, and morpholinyl; (c) —C(O)$R^{13}$ wherein $R^{13}$ is (i) heterocyclic, (ii) hydroxyalkyl, (iii) —$L_4$—N$R^{14}R^{15}$ wherein $L_4$ is alkylene or hydroxy-substituted alkylene, $R^{14}$ is hydrogen or lower alkyl and $R^{15}$ is —C(O)—$R^{16}$ wherein $R^{16}$ is loweralkyl or (iv) —N$R^{17}R^{18}$ wherein $R^{17}$ is hydrogen or loweralkyl and $R^{18}$ is loweralkyl, aryl or —$L_5$—C(O)$R^{19}$ wherein $L_5$ is alkylene and $R^{19}$ is aziridinyl, azetidinyl, pyrrolidinyl, piperidinyl, piperazinyl, or morpholinyl; (d) loweralkyl wherein m is 1 or 2; (e) thioalkoxyalkyl; or (f) —$L_6$—C($R^{22}$)—$R^{23}$ wherein $L_6$ is alkylene, $R^{22}$ is =N—$R^{24}$ wherein $R^{24}$ is —NHC(O)NH$_2$, and $R^{23}$ is loweralkyl.

18. A compound according to claim 12 wherein $R^7$ is (a) —$L_1$—OH wherein $L_1$ is alkylene; (b) —$L_3$—C(O)$R^8$ wherein $L_3$ is alkylene and $R^8$ is (i) —N(OH)$R^{10}$ wherein $R^{10}$ is hydrogen or loweralkyl or (ii) —N$R^{11}R^{12}$ wherein $R^{11}$ and $R^{12}$ are independently selected from hydrogen and loweralkyl or $R^{11}$ and $R^{12}$ taken together with the nitrogen to which they are bonded form a morpholinyl ring; (c) —C(O)$R^{13}$ wherein $R^{13}$ is (i) heterocyclic, (ii) hydroxyalkyl, or (iii) —$L_4$—N$R^{14}R^{15}$ wherein $L_4$ is alkylene or hydroxy-substituted alkylene, $R^{14}$ is hydrogen or lower alkyl and $R^{15}$ is —C(O)—$R^{16}$ wherein $R^{16}$ is loweralkyl; (d) loweralkyl wherein m is 1 or 2; or (e) thioalkoxyalkyl.

19. A compound according to claim 12 wherein $R^7$ is (a) —$L_1$—OH wherein $L_1$ is alkylene; (b) —$L_3$—C(O)$R^8$ wherein $L_3$ is alkylene and $R^8$ is (i) —N(OH)$R^{10}$ wherein $R^{10}$ is hydrogen or loweralkyl or (ii) —N$R^{11}R^{12}$ wherein $R^{11}$ and $R^{12}$ are independently selected from hydrogen and loweralkyl or $R^{11}$ and $R^{12}$ taken together with the nitrogen to which they are bonded form a morpholinyl ring; (c) —C(O)$R^{13}$ wherein $R^{13}$ is (i) heterocyclic, (ii) hydroxyalkyl, or (iii) —$L_4$—N$R^{14}R^{15}$ wherein $L_4$ is alkylene or hydroxy-substituted alkylene, $R^{14}$ is hydrogen or lower alkyl and $R^{15}$ is —C(O)—$R^{16}$ wherein $R^{16}$ is loweralkyl; (d) loweralkyl wherein m is 1 or 2; or (e) thioalkoxyalkyl.

20. A compound selected from the group consisting of:

Formula II: $R^0$=ethyl; $R^5$=—OH; m=0; $R^7$=—CH$_2$—CH$_2$—CO-(4-Morpholinyl);

Formula II: $R^0$=ethyl; $R^5$=—OH; m=1; $R^7$=-(4-Hydroxyphenyl);

Formula II: $R^0$=ethyl; $R^5$=—OH; m=2; $R^7$=-(4-Hydroxyphenyl);

Formula II: $R^0$=ethyl; $R^5$=—OH; m=0; $R^7$=—C(O)—CH$_2$NH—C(O)CH$_3$;

Formula II: $R^0$=ethyl; $R^5$=—OH; m=0; $R^7$=—C(O)—(CH$_2$)$_2$NH—C(O)CH$_3$; and Formula II: $R^0$=ethyl; $R^5$=—OH; m=0; $R^7$=(D)—C(O)—CH(OH)—CH$_3$.

21. A pharmaceutical composition for immunomodulatory treatment comprising a therapeutically effective amount of a compound according to claim 1 and a pharmaceutically acceptable carrier.

22. A pharmaceutical composition for immunomodulatory treatment comprising a therapeutically effective amount of a compound according to claim 12 and a pharmaceutically acceptable carrier.

23. A pharmaceutical composition for for immunomodulatory treatment comprising a therapeutically effective amount of a compound of claim 20 in combination with a pharmaceutically acceptable carrier.

24. A method for immunomodulatory treatment comprising administering to a mammal in need of such treatment a therapeutically effective amount of a compound of claim 1.

25. A method for immunomodulatory treatment comprising administering to a mammal in need of such treatment a therapeutically effective amount of a compound of claim 12.

26. A method for immunomodulatory treatment comprising administering to a mammal in need of such treatment a therapeutically effective amount of a compound of claim 20.

* * * * *